United States Patent
Terai et al.

(10) Patent No.: US 10,801,044 B2
(45) Date of Patent: Oct. 13, 2020

(54) METHOD OF PRODUCING FATTY ALCOHOL

(71) Applicant: Kao Corporation, Chuo-ku, Tokyo (JP)

(72) Inventors: Mika Terai, Sakai (JP); Akihito Kawahara, Wakayama (JP); Tatsuro Ozaki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/475,178

(22) PCT Filed: Jan. 29, 2018

(86) PCT No.: PCT/JP2018/002797
§ 371 (c)(1),
(2) Date: Jul. 1, 2019

(87) PCT Pub. No.: WO2018/147118
PCT Pub. Date: Aug. 16, 2018

(65) Prior Publication Data
US 2019/0338318 A1    Nov. 7, 2019

(30) Foreign Application Priority Data
Feb. 8, 2017    (JP) ................................. 2017-021708

(51) Int. Cl.
| C12N 15/09 | (2006.01) |
| C12P 7/04 | (2006.01) |
| C12N 1/20 | (2006.01) |
| C12N 9/02 | (2006.01) |

(52) U.S. Cl.
CPC .................. *C12P 7/04* (2013.01); *C12N 1/20* (2013.01); *C12N 9/0008* (2013.01); *C12Y 203/01041* (2013.01)

(58) Field of Classification Search
CPC .................................................. C12N 9/0008
USPC ....................................................... 435/193
See application file for complete search history.

(56) References Cited

U.S. PATENT DOCUMENTS

| 10,337,037 B2 * | 7/2019 | Ozaki ................ C12N 15/8247 |
| 10,508,292 B2 * | 12/2019 | Kawahara ...... C12Y 203/01041 |
| 2007/0044580 A1 | 3/2007 | Arcas et al. |
| 2009/0298143 A1 | 12/2009 | Roessler et al. |
| 2013/0102040 A1 | 4/2013 | Radakovits et al. |
| 2017/0044580 A1 | 2/2017 | Sugihara et al. |
| 2019/0376099 A1 * | 12/2019 | Terai .............. C12Y 203/01041 |

FOREIGN PATENT DOCUMENTS

| JP | 2005-065658 A | 3/2005 |
| JP | 2011-505838 A | 3/2011 |
| WO | WO 2009/076559 A1 | 6/2009 |
| WO | WO 2013/152051 A2 | 10/2013 |
| WO | WO 2015/133305 A1 | 9/2015 |
| WO | WO 2015/175809 A1 | 11/2015 |
| WO | WO 2016/159869 A1 | 10/2016 |

OTHER PUBLICATIONS

International Search Report (ISR) for PCT/JP2018/002797; I.A. fd Jan. 29, 2018, dated Apr. 24, 2018 from the Japan Patent Office, Tokyo, Japan.
International Preliminary Report on Patentability (IPRP), Chapter I of the Patent Cooperation Treaty, including the Written Opinion for PCT/JP2018/002797; I.A. fd Jan. 29, 2018, dated Aug. 3, 2019, by the International Bureau of WIPO, Geneva, Switzerland.
Domergue, F et al., "Three Arabidopsis fatty acyl-coenzyme A reductases, FAR1, FAR4, and FAR5, generate primary fatty alcohols associated with suberin deposition," Plant Physiol. Aug. 2010;153(4):1539-54. doi: 10.1104/pp. 110.158238. Epub Jun. 22, 2010.
Doan, TTP et al., "Functional expression of five *Arabidopsis* fatty acyl-CoA reductase genes in *Escherichia coli*," J Plant Physiol. May 15, 2009;166(8):787-96. doi: 10.1016/j.jplph.2008.10.003. Epub Dec. 4, 2008.
Tan, X et al., "Photosynthesis driven conversion of carbon dioxide to fatty alcohols and hydrocarbons in cyanobacteria," Metab Eng. Mar. 2011;13(2):169-76. doi: 10.1016/j.ymben.2011.01.001. Epub Jan. 8, 2011.
Zheng, Y-N et al., "Optimization of fatty alcohol biosynthesis pathway for selectively enhanced production of C12/14 and C16/18 fatty alcohols in engineered *Escherichia coli*," Microb Cell Fact. May 20, 2012;11:65. doi: 10.1186/1475-2859-11-65, 11 pages.

\* cited by examiner

*Primary Examiner* — Tekchand Saidha
(74) *Attorney, Agent, or Firm* — Sterne, Kessler, Goldstein & Fox P.L.L.C.

(57) ABSTRACT

A method of producing a long-chain fatty alcohol, containing culturing a microorganism wherein expression of a gene encoding a 3-ketoacyl-ACP synthase and expression of a gene encoding a fatty acyl-CoA reductase are enhanced;
a method of providing ability to produce a long-chain fatty alcohol for a microorganism wherein expression of a gene encoding a 3-ketoacyl-ACP synthase and expression of a gene encoding a fatty acyl-CoA reductase are enhanced in a microorganism cell; and
a transformant of a microorganism in which expression of a gene encoding a β-ketoacyl-ACP synthase and expression of a gene encoding a fatty acyl-CoA reductase are enhanced.

19 Claims, 2 Drawing Sheets
Specification includes a Sequence Listing.

SEQUENCE LISTING

<160> NUMBER OF SEQ ID NOS: 101

<210> SEQ ID NO 1
<211> LENGTH: 475
<212> TYPE: PRT
<213> ORGANISM: Nannochloropsis oculata

<400> SEQUENCE: 1

```
Met Met Glu Lys Leu Thr Leu Ala Val Val Gly Ser Leu Ala Leu Thr
 1               5                  10                  15

Ser Ala Phe Gln Pro Ser Ser Phe Phe Leu Arg Gln Thr Ser Ser Val
            20                  25                  30

Ser Ser Ser Ser Ser Ser Arg Thr Val Arg Arg Ala Ser Gly Glu
        35                  40                  45

Val Ser Met Ala Asp Leu Pro Pro Leu Val Arg Lys Arg Val Val Ile
50                  55                  60

Thr Gly Val Gly Ala Val Ser Pro Leu Gly Trp Gly Asp Asp Phe Trp
65                  70                  75                  80

Asn Gly Leu Val Glu Gly Arg Ser Gly Ile Val Arg Leu Pro Ser Trp
                85                  90                  95

Ala Asp Glu Tyr Pro Ala Arg Ile Gly Gly Leu Val Pro Asp His Phe
            100                 105                 110

Lys Pro Ser Asp Tyr Met Asn Ala Lys Glu Val Lys Arg Gln Ala Arg
        115                 120                 125

Phe Thr His Phe Ala Met Ala Ala Arg Met Ala Val Glu Asp Ala
    130                 135                 140

Lys Leu Asp Leu Glu Lys Val Asp Arg Ser Arg Ala Gly Cys Met Ile
145                 150                 155                 160

Gly Ser Gly Ile Gly Gly Val Glu Ile Phe Glu Lys Asn Cys Gly Glu
                165                 170                 175

Phe Asp Lys Lys Gly Gly Gly Leu Pro Gly Leu Lys Ala Val Ser Pro
            180                 185                 190

Phe Leu Ile Pro Ala Leu Ile Ala Asn Thr Ala Ala Gly Thr Val Ala
        195                 200                 205

Ile Glu Leu Gly Leu Lys Gly Pro Asn Tyr Cys Ser Val Ser Ala Cys
    210                 215                 220

Ala Ser Gly Thr His Thr Ile Gly Asp Ala Phe Phe Leu Gln Asn
225                 230                 235                 240

Gly Met Ala Asp Val Cys Val Thr Gly Gly Thr Glu Ala Ala Ile Thr
                245                 250                 255

Pro Leu Cys Phe Ala Gly Phe Val Ala Ile Arg Ala Leu Thr Thr Ser
            260                 265                 270

Gly Asn Asp Asp Pro Thr Lys Ala Ser Lys Pro Phe Asp Lys Asn Arg
        275                 280                 285

Ala Gly Phe Val Met Ala Glu Gly Ala Gly Met Leu Val Leu Glu Thr
    290                 295                 300

Glu Glu His Ala Lys Ala Arg Gly Ala Thr Ile Tyr Ala Glu Leu Ala
305                 310                 315                 320

Gly Tyr Gly Ala Ser Cys Asp Ala His His Ile Thr Ala Pro His Pro
                325                 330                 335

Glu Gly Glu Gly Leu Ala Asn Ala Met Asn Met Ala Leu Thr Ser Ala
            340                 345                 350

Gly Leu Lys Pro Thr Asp Val Asp Tyr Ile Asn Ala His Gly Thr Ser
        355                 360                 365
```

```
Thr Ala Tyr Asn Asp Lys Phe Glu Thr Leu Ala Ile His Arg Val Phe
    370                 375                 380

Gly Glu His Ala Lys Lys Leu Lys Val Ser Ser Ile Lys Ser Met Thr
385                 390                 395                 400

Gly His Ser Leu Gly Ala Ala Gly Ala Phe Glu Ala Val Ala Cys Ala
                405                 410                 415

Lys Ala Ile Lys Glu Gly Ile Ile Pro Pro Thr Ile Asn Tyr Glu Thr
                420                 425                 430

Pro Asp Pro Asp Cys Asp Leu Asp Tyr Val Pro Asn Lys Ala Ile Lys
                435                 440                 445

His Asp Val Asn Val Ala Ile Ser Asp Asn Leu Gly Phe Gly Gly His
    450                 455                 460

Asn Ala Ala Leu Val Phe Lys Lys Tyr Val Ala
465                 470                 475

<210> SEQ ID NO 2
<211> LENGTH: 1428
<212> TYPE: DNA
<213> ORGANISM: Nannochloropsis oculata

<400> SEQUENCE: 2
atgatggaga agctgaccct cgcagtggtg ggctcccttg ccctgacttc ggccttccag      60
ccctcgtcct tcttcctccg gcagacttcc tccgtcagca gcagcagcag cagcagcagg    120
actgtgcgtc gtgcatcagg ggaagtgagc atggcggact gccccgct tgtccgcaag      180 agggtggtga tcacgggtgt cggcgccgtg tctcctctcg ggtggggaga cgacttctgg    240
aacggtctcg tggagggaag gagcggcatt gtccgcctcc cttcgtgggc ggacgagtac    300
cccgcgcgaa tcgaggcttt ggtcccggat cactttaagc cgagcgacta catgaatgcc    360
aaggaggtga acgacaggc cgcttcacc catttgcca tggcagctgc ccgtatggcc       420
gtggaagacg ccaagctcga cctggagaag gtggaccgct cgcgtgccgg gtgcatgata    480
ggatccggca ttggtggtgt agaaatcttc gagaaaaact gtgggaatt cgacaagaag    540 ggcggagggc tccctggcct caaggctgtc tccccccttcc tgattccggc cctcatcgcc    600
aacaccgcag ccgggacagt ggctattgaa ctcggcttga agggcccgaa ctactgctct    660
gtctccgcct gcgcctcggg cacgcatacc atcggtgatg ccttcttctt cctccaaaac    720
ggcatggcgg acgtttgtgt aacgggcggg acggaagccg ccatcacccc cctctgtttt    780
gcgggatttg tcgccattcg cgcccttacc accagtggca acgacgaccc caccaaggcc    840
tccaagccgt cgacaagaa ccgagccggt ttcgttatgg ccgagggagc ggggatgctc    900
gtccttgaga cggaggaaca cgcgaaggcc cgaggtgcca ccatctatgc cgagcttgct    960
ggctacggcg catcctgcga cgccaccac atcaccgccc ccatcccga aggcgagggg    1020 ctggcgaacg cgatgaatat ggctctgacg tccgccggcc tcaagcctac ggacgtggac    1080
tacattaatg cccatggaac cagcacggcc tacaacgaca aattcgagac gctggccatt    1140
caccgcgtct ttggcgagca cgccaagaag ctgaaggttt cttccatcaa gtcaatgact    1200
ggtcactccc tcggggccgc cggtgccttc gaggccgtgg cgtgcgcgaa ggcaatcaag    1260
gagggcatca tcccgcccac catcaactac gagactcccg atccagactg cgacttggac    1320
tatgttccca caaaggcgat caagcacgac gtgaatgtgg ccatctccga taacctgggc    1380
ttcggcgggc acaacgcggc tttggtcttc aagaagtatg ttgcctag                1428

<210> SEQ ID NO 3
```

```
<211> LENGTH: 491
<212> TYPE: PRT
<213> ORGANISM: Arabidopsis thaliana

<400> SEQUENCE: 3

Met Glu Ser Asn Cys Val Gln Phe Leu Gly Asn Lys Thr Ile Leu Ile
1               5                   10                  15

Thr Gly Ala Pro Gly Phe Leu Ala Lys Val Leu Val Glu Lys Ile Leu
            20                  25                  30

Arg Leu Gln Pro Asn Val Lys Lys Ile Tyr Leu Leu Arg Ala Pro
        35                  40                  45

Asp Glu Lys Ser Ala Met Gln Arg Leu Arg Ser Glu Val Met Glu Ile
50                  55                  60

Asp Leu Phe Lys Val Leu Arg Asn Asn Leu Gly Glu Asp Asn Leu Asn
65                  70                  75                  80

Ala Leu Met Arg Glu Lys Ile Val Pro Val Pro Gly Asp Ile Ser Ile
                85                  90                  95

Asp Asn Leu Gly Leu Lys Asp Thr Asp Leu Ile Gln Arg Met Trp Ser
            100                 105                 110

Glu Ile Asp Ile Ile Asn Ile Ala Ala Thr Thr Asn Phe Asp Glu
        115                 120                 125

Arg Tyr Asp Ile Gly Leu Gly Ile Asn Thr Phe Gly Ala Leu Asn Val
130                 135                 140

Leu Asn Phe Ala Lys Lys Cys Val Lys Gly Gln Leu Leu Leu His Val
145                 150                 155                 160

Ser Thr Ala Tyr Ile Ser Gly Glu Gln Pro Gly Leu Leu Leu Glu Lys
                165                 170                 175

Pro Phe Lys Met Gly Glu Thr Leu Ser Gly Asp Arg Glu Leu Asp Ile
            180                 185                 190

Asn Ile Glu His Asp Leu Met Lys Gln Lys Leu Lys Glu Leu Gln Asp
        195                 200                 205

Cys Ser Asp Glu Glu Ile Ser Gln Thr Met Lys Asp Phe Gly Met Ala
210                 215                 220

Arg Ala Lys Leu His Gly Trp Pro Asn Thr Tyr Val Phe Thr Lys Ala
225                 230                 235                 240

Met Gly Glu Met Leu Met Gly Lys Tyr Arg Glu Asn Leu Pro Leu Val
                245                 250                 255

Ile Ile Arg Pro Thr Met Ile Thr Ser Thr Ile Ala Glu Pro Phe Pro
            260                 265                 270

Gly Trp Ile Glu Gly Leu Lys Thr Leu Asp Ser Val Ile Val Ala Tyr
        275                 280                 285

Gly Lys Gly Arg Leu Lys Cys Phe Leu Ala Asp Ser Asn Ser Val Phe
290                 295                 300

Asp Leu Ile Pro Ala Asp Met Val Val Asn Ala Met Val Ala Ala Ala
305                 310                 315                 320

Thr Ala His Ser Gly Asp Thr Gly Ile Gln Ala Ile Tyr His Val Gly
                325                 330                 335

Ser Ser Cys Lys Asn Pro Val Thr Phe Gly Gln Leu His Asp Phe Thr
            340                 345                 350

Ala Arg Tyr Phe Ala Lys Arg Pro Leu Ile Gly Arg Asn Gly Ser Pro
        355                 360                 365

Ile Ile Val Val Lys Gly Thr Ile Leu Ser Thr Met Ala Gln Phe Ser
370                 375                 380

Leu Tyr Met Thr Leu Arg Tyr Lys Leu Pro Leu Gln Ile Leu Arg Leu
```

```
                385               390               395               400
           Ile Asn Ile Val Tyr Pro Trp Ser His Gly Asp Asn Tyr Ser Asp Leu
                           405               410                   415

Ser Arg Lys Ile Lys Leu Ala Met Arg Leu Val Glu Leu Tyr Gln Pro
                           420               425                   430

Tyr Leu Leu Phe Lys Gly Ile Phe Asp Asp Leu Asn Thr Glu Arg Leu
                           435               440                   445

Arg Met Lys Arg Lys Glu Asn Ile Lys Glu Leu Asp Gly Ser Phe Glu
                       450               455               460

Phe Asp Pro Lys Ser Ile Asp Trp Asp Asn Tyr Ile Thr Asn Thr His
           465               470               475                   480

Ile Pro Gly Leu Ile Thr His Val Leu Lys Gln
                           485               490
```

<210> SEQ ID NO 4
<211> LENGTH: 1476
<212> TYPE: DNA
<213> ORGANISM: Arabidopsis thaliana

<400> SEQUENCE: 4

```
atggaatcca attgtgttca atttctcggt aacaagacca ttctcatcac aggagctcct      60
ggttttcttg ccaaggtttt ggtagagaaa atactaaggt tgcaaccaaa tgtgaagaag     120
atataccttc tgttgagagc tcccgacgaa aaatcagcca tgcaacgcct acgtagtgag     180
gttatggaga tcgacctttt taaagtgttg aggaacaatc taggagaaga caatttgaat     240
gccttgatgc gggaaaaaat tgtgccggtt ccaggtgata tatcgatcga taatttggga     300
ttgaaagaca ctgatctcat acaacgtatg tggagtgaga ttgatatcat aatcaacata     360
gcagccacaa caaatttcga tgaaagatat gatattggtc ttggcatcaa cacatttgga     420
gccctgaatg ttctcaactt cgccaaaaag tgtgttaaag acaattgct tctccatgtc     480
tcaaccgcgt ataagcggt gaacaacct ggattgttac tagagaaacc attcaagatg     540
ggggagactc tcagcgggga tcgggaacta gacatcaata tagaacatga tctaatgaaa     600
caaaaattga agagcttca agattgttct gatgaagaga tctcgcaaac aatgaaagat     660
tttggaatgg caagggcaaa gcttcatgga tggccaaata catatgtatt caccaaagca     720
atgggagaga tgctaatggg aaaatacaga gaaaatttgc cacttgttat catacgtcca     780
acaatgatta ctagtactat tgccgaacca ttccccggtt ggattgaagg ttgaaaaca     840
ttagacagtg tgattgttgc atatggtaaa ggaaggctta atgttttcct tgcggattca     900
aactcagtct ttgaccttat accggcagac atggtagtaa atgcgatggt tgcagccgcg     960
acagctcatt cggagacac cgggattcag gcaatatatc atgttggttc gtcttgtaag    1020
aatccagtca cgtttggaca acttcacgat ttcacggctc gttacttcgc taaacgtcct    1080
ttgattggtc ggaatggctc gccaatcata gtggtcaaag gaccattct gtccactatg    1140
gctcaattca gcctctacat gacccttcgt tacaagcttc tctacagat acttcgattg    1200
atcaatatag tttatccatg gagtcacgga gataactaca gtgacctaag ccgcaaaatc    1260
aagctagcta tgcgactagt tgagctttac cagccttact tactcttcaa gggcatattt    1320
gatgatttaa ataccgaaag actgcgaatg aaaagaaagg agaatatcaa agagttagat    1380
ggatcgttcg agttcgatcc caagtccatt gattgggaca attatatcac aaacacccac    1440
attcctggcc tcatcaccca tgtgcttaaa caataa                              1476
```

<210> SEQ ID NO 5
<211> LENGTH: 493
<212> TYPE: PRT
<213> ORGANISM: Arabidopsis thaliana

<400> SEQUENCE: 5

Met Ser Thr Glu Met Glu Val Ser Val Leu Lys Tyr Leu Asp Asn
1               5                   10                  15

Lys Ser Ile Leu Val Val Gly Ala Ala Gly Phe Leu Ala Asn Ile Phe
            20                  25                  30

Val Glu Lys Ile Leu Arg Val Ala Pro Asn Val Lys Lys Leu Tyr Leu
            35                  40                  45

Leu Leu Arg Ala Ser Lys Gly Lys Ser Ala Thr Gln Arg Phe Asn Asp
    50                  55                  60

Glu Ile Leu Lys Lys Asp Leu Phe Lys Val Leu Lys Glu Lys Tyr Gly
65                  70                  75                  80

Pro Asn Leu Asn Gln Leu Thr Ser Glu Lys Ile Thr Ile Val Asp Gly
                85                  90                  95

Asp Ile Cys Leu Glu Asp Leu Gly Leu Gln Asp Phe Asp Leu Ala His
            100                 105                 110

Glu Met Ile His Gln Val Asp Ala Ile Val Asn Leu Ala Ala Thr Thr
        115                 120                 125

Lys Phe Asp Glu Arg Tyr Asp Val Ala Leu Gly Ile Asn Thr Leu Gly
    130                 135                 140

Ala Leu Asn Val Leu Asn Phe Ala Lys Arg Cys Ala Lys Val Lys Ile
145                 150                 155                 160

Leu Val His Val Ser Thr Ala Tyr Val Cys Gly Glu Lys Ser Gly Leu
                165                 170                 175

Ile Met Glu Thr Pro Tyr Arg Met Gly Glu Thr Leu Asn Gly Thr Thr
            180                 185                 190

Gly Leu Asp Ile Asn Tyr Glu Lys Lys Leu Val Gln Glu Lys Leu Asp
        195                 200                 205

Gln Leu Arg Val Ile Gly Ala Ala Pro Glu Thr Ile Thr Glu Thr Met
    210                 215                 220

Lys Asp Leu Gly Leu Arg Arg Ala Lys Met Tyr Gly Trp Pro Asn Thr
225                 230                 235                 240

Tyr Val Phe Thr Lys Ala Met Gly Glu Met Val Gly Thr Lys Arg
                245                 250                 255

Glu Asn Leu Ser Leu Val Leu Leu Arg Pro Ser Ile Ile Thr Ser Thr
            260                 265                 270

Phe Lys Glu Pro Phe Pro Gly Trp Thr Glu Gly Ile Arg Thr Ile Asp
        275                 280                 285

Ser Leu Ala Val Gly Tyr Gly Lys Gly Lys Leu Thr Cys Phe Leu Cys
    290                 295                 300

Asp Leu Asp Ala Val Ser Asp Val Met Pro Ala Asp Met Val Val Asn
305                 310                 315                 320

Ser Ile Leu Val Ser Met Ala Ala Gln Ala Gly Lys Gln Glu Glu Ile
                325                 330                 335

Ile Tyr His Val Gly Ser Ser Leu Arg Asn Pro Met Lys Asn Ser Lys
            340                 345                 350

Phe Pro Glu Leu Ala Tyr Arg Tyr Phe Ser Ile Lys Pro Trp Thr Asn
        355                 360                 365

Lys Glu Gly Lys Val Val Lys Val Gly Ala Ile Glu Ile Leu Ser Ser
    370                 375                 380

```
Met Arg Ser Phe His Arg Tyr Met Thr Ile Arg Tyr Leu Ile Ala Leu
385                 390                 395                 400

Lys Gly Leu Glu Leu Val Asn Ile Ile Leu Cys Lys Leu Phe Glu Lys
            405                 410                 415

Glu Phe Gln Tyr Phe Asn Lys Lys Ile Asn Phe Ile Phe Arg Leu Val
        420                 425                 430

Asp Leu Tyr Gln Pro Tyr Leu Phe Phe Tyr Gly Ile Phe Asp Asp Ser
    435                 440                 445

Asn Thr Glu Lys Leu Arg Lys Met Val Ser Lys Thr Gly Val Glu Asn
    450                 455                 460

Glu Met Phe Tyr Phe Asp Pro Lys Val Leu Asp Trp Asp Asp Tyr Phe
465                 470                 475                 480

Leu Asn Thr His Val Ile Gly Leu Leu Lys Tyr Val Phe
                485                 490
```

<210> SEQ ID NO 6
<211> LENGTH: 1482
<212> TYPE: DNA
<213> ORGANISM: Arabidopsis thaliana

<400> SEQUENCE: 6

```
atgtcgacag aaatggaggt cgttagtgtt cttaagtacc ttgacaacaa atccatattg      60
gtcgttggag ctgctgggtt cttagcaaat atctttgtgg agaagatatt aagggtggca     120
ccaaacgtga agaaactcta tctccttcta agagcatcaa aaggaaaatc tgctacccag     180
aggtttaacg acgagatttt gaagaaagat ttgttcaagg tgctgaagga aagtatggt     240
cccaatctaa atcaacttac atcagagaaa atcactattg tcgacggaga catttgcctt     300
gaggatttag tcttcaaga cttcgacttg gctcatgaga tgatccacca agttgatgcc     360
attgttaatt agctgcaac tactaagttt gatgaaagat acgatgtagc tcttgggatc     420
aacacattgg gtgctctcaa tgtcttgaac tttgccaaga gatgtgcaaa ggttaagatc     480
cttgttcatg tatcaacagc ttacgtgtgc ggagaaaaat ctggcttgat aatggaaaca     540
ccgtaccgta tgggtgagac gttgaatgga accaccggtt tagacatcaa ctacgagaaa     600
aaattggttc aggagaaact tgaccagctc cgagtaatcg gagccgctcc tgaaaccatc     660
acggaaacca tgaaggatct cggactcaga cgggcaaaga tgtacggatg gccaaacaca     720
tatgtgttca ccaaagcaat gggggagatg atggtaggga caaaaagaga aaatctgtca     780
cttgtgttgc ttcgtccttc aattattacc agcacattca agaaccatt tcctggttgg     840
actgagggca tcaggactat tgatagttta gctgttggat atggcaaagg caaactcacg     900
tgcttcctct gtgatcttga tgctgttct gatgtgatgc cggcagatat ggtagtaaat     960
tcgattcttg tatcaatggc cgctcaagcc ggtaaacaag aagagattat ttaccatgtg    1020
ggttcttcac ttagaaatcc gatgaaaaat tcaagtttc ctgaattagc gtatcggtat    1080
ttctcaatca aaccgtggac caacaaagaa gggaaggtcg ttaaggtcgg ggccattgag    1140
atcctgagtt ctatgcgtag tttccataga tacatgacca tacgctactt gattgcattg    1200
aagggacttg aattggtaaa cataatactt tgcaagttgt ttgagaagga atttcagtat    1260
ttcaataaga aaataaattt tatattccgg cttgttgatc tctatcagcc ttacctcttt    1320
ttctatggaa tatttgatga ttcaaacaca gaaaaattgc gaaaaatggt atcgaagacg    1380
ggagtcgaaa acgagatgtt ttatttcgat ccaaaggttc tcgattggga cgactatttt    1440
ttgaacacac atgttattgg gctgcttaag tatgtcttct aa                       1482
```

<210> SEQ ID NO 7
<211> LENGTH: 493
<212> TYPE: PRT
<213> ORGANISM: Arabidopsis thaliana

<400> SEQUENCE: 7

Met Asp Ser Asn Cys Ile Gln Phe Leu His Asp Lys Thr Ile Leu Val
1               5                   10                  15

Thr Gly Val Pro Gly Phe Leu Ala Lys Val Phe Val Glu Lys Ile Leu
            20                  25                  30

Arg Ile Gln Pro Lys Val Lys Lys Leu Phe Leu Leu Arg Ala Ala
        35                  40                  45

Asp Asn Glu Ser Ala Met Gln Arg Phe His Ser Glu Val Leu Glu Lys
50                  55                  60

Asp Leu Phe Arg Val Leu Lys Asn Ala Leu Gly Asp Glu Asn Leu Lys
65                  70                  75                  80

Ala Phe Ile Thr Glu Lys Val Val Pro Ile Pro Gly Asp Ile Ser Val
                85                  90                  95

Asp Asn Leu Gly Val Lys Gly Ser Asp Leu Leu Gln His Met Trp Asn
            100                 105                 110

Glu Ile Asp Ile Ile Val Asn Val Ala Ala Thr Thr Asn Phe Asp Glu
        115                 120                 125

Arg Tyr Asp Val Gly Leu Ser Val Asn Thr Phe Gly Pro Leu Asn Val
130                 135                 140

Leu Asn Phe Ala Lys Lys Cys Val Lys Gly Gln Leu Leu His Val
145                 150                 155                 160

Ser Thr Ala Tyr Val Arg Gly Glu Lys Ser Gly Leu Leu His Glu Lys
                165                 170                 175

Thr Phe His Met Gly Glu Thr Leu Asn Gly His Arg Lys Leu Val Ile
            180                 185                 190

Glu Thr Glu Met Glu Leu Met Lys Gln Lys Leu Lys Glu Leu Gln Lys
        195                 200                 205

Gln Asn Cys Ser Glu Glu Glu Ile Ser Gln Ser Met Lys Asp Leu Gly
210                 215                 220

Met Ser Arg Ala Lys Leu His Gly Trp Pro Asn Thr Tyr Val Phe Thr
225                 230                 235                 240

Lys Ser Met Gly Glu Met Leu Leu Gly Asn Tyr Arg Glu Asn Leu Pro
                245                 250                 255

Ile Val Ile Ile Arg Pro Thr Met Ile Thr Ser Thr Phe Ser Glu Pro
            260                 265                 270

Phe Pro Gly Trp Ile Glu Gly Leu Arg Thr Ile Asp Ser Val Ile Val
        275                 280                 285

Ala Tyr Gly Lys Gly Arg Leu Lys Cys Phe Leu Ala Asp Pro Asn Ser
290                 295                 300

Val Leu Asp Leu Ile Pro Val Asp Met Val Ala Asn Ala Met Val Thr
305                 310                 315                 320

Ala Ala Ala Ile His Ala Gly Lys Leu Gly Ser Gln Thr Val Tyr His
                325                 330                 335

Val Gly Ser Ser Cys Lys Asn Pro Ile Thr Phe Glu Gln Ile His Asp
            340                 345                 350

Leu Ala Ala Ser Tyr Phe Thr Lys Asn Pro Leu Val Arg Arg Asp Gly
        355                 360                 365

Ser Ser Ile Leu Val Ser Lys Gly Thr Ile Leu Ser Thr Met Ala Gln
370                 375                 380

```
Phe Ser Phe Tyr Met Thr Leu Arg Tyr Lys Leu Pro Leu Gln Met Leu
385                 390                 395                 400

Arg Leu Ile Tyr Val Ile Tyr Pro Trp Trp Asn Gly Asn Lys Tyr Lys
            405                 410                 415

Asp Ile Asp Arg Lys Ile Lys Leu Ala Met Arg Leu Val Asp Leu Tyr
        420                 425                 430

Arg Pro Tyr Val Leu Phe Lys Gly Ile Phe Asp Asp Thr Asn Thr Glu
    435                 440                 445

Lys Leu Arg Leu Lys Arg Lys Glu Ile Asn Lys Glu Met Tyr Gly Leu
450                 455                 460

Phe Glu Phe Asp Pro Lys Ser Ile Asp Trp Glu Asp Tyr Met Thr Thr
465                 470                 475                 480

Ile His Ile Pro Gly Leu Ile Thr Tyr Val Leu Lys Lys
                485                 490

<210> SEQ ID NO 8
<211> LENGTH: 1482
<212> TYPE: DNA
<213> ORGANISM: Arabidopsis thaliana

<400> SEQUENCE: 8
atggactcca attgcattca gttcctccat gacaagacga ttctcgtcac cggtgttccc      60
ggtttcctcg ccaaagtgtt tgtggagaaa atattgagga ttcaaccaaa ggtaaagaag     120
cttttccttc ttttgagagc agcagacaat gaatcagcca tgcaacggtt tcacagtgag     180
gttttggaga aagatctttt tagagtgttg aaaaacgctt taggtgatga aatctgaaa      240 gctttcataa cagaaaaagt cgtacctatt cccggtgata tatccgttga taatttggga     300
gtgaagggtt ctgatctctt acaacatatg tggaatgaga ttgatatcat tgtcaatgta     360
gccgccacaa cgaactttga tgaaagatat gatgttggtc ttagcgtcaa cacatttgga     420
ccgctcaatg tcctcaactt tgccaagaag tgtgttaaag acagttgct tcttcatgtt      480 tcaaccgcgt atgtgcgcgg agagaagtct ggacttttac atgagaaaac atttcacatg     540
ggggagacat tgaacggaca tagaaaatta gtcattgaga ccgaaatgga gctaatgaaa     600
caaaaactga agagctaca gaaacaaaat tgttcagaag aagagatttc acagtctatg      660
aaagatcttg gaatgtcaag gcaaagcctt catggatggc caaacacata tgtgtttacc     720
aaatcaatgg gagagatgct tcttggtaat tatagagaaa accttcccat cgttatcatc     780
cgtcccacaa tgatcactag cacttttttca gaaccatttc ccggttggat cgaagggtta    840
agaaccatag acagtgtgat tgttgcatat ggcaaaggaa ggcttaaatg ttttcttgca     900
gatccaaact cagtccttga tcttatacct gtggacatgg tcgcaaacgc aatggtcacg     960
gctgcggcaa tacacgcagg gaagctaggt tcccagaccg tgtaccatgt cggatcatct    1020 tgtaaaaaacc cgatcacatt cgaacagatt catgatctcg cggctagcta cttcacgaaa    1080
aaccctcttg ttagacgcga tggttcatct atactagtct ccaaaggaac tatcttgtcc    1140
acaatggctc agttcagttt ctacatgacc cttcgttaca agctaccttt gcagatgttg    1200
cgattgatat atgtaattta tccttggtgg aatggtaata aatataaaga cattgaccgc    1260
aagattaagc tggcgatgcg gttggtcgac ctctacagac cttatgtctt gtttaagggc    1320
atatttgacg atacgaatac tgagaaactg cggttgaaaa gaaaggagat taataaagaa    1380
atgtatggtt tgtttgaatt tgatccaaag tctattgatt gggaggatta tatgacgacc    1440
attcatattc ccggcctcat cacctatgta ctcaaaaaat aa                        1482
```

<210> SEQ ID NO 9
<211> LENGTH: 496
<212> TYPE: PRT
<213> ORGANISM: Arabidopsis thaliana

<400> SEQUENCE: 9

```
Met Glu Leu Asn Cys Val Gln Phe Leu Arg Asn Lys Thr Ile Leu Val
1               5                   10                  15

Thr Gly Ala Thr Gly Phe Leu Ala Lys Val Phe Val Glu Lys Ile Leu
            20                  25                  30

Arg Val Gln Pro Asn Val Lys Lys Leu Tyr Leu Val Arg Ala Ser
        35                  40                  45

Asp Asn Glu Ala Ala Thr Lys Arg Leu Arg Thr Glu Val Phe Glu Lys
    50                  55                  60

Glu Leu Phe Lys Val Leu Arg Gln Asn Leu Gly Asp Glu Lys Leu Asn
65                  70                  75                  80

Thr Leu Leu Tyr Glu Lys Val Val Ser Val Pro Gly Asp Ile Ala Thr
                85                  90                  95

Asp Gln Leu Gly Ile Asn Asp Ser His Leu Arg Glu Arg Met Gln Lys
            100                 105                 110

Glu Ile Asp Ile Val Val Asn Val Ala Ala Thr Thr Asn Phe Asp Glu
        115                 120                 125

Arg Tyr Asp Val Gly Leu Gly Ile Asn Thr Phe Gly Ala Leu Asn Val
    130                 135                 140

Leu Asn Phe Ala Lys Lys Cys Val Lys Val Gln Leu Leu His Val
145                 150                 155                 160

Ser Thr Ala Tyr Val Cys Gly Glu Lys Pro Gly Leu Ile Pro Glu Lys
                165                 170                 175

Pro Phe Ile Met Glu Glu Ile Arg Asn Glu Asn Gly Leu Gln Leu Asp
            180                 185                 190

Ile Asn Leu Glu Arg Glu Leu Met Lys Gln Arg Leu Lys Glu Leu Asn
        195                 200                 205

Glu Gln Asp Cys Ser Glu Glu Asp Ile Thr Leu Ser Met Lys Glu Leu
    210                 215                 220

Gly Met Glu Arg Ala Lys Leu His Gly Trp Pro Asn Thr Tyr Val Phe
225                 230                 235                 240

Thr Lys Ser Met Gly Glu Met Leu Leu Gly Lys His Lys Glu Asn Leu
                245                 250                 255

Pro Leu Val Ile Ile Arg Pro Thr Met Ile Thr Ser Thr Leu Ser Glu
            260                 265                 270

Pro Phe Pro Gly Trp Ile Glu Gly Leu Arg Thr Val Asp Ser Val Ile
        275                 280                 285

Ile Ala Tyr Gly Lys Gly Val Leu Lys Cys Phe Leu Val Asp Val Asn
    290                 295                 300

Ser Val Cys Asp Met Ile Pro Val Asp Met Val Ala Asn Ala Met Ile
305                 310                 315                 320

Thr Ala Ala Ala Lys His Ala Gly Gly Ser Gly Val His Met Val Tyr
                325                 330                 335

His Val Gly Ser Ser His Gln Asn Pro Val Thr Phe Gly Glu Ile His
            340                 345                 350

Glu Ile Ala Val Arg Tyr Phe Thr Lys Asn Pro Leu Arg Ser Arg Asn
        355                 360                 365

Gly Ser Leu Ile Thr Val Ser Lys Val Arg Phe Ile Pro Thr Met Ala
```

```
                370              375              380
Leu Phe Ser Leu Tyr Met Thr Leu Arg Tyr Lys Pro Leu Gln Leu
385              390              395              400

Leu Lys Leu Val Asp Ile Ile Tyr Pro Trp Arg Asn Gly Asp Lys Tyr
            405              410              415

Gly Asp Lys Asn Arg Lys Ile Glu Leu Val Met Arg Leu Val Glu Leu
            420              425              430

Tyr Glu Pro Tyr Val Leu Phe Lys Gly Ile Phe Asp Asp Arg Asn Thr
        435              440              445

Lys Ser Leu Cys Ala Asn Gln Lys Glu Glu Ile Lys Asn Thr Glu
        450              455              460

Lys Leu Met Phe Asp Phe Asp Pro Lys Gly Ile Asn Trp Gly Asp Tyr
465              470              475              480

Leu Thr Asn Ile His Ile Ser Gly Leu Val Thr His Val Leu Lys Lys
            485              490              495

<210> SEQ ID NO 10
<211> LENGTH: 1491
<212> TYPE: DNA
<213> ORGANISM: Arabidopsis thaliana

<400> SEQUENCE: 10
```

| | | | | | |
|---|---|---|---|---|---|
| atggaactca | attgtgttca | atttcttcga | aacaagacga | ttcttgtcac | cggagctacc | 60 |
| ggtttccttg | cgaaggtttt | tgtggagaaa | attctgagag | tgcaaccaaa | tgtgaagaag | 120 |
| ctgtaccttt | tggtgagagc | atctgacaat | gaagctgcca | ctaaacgctt | acgcacagag | 180 |
| gtatttgaga | agaactttta | taaggtattg | agacagaatc | ttggcgatga | gaaattaaat | 240 |
| acattgttgt | acgaaaaagt | tgtttcggtc | ccgggtgata | tagcgactga | tcaattaggc | 300 |
| ataaatgact | ctcatcttag | agaacgtatg | caaaaagaaa | tagatattgt | tgtcaatgtt | 360 |
| gcagccacaa | caaactttga | cgaaagatat | gatgttgggc | ttgggatcaa | tacatttgga | 420 |
| gctctcaacg | tccttaactt | tgccaaaaaa | tgtgttaaag | ttcaattgct | ctccatgtc | 480 |
| tcaactgctt | atgtttgtgg | agaaaagcca | ggtctcatac | ctgaaaaacc | attcatcatg | 540 |
| gaagagattc | gtaacgagaa | tggtcttcaa | ttggatatta | accttgaaag | ggagcttatg | 600 |
| aagcaaagat | tgaaagaact | caatgaacaa | gattgttccg | aagaagacat | tactctttcc | 660 |
| atgaaagaac | tcggaatgga | aagggccaag | cttcatggat | ggcctaacac | atatgttttc | 720 |
| accaaatcaa | tgggagaaat | gcttcttggt | aagcataaag | aaaatctccc | cctcgtcatc | 780 |
| atccgtccca | cgatgatcac | tagtactctt | tcggaacctt | ttcctggttg | gatcgaaggc | 840 |
| ttgagaactg | tcgacagcgt | gattattgca | tatggaaagg | gagtgctcaa | gtgttttctt | 900 |
| gtcgatgtta | actcggtctg | cgatatgata | ccagtggata | tggtggcaaa | cgcaatgatc | 960 |
| acggctgcag | ccaaacacgc | tggaggttca | ggggttcaca | tggtgtacca | tgtcggctca | 1020 |
| tctcaccaga | acccagtcac | atttggagag | attcatgaga | ttgcggttcg | ttactttacg | 1080 |
| aaaaacccett | tgcgaagtcg | caatggctca | ctcataaccg | tctcaaaagt | gaggttcata | 1140 |
| ccaaccatgg | ctttgttcag | cctctacatg | acccctacgtt | acaaactacc | tctccagtta | 1200 |
| ttaaaactag | ttgacataat | atatccttgg | agaaacggag | ataaatatgg | agacaagaac | 1260 |
| cgcaaaatcg | agttggtgat | gagattggta | gagctttatg | agccttatgt | actcttcaag | 1320 |
| ggaatattcg | acgatagaaa | tacaaagagt | ttatgcgcaa | accagaagga | agaggagatc | 1380 |
| aaaaatacag | aaaaattgat | gtttgatttc | gacccaaaag | gaattaattg | gggagattat | 1440 | ctcacaaata tacacatttc tggactcgtc acacacgtgc ttaagaagtg a        1491

<210> SEQ ID NO 11
<211> LENGTH: 25
<212> TYPE: DNA
<213> ORGANISM: Artificial Sequence
<220> FEATURE:
<223> OTHER INFORMATION: primer pBS-SK-fw

<400> SEQUENCE: 11
gcgttaatat tttgttaaaa ttcgc                                      25

<210> SEQ ID NO 12
<211> LENGTH: 23
<212> TYPE: DNA
<213> ORGANISM: Artificial Sequence
<220> FEATURE:
<223> OTHER INFORMATION: primer pBS-SK-rv

<400> SEQUENCE: 12
ctctagagcg gccgccaccg cgg                                        23

<210> SEQ ID NO 13
<211> LENGTH: 37
<212> TYPE: DNA
<213> ORGANISM: Artificial Sequence
<220> FEATURE:
<223> OTHER INFORMATION: primer pBS/NoKASII(-ATG)-fw

<400> SEQUENCE: 13
gcggccgctc tagaggagaa gctgaccctc gcagtgg                         37

<210> SEQ ID NO 14
<211> LENGTH: 40
<212> TYPE: DNA
<213> ORGANISM: Artificial Sequence
<220> FEATURE:
<223> OTHER INFORMATION: primer pBS/NoKASII-rv

<400> SEQUENCE: 14
acaaaatatt aacgcctagg caacatactt cttgaagacc                      40

<210> SEQ ID NO 15
<211> LENGTH: 37
<212> TYPE: DNA
<213> ORGANISM: Artificial Sequence
<220> FEATURE:
<223> OTHER INFORMATION: primer pBS/NoKASII(-20)-fw

<400> SEQUENCE: 15
gcggccgctc tagagccctc gtccttcttc ctccggc                         37

<210> SEQ ID NO 16
<211> LENGTH: 35
<212> TYPE: DNA
<213> ORGANISM: Artificial Sequence
<220> FEATURE:
<223> OTHER INFORMATION: primer pBS/NoKASII(-40)-fw

<400> SEQUENCE: 16
gcggccgctc tagagactgt gcgtcgtgca tcagg                           35

<210> SEQ ID NO 17
<211> LENGTH: 36
<212> TYPE: DNA
<213> ORGANISM: Artificial Sequence

```
<220> FEATURE:
<223> OTHER INFORMATION: primer pBS/NoKASII(-60)-fw

<400> SEQUENCE: 17
gcggccgctc tagagagggt ggtgatcacg ggtgtc                                    36

<210> SEQ ID NO 18
<211> LENGTH: 37
<212> TYPE: DNA
<213> ORGANISM: Artificial Sequence
<220> FEATURE:
<223> OTHER INFORMATION: primer RBS/pBS-SK-rv

<400> SEQUENCE: 18
atgtatatct ccttcttact ctagagcggc cgccacc                                   37

<210> SEQ ID NO 19
<211> LENGTH: 40
<212> TYPE: DNA
<213> ORGANISM: Artificial Sequence
<220> FEATURE:
<223> OTHER INFORMATION: primer RBS/AtFAR1-fw

<400> SEQUENCE: 19
gaaggagata tacatatgga atccaattgt gttcaatttc                                40

<210> SEQ ID NO 20
<211> LENGTH: 40
<212> TYPE: DNA
<213> ORGANISM: Artificial Sequence
<220> FEATURE:
<223> OTHER INFORMATION: primer pBS-SK/AtFAR1-rv

<400> SEQUENCE: 20
acaaaatatt aacgcttatt gtttaagcac atgggtgatg                                40

<210> SEQ ID NO 21
<211> LENGTH: 40
<212> TYPE: DNA
<213> ORGANISM: Artificial Sequence
<220> FEATURE:
<223> OTHER INFORMATION: primer RBS/AtFAR2(-120)-fw

<400> SEQUENCE: 21
gaaggagata tacatatggg acttggcata atcagtttcc                                40

<210> SEQ ID NO 22
<211> LENGTH: 39
<212> TYPE: DNA
<213> ORGANISM: Artificial Sequence
<220> FEATURE:
<223> OTHER INFORMATION: primer pBS-SK/AtFAR2-rv

<400> SEQUENCE: 22
acaaaatatt aacgcttaag ctcttccttt caagacatg                                 39

<210> SEQ ID NO 23
<211> LENGTH: 37
<212> TYPE: DNA
<213> ORGANISM: Artificial Sequence
<220> FEATURE:
<223> OTHER INFORMATION: primer RBS/AtFAR3-fw

<400> SEQUENCE: 23
gaaggagata tacatatgtc gacagaaatg gaggtcg                                   37
```

<210> SEQ ID NO 24
<211> LENGTH: 39
<212> TYPE: DNA
<213> ORGANISM: Artificial Sequence
<220> FEATURE:
<223> OTHER INFORMATION: primer pBS-SK/AtFAR3-rv

<400> SEQUENCE: 24
acaaaatatt aacgcttaga agacatactt aagcagccc                    39

<210> SEQ ID NO 25
<211> LENGTH: 39
<212> TYPE: DNA
<213> ORGANISM: Artificial Sequence
<220> FEATURE:
<223> OTHER INFORMATION: primer RBS/AtFAR4-fw

<400> SEQUENCE: 25
gaaggagata tacatatgga ctccaattgc attcagttc                    39

<210> SEQ ID NO 26
<211> LENGTH: 43
<212> TYPE: DNA
<213> ORGANISM: Artificial Sequence
<220> FEATURE:
<223> OTHER INFORMATION: primer pBS-SK/AtFAR4-rv

<400> SEQUENCE: 26
acaaaatatt aacgcttatt ttttgagtac ataggtgatg agg               43

<210> SEQ ID NO 27
<211> LENGTH: 41
<212> TYPE: DNA
<213> ORGANISM: Artificial Sequence
<220> FEATURE:
<223> OTHER INFORMATION: primer RBS/AtFAR5-fw

<400> SEQUENCE: 27
gaaggagata tacatatgga actcaattgt gttcaatttc t                 41

<210> SEQ ID NO 28
<211> LENGTH: 39
<212> TYPE: DNA
<213> ORGANISM: Artificial Sequence
<220> FEATURE:
<223> OTHER INFORMATION: primer pBS-SK/AtFAR5-rv

<400> SEQUENCE: 28
acaaaatatt aacgctcact tcttaagcac gtgtgtgac                    39

<210> SEQ ID NO 29
<211> LENGTH: 1494
<212> TYPE: DNA
<213> ORGANISM: Arabidopsis thaliana

<400> SEQUENCE: 29
atgggacttg gcataatcag tttcctccaa gggaagaagt ttctaatcac tggctcgacc    60
ggtttcttag ctaaagtact gattgagaaa gtcttgagaa tggctcctga tgtcagcaag   120
atatatctct tgattaaagc caaaagcaaa gaagctgcga tcgagcggct aaagaacgag   180
gtgttagatg cagagctttt taatactcta aaagagactc atggagcatc ttacatgtct   240
ttcatgttaa ctaaactcat ccctgtgacc ggaaacattt gcgattcaaa cattgggttg   300
caagcagatt cagctgaaga gattgcgaaa gaagttgatg ttataatcaa ttctgctgct   360

```
aatacaacct tcaatgaaag atacgatgtt gctctggaca tcaacacaag agggcccggt    420
aatctcatgg gattcgccaa gaagtgcaag aaactcaaac tgttcttgca agtatccaca    480
gcttatgtga atggacaaag acaaggaagg atcatggaga agccatttc tatgggagat    540 tgtatagcaa cagagaactt cctcgaagga acagaaaag cattagatgt tgatagagag    600
atgaagttag ctcttgaagc tgctagaaaa gggactcaaa atcaagatga ggcacagaag    660
atgaaggatc tcggtctaga gcgggcaaga tcatatggat ggcaagacac ttatgttttc    720
accaaagcaa tgggtgagat gatgatcaat agcactcgag agacgtacc tgttgttatt    780 ataaggccta gcgtcatcga aagcacttac aaagatcctt ccctggatg gatgaagga    840 aacaggatga tggatcctat agttttatgt tacgggaagg ggcaactcac ggggttttg    900 gttgatccaa aaggagttct tgatgtagtt cctgctgata tggttgttaa tgcaacgtta    960
gctgctatag caaagcatgg aatggcaatg tcagatccgg aacctgaaat aaacgtgtat   1020
cagatcgctt cttcggcgat aaacccgctg gttttcgaag acttagcgga gcttctttat   1080
aaccactaca aaacatcccc atgcatggac tctaaaggtg atcctattat ggtgcgtttg   1140
atgaaacttt tcaattccgt tgatgattc tcggatcatt tgtggagaga tgctcaagaa   1200
cggagtgggt tgatgagtgg tatgagttca gtggatagta agatgatgca gaagctaaag   1260
tttatatgca gaaatctgt tgaacaagcc aaacaccttg ctactattta tgagccatac   1320
actttctatg gtggaagatt tgataacagc aatacacaga gattaatgga gaatatgtca   1380
gaggacgaga agagagaatt tggatttgat gttggaagca ttaactggac ggactacatt   1440
acaaacgttc acattcccgg tttaagaagg catgtcttga aaggaagagc ttaa          1494
```

<210> SEQ ID NO 30
<211> LENGTH: 40
<212> TYPE: DNA
<213> ORGANISM: Artificial Sequence
<220> FEATURE:
<223> OTHER INFORMATION: primer RBS/NoKASII-rv

<400> SEQUENCE: 30
atgtatatct ccttcctagg caacatactt cttgaagacc                              40

<210> SEQ ID NO 31
<211> LENGTH: 40
<212> TYPE: DNA
<213> ORGANISM: Artificial Sequence
<220> FEATURE:
<223> OTHER INFORMATION: primer RBS/BrFAR1-fw

<400> SEQUENCE: 31
gaaggagata tacatatgga atccaactgt gttcagtttc                              40

<210> SEQ ID NO 32
<211> LENGTH: 43
<212> TYPE: DNA
<213> ORGANISM: Artificial Sequence
<220> FEATURE:
<223> OTHER INFORMATION: primer pBS-SK/BrFAR1-rv

<400> SEQUENCE: 32
acaaaatatt aacgcttact gtttaagaac ataggtgatg agg                          43

<210> SEQ ID NO 33
<211> LENGTH: 42
<212> TYPE: DNA

<210> SEQ ID NO 33
<211> LENGTH: 42
<212> TYPE: DNA
<213> ORGANISM: Artificial Sequence
<220> FEATURE:
<223> OTHER INFORMATION: primer RBS/BrFAR5-fw

<400> SEQUENCE: 33
gaaggagata tacatatgga attcaactgt gttcaatttc tc    42

<210> SEQ ID NO 34
<211> LENGTH: 43
<212> TYPE: DNA
<213> ORGANISM: Artificial Sequence
<220> FEATURE:
<223> OTHER INFORMATION: primer pBS-SK/BrFAR5-rv

<400> SEQUENCE: 34
acaaaatatt aacgcttatt tcttaagtac gtgtgtgatg agg    43

<210> SEQ ID NO 35
<211> LENGTH: 1482
<212> TYPE: DNA
<213> ORGANISM: Brassica rapa

<400> SEQUENCE: 35
atggaatcca actgtgttca gtttcttggg gacaagacga ttctcatcac cggtgctcct    60
ggttttcttg ccaaggttct agtagagaaa attctgaggt tgcaaccaaa tgtgaagaag    120
atgtatcttt tgttgagagc ttccgacgat aaggcagcca tgcaacgctt acgtagtgag    180
gttgtggaga tagacctttt tagggtgctg aggaaagatc taggtgaaga gaatctggat    240
aaattagtgc atgaaaaaat cgtgccagtt cccggtgata tatcggttca taatctggga    300
ttgaaagacc ctgatctttt acaacggatg tggaatgaga ttgatatcat catcaatatc    360
gcagcaacaa cgaatttcga tgaaagatac gatatcggtc ttggcatcaa tacattcgga    420
gctctcaatg ttctcaactt tgccaaaaag tgtgttaaaa acaattgct tctccatgtc    480 tcaaccgcat atgtctgcgg agaaaacaaa ggactattcc tggagaaacc attcaagatg    540
ggggagagtc tcagcgggga taagaaacta gacatcaatg tagaattcga attgatgaaa    600
cagaaactga agagctaaa gcatcaagat tgtactgaag aagagatctc acagtcgatg    660
aaagatcttg gaatgacaag ggcaaagctt catggatggc caaatacata tgtattcacc    720
aaagcaatgg gagagatgct aatcggaagc tctagagaaa atttaccact tgttatcatt    780
cgtccaacaa tgattactag tactctcgcc gagccgtttc ctggctggat cgaaggattg    840
agaacaatag atagtgtgat tgttgcatat ggcaaaggaa ggctcaagtg ttttcttgcg    900 gattcaaccct cagtctttga ccttatacca gcggacatgg tggtaaacgc aatgatcgca    960
accgcaacag ctcactctgg agaaaccggg atccagacca tacc catgt cggctcttct    1020 tttcagaatc cggtcacgtt tggacaactc catgacaccg cggctcgtta cttcactaaa    1080
aaacctctgg ttgctcgcaa cggctcacca atcatagtat caaaaggaac gattctaccc    1140
accatggctc aattcagcct ctacatgacc cttcgttaca agcttcctct gcagatactt    1200
cggttgatta atatcatta cccatggagt gaaggagata aatacaatga ccttagccgc    1260
aaactcaagc tagctatgcg actagttgag ctttacgagc cttacttact cttcaagggc    1320
atatttgatg atttaaatac cgaaagactg cgaataagaa gaaagagaa catcaaagag    1380 atggatggat cgttcgaatt tgatcccaag tccatcaact gggacgatta tatcgcaaac    1440
atacacattc ctggcctcat cacctatgtt cttaaacagt aa    1482

<210> SEQ ID NO 36
<211> LENGTH: 1491
<212> TYPE: DNA
<213> ORGANISM: Brassica rapa

<400> SEQUENCE: 36

```
atggaattca actgtgttca atttctccaa aacaagacta ttcttgtcac cggcgctacc      60
ggtttccttg ccaaagtttt tgtcgagaaa attctgagag tacagccaaa tgtgaaaaag     120
ctgtaccttg tggtgagggc atccgacagt gaagctgcga tgaaacgctt acgagcagag     180
gtgtttgaga agatctttt caaggtgttg agagagaata ttggcgaaga gaatttgaat     240
acattgttct ctgaaaaagt tgtcccggta gcaggtgata tttcgaccga ttgttttggc     300
gtgaaagact ctaatctcag agaacgtatg caaaagaaa ttgatattgt tgtaaatgtc     360
gcagccacaa caaactttga cgaaagatat gacgttgggc ttggaatcaa cacatttgga     420
gctctcaatg tccttaactt cgccaaaaaa tgtgttaaag cacaattgct tctccatgtc     480
tcaacggctt atgtttgtgg agaaaagtct ggtctcctac gtgaaaagcc attcgcaatg     540
gaagagattc gtaacgaagc tggtcatcaa ttggatataa actttgaaat ggaactgatg     600
aagaaaagat taaagagct ccatgaccaa gattgttcag atgaagacat tactctctcc     660
atgaaggaac tcggaatgga aagggcaaag ctccatggat ggccaaacac atatgttttc     720
accaaatcaa tggagagat gcttattggt aaccatagag aaagtcttcc tcttgtcatc     780
atccgtccca cgatgatcac cagcactctt tctgaaccat ttcctggttg gatcgaaggg     840
ttaagaactg tagacagcgt gattgttgca tacggaaagg gagtgctcaa gtgttttctt     900
gtcgatgtga actcagtctg cgatatgata ccagtggata tggtggcaaa cgcgatgatc     960
acggctacag ctacacatgc tggaggttca ggggttcaca tggtgtacca tgttggttca    1020
tcacaccaga acccagtgac atttggagaa attcatgaga tttccgttcg ttactttact    1080
aaaagccctt tgcgtagtcg caatggctcg ctcattgccg tctcaaaagt gaggcttata    1140
tcaaccatgg ctttgttcag cctgtacatg acctacgtt tcaaactacc tttacagttg    1200
ttgaaattaa ttgacataat atatccttgg agaagcggag ataaatacgg agacaagaac    1260
cgcaaaatca atatggtgat gagattggta gagctttacg agccttacgt actcttcaag    1320
ggcatattcg acgataggaa tactaagagc ttatgcgcca atcaaaaaga agatgagaca    1380
aaaacttcaa agggatcgat gtttgatttt gacccaaaag cattaattg gggagactac    1440
ctcacaagtg tacatattcc tggcctcatc acacacgtac ttaagaaata a            1491
```

<210> SEQ ID NO 37
<211> LENGTH: 33
<212> TYPE: DNA
<213> ORGANISM: Artificial Sequence
<220> FEATURE:
<223> OTHER INFORMATION: primer pUC118/slr0168up-F

<400> SEQUENCE: 37

```
ggatcctcta gagtcatcgc ctgttggcct acc                                    33
```

<210> SEQ ID NO 38
<211> LENGTH: 35
<212> TYPE: DNA
<213> ORGANISM: Artificial Sequence
<220> FEATURE:
<223> OTHER INFORMATION: primer Kmr/slr0168up-R

<400> SEQUENCE: 38
ttcgctgggt ttatctaccg ttcaaattct gtggg 35

<210> SEQ ID NO 39
<211> LENGTH: 841
<212> TYPE: DNA
<213> ORGANISM: Synechocystis PCC6803

<400> SEQUENCE: 39

```
atcgcctgtt ggcctacctc gccgccgatc gcctaaatct cagcgccaag agtagttccc      60
tcaacaccag tattctgctc agcagtgacc tattcaatca ggaaggggga attgtaacag     120
ccaactatgg ctttgatggt tatatgggaa ttcccggtat ggatggcacc gatgcggaat     180
cccaacagat tgcctttgac aacaatgtgg cctggaataa cctggggggat ttgtccacca     240
ccacccaacg ggcctacact tcggctatta gcacagacac agtgcagagt gtttatggcg     300
ttaatctgga aaaaacgat aacattccca ttgttttttgc gtggcccatt tttcccacca     360
cccttaatcc cacagatttt caggtaatgc ttaacacggg ggaaattgtc accccggtga     420
tcgcctcttt gattcccaac agtgaataca acgaacggca aacggtagta attacgggca     480
attttggtaa tcgtttaacc ccaggcacgg agggagcgat ttatcccgtt tccgtaggca     540
cagtgttgga cagtactcct ttggaaatgg tgggacccaa cggcccggtc agtgcggtgg     600
gtattaccat tgatagtctc aaccccctacg tggccggcaa tggtcccaaa attgtcgccg     660
ctaagttaga ccgcttcagt gacctggggg aagggggctcc cctctggtta gccaccaatc     720
aaaataacag tggcggggat ttatatggag accaagccca atttcgtttg cgaatttaca     780
ccagcgccgg ttttcccccc gatggcattg ccagtttact acccacagaa tttgaacggt     840
a                                                                     841
```

<210> SEQ ID NO 40
<211> LENGTH: 35
<212> TYPE: DNA
<213> ORGANISM: Artificial Sequence
<220> FEATURE:
<223> OTHER INFORMATION: primer Kmr/slr0168down-F

<400> SEQUENCE: 40
ggaatttgta tcgatagcgg aagatattac gggac 35

<210> SEQ ID NO 41
<211> LENGTH: 34
<212> TYPE: DNA
<213> ORGANISM: Artificial Sequence
<220> FEATURE:
<223> OTHER INFORMATION: primer pUC118/slr0168down-R

<400> SEQUENCE: 41
gcatgcctgc aggtcaatca cgttgggtcc caag 34

<210> SEQ ID NO 42
<211> LENGTH: 979
<212> TYPE: DNA
<213> ORGANISM: Synechocystis PCC6803

<400> SEQUENCE: 42

```
agcggaagat attacgggac ggacagttat cctaacccaa actggtgttg attatgaaat      60
tcccggcttt ggtctggtgc aggtgttggg gctggcggat ttggccgggg ttcaggacag     120
ctatgacctg acttacatcg aagatcatga caactattac gacattatcc tcaaagggga     180
cgaagccgca gttcgcccaaa ttaagagggt tgctttgccc tccgaagggg attattcggc     240
```

```
ggtttataat cccggtggcc ccggcaatga tccagagaat ggtcccccag ggccctttac        300
tgtgtccagt agtccccagg taattaaggt aacggatacc atcggccagc ccaccaaagt        360
ctcctatgtg gaagtggatg gccccgtatt gcgtaatccc ttcagtggta ctcccattgg        420
gcaagaggtg ggtttagcgg ttaaagatct ggccacaggt catgaaattt atcagtacac        480
tgacccagat gggaaggtat tttatgcttc ctttgctgcc gctgatgacc aagccacgga        540
tttaaccacg gcgatcgcca atcccacggc catcgattta attaacgcca ggggatttac        600
ggcgggtagt tccgtcaccg tatcgggttc ctacagtcgg gaagcctttt ttgatggatc        660
catgggtttt tatcgacttc tggacgataa cggtgcagtg ctagatccct taacaggtgg        720
tgtaatcaac ccaggacagg taggttatca agaagcagct tggcagata gcaatcgttt         780 gcaagccact ggctccaccc taacggcaga agacctagaa accagagcat tttccttcaa        840
tattttgggt ggcgagttgt atgcgccatt tttaacggtt aatgacagtc tttccggtat        900
taatcagact tattttgcct ttgggtcggc caacccagat ggcatcagcc acagcacaaa        960
cttgggaccc aacgtgatt                                                     979

<210> SEQ ID NO 43
<211> LENGTH: 18
<212> TYPE: DNA
<213> ORGANISM: Artificial Sequence
<220> FEATURE:
<223> OTHER INFORMATION: primer Kmr-F

<400> SEQUENCE: 43
gataaaccca gcgaacca                                                       18

<210> SEQ ID NO 44
<211> LENGTH: 18
<212> TYPE: DNA
<213> ORGANISM: Artificial Sequence
<220> FEATURE:
<223> OTHER INFORMATION: primer Kmr-R

<400> SEQUENCE: 44
atcgatacaa attcctcg                                                       18

<210> SEQ ID NO 45
<211> LENGTH: 1489
<212> TYPE: DNA
<213> ORGANISM: Artificial Sequence
<220> FEATURE:
<223> OTHER INFORMATION: kanamycin resistance gene

<400> SEQUENCE: 45
gataaaccca gcgaaccatt tgaggtgata ggtaagatta taccgaggta tgaaaacgag         60
aattggacct ttacagaatt actctatgaa gcgccatatt taaaaagcta ccaagacgaa        120
gaggatgaag aggatgagga ggcagattgc cttgaatata ttgacaatac tgataagata        180
atatatcttt tatatagaag atatcgccgt atgtaaggat ttcaggggc aaggcatagg         240 cagcgcgctt atcaatatat ctatagaatg ggcaaagcat aaaaacttgc atggactaat        300
gcttgaaacc caggacaata accttatagc ttgtaaattc tatcataatt gtggtttcaa        360
aatcggctcc gtcgatacta tgttatacgc caactttcaa aacaactttg aaaaagctgt        420
tttctggtat ttaaggtttt agaatgcaag gaacagtgaa ttggagttcg tcttgttata        480
attagcttct tggggtatct ttaaatactg tagaaaagag gaaggaaata taaatggct        540
```

-continued

| | |
|---|---|
| aaaatgagaa tatcaccgga attgaaaaaa ctgatcgaaa ataccgctg cgtaaaagat | 600 |
| acggaaggaa tgtctcctgc taaggtatat aagctggtgg gagaaaatga aaacctatat | 660 |
| ttaaaaatga cggacagccg gtataaaggg accacctatg atgtggaacg ggaaaaggac | 720 |
| atgatgctat ggctggaagg aaagctgcct gttccaaagg tcctgcactt tgaacggcat | 780 |
| gatggctgga gcaatctgct catgagtgag gccgatggcg tcctttgctc ggaagagtat | 840 |
| gaagatgaac aaagccctga aaagattatc gagctgtatg cggagtgcat caggctcttt | 900 |
| cactccatcg acatatcgga ttgtccctat acgaatagct tagacagccg cttagccgaa | 960 |
| ttggattact tactgaataa cgatctggcc gatgtggatt gcgaaaactg ggaagaagac | 1020 |
| actccattta aagatccgcg cgagctgtat gatttttaa agacggaaaa gcccgaagag | 1080 |
| gaacttgtct tttcccacgg cgacctggga gacagcaaca tctttgtgaa agatggcaaa | 1140 |
| gtaagtggct ttattgatct tgggagaagc ggcagggcgg acaagtggta tgacattgcc | 1200 |
| ttctgcgtcc ggtcgatcag ggaggatatc ggggaagaac agtatgtcga gctatttttt | 1260 |
| gacttactgg ggatcaagcc tgattgggag aaaataaaat attatatttt actggatgaa | 1320 |
| ttgttttagt acctagattt agatgtctaa aaagctttaa ctacaagctt tttagacatc | 1380 |
| taatcttttc tgaagtacat ccgcaactgt ccatactctg atgttttata tcttttctaa | 1440 |
| aagttcgcta gatagggggtc ccgagcgcct acgaggaatt tgtatcgat | 1489 |

<210> SEQ ID NO 46
<211> LENGTH: 20
<212> TYPE: DNA
<213> ORGANISM: Artificial Sequence
<220> FEATURE:
<223> OTHER INFORMATION: primer slr0168up-R

<400> SEQUENCE: 46
taccgttcaa attctgtggg                                              20

<210> SEQ ID NO 47
<211> LENGTH: 36
<212> TYPE: DNA
<213> ORGANISM: Artificial Sequence
<220> FEATURE:
<223> OTHER INFORMATION: primer slr0168up/Pcpc560-F

<400> SEQUENCE: 47
agaatttgaa cggtaacctg tagagaagag tccctg                            36

<210> SEQ ID NO 48
<211> LENGTH: 21
<212> TYPE: DNA
<213> ORGANISM: Artificial Sequence
<220> FEATURE:
<223> OTHER INFORMATION: primer Pcpc560-R

<400> SEQUENCE: 48
tgaattaatc tcctacttga c                                            21

<210> SEQ ID NO 49
<211> LENGTH: 560
<212> TYPE: DNA
<213> ORGANISM: Synechocystis PCC6803

<400> SEQUENCE: 49

| | |
|---|---|
| acctgtagag aagagtccct gaatatcaaa atggtgggat aaaaagctca aaaggaaag | 60 |
| taggctgtgg ttccctaggc aacagtcttc cctaccccac tggaaactaa aaaaacgaga | 120 |

```
aaagttcgca ccgaacatca attgcataat tttagccota aaacataagc tgaacgaaac    180
tggttgtctt cccttcccaa tccaggacaa tctgagaatc ccctgcaaca ttacttaaca    240
aaaaagcagg aataaaatta acaagatgta acagacataa gtcccatcac cgttgtataa    300
agttaactgt gggattgcaa aagcattcaa gcctaggcgc tgagctgttt gagcatcccg    360
gtggcccttg tcgctgcctc cgtgtttctc cctggattta tttaggtaat atctctcata    420
aatccccggg tagttaacga aagttaatgg agatcagtaa caataactct agggtcatta    480
ctttggactc cctcagttta tccgggggaa ttgtgtttaa gaaaatccca actcataaag    540
tcaagtagga gattaattca                                                560
```

<210> SEQ ID NO 50
<211> LENGTH: 20
<212> TYPE: DNA
<213> ORGANISM: Artificial Sequence
<220> FEATURE:
<223> OTHER INFORMATION: primer Trbc-F

<400> SEQUENCE: 50

```
gttacagttt tggcaattac                                                 20
```

<210> SEQ ID NO 51
<211> LENGTH: 38
<212> TYPE: DNA
<213> ORGANISM: Artificial Sequence
<220> FEATURE:
<223> OTHER INFORMATION: primer Km/Trbc-R

<400> SEQUENCE: 51

```
ttcgctgggt ttatcttccc cacttagata aaaaatcc                             38
```

<210> SEQ ID NO 52
<211> LENGTH: 183
<212> TYPE: DNA
<213> ORGANISM: Synechocystis PCC6803

<400> SEQUENCE: 52

```
gttacagttt tggcaattac taaaaaactg acttcaattc aatgttagcc cgctcccgcg     60
ggttttttgt tgcttttttca cagtgactat aggtaatcag caacacaata cggccctgtt   120
ctttggacag ttttttgtata atgttgaccg catcctgacc ggattttttta tctaagtggg  180 gaa                                                                  183
```

<210> SEQ ID NO 53
<211> LENGTH: 37
<212> TYPE: DNA
<213> ORGANISM: Artificial Sequence
<220> FEATURE:
<223> OTHER INFORMATION: primer Pcpc560/NoKASII(-40)-F

<400> SEQUENCE: 53

```
taggagatta attcaatgac tgtgcgtcgt gcatcag                              37
```

<210> SEQ ID NO 54
<211> LENGTH: 40
<212> TYPE: DNA
<213> ORGANISM: Artificial Sequence
<220> FEATURE:
<223> OTHER INFORMATION: primer Trbc/NoKASII-R

<400> SEQUENCE: 54

```
tgccaaaact gtaacctagg caacatactt cttgaagacc                    40
```

<210> SEQ ID NO 55
<211> LENGTH: 35
<212> TYPE: DNA
<213> ORGANISM: Artificial Sequence
<220> FEATURE:
<223> OTHER INFORMATION: primer pUC118/sll0208up-F

<400> SEQUENCE: 55

```
ggatcctcta gagtcattcc tcgcccattt tcagg                         35
```

<210> SEQ ID NO 56
<211> LENGTH: 38
<212> TYPE: DNA
<213> ORGANISM: Artificial Sequence
<220> FEATURE:
<223> OTHER INFORMATION: primer Sp/sll0208up-R

<400> SEQUENCE: 56

```
cgaacgaaaa tcgatcgctt tgaaagtcca gttcaagg                      38
```

<210> SEQ ID NO 57
<211> LENGTH: 1038
<212> TYPE: DNA
<213> ORGANISM: Synechocystis PCC6803

<400> SEQUENCE: 57

```
attcctcgcc cattttcagg ctaaatccct cgattccttg attctactgc ggcgagtgtc     60
caatcccagc gcctttgggg tggccaccgt taatgaccaa ggcaaagttt tagccctagt    120
ggaaaaacca gagcatcccc cttccaactt ggccctagtg ggactttact ttttgccccc    180
gaccattcac caggcgatcg ccaacattga gccctctgcc ggggagaac tagaaatcac     240
cgatgcaatt caatatctga tcagccatga ttatcgggtg gaatccctac aactaaaagg    300
atggtggctc gacaccggta agaaagacga cctgctggcc gccaatcaga ttatcctcga    360
taccctagtg gaaaaaaaca tccaaggcac cgtagacgat caaagcaaaa tctccggtcg    420
ggtaaccatt ggccccccaca gtcaaattat caacagcgtc atccgtggcc ccgtggcgat    480
cggcccccaac tgtcatctgg aaaactgctt catcggtccc tatagcagta ttgccgaggg    540
agttaaaatc agggatgcag atcttgaaca tagtgtcgtg ctccaaggag ctagcattgt    600
ggccatccaa caaagaattg tcgatagtgt catcggcaaa aacgccaaaa ttttttcccgc    660
tccccgccgt cccaggcctt tgcgcttcct gattggtaat gattcccaag tggaactaat    720
tggaccctct tcctatcccc aggactaacc tccccccccag caacttagac tagttttgct    780
agaatggtgc caactcaaat cgcagcagat ctggccatgt agattactaa atcaactgga    840
taggtgttcc ctatggttag accgctatga tcctccggga tttgcattaa tttagagtct    900
gtattataaa gacaaccggg ggttaatttc ttaacctttc tttactttga ttctctggtc    960
ttcatcgacc ttttaaccgt ccatccacag gagtccaacg ccctatgcc cgagcttgct    1020
gtccgcaccg aatttgac                                                  1038
```

<210> SEQ ID NO 58
<211> LENGTH: 38
<212> TYPE: DNA
<213> ORGANISM: Artificial Sequence
<220> FEATURE:
<223> OTHER INFORMATION: primer Sp/sll0209down-F

<400> SEQUENCE: 58

```
aaacccttgc atatgatcac gatcgagaag atggaagc                              38
```

<210> SEQ ID NO 59
<211> LENGTH: 35
<212> TYPE: DNA
<213> ORGANISM: Artificial Sequence
<220> FEATURE:
<223> OTHER INFORMATION: primer pUC118/sll0209down-R

<400> SEQUENCE: 59

```
gcatgcctgc aggtcatcag ttgtgcccgc tgtgc                                 35
```

<210> SEQ ID NO 60
<211> LENGTH: 1145
<212> TYPE: DNA
<213> ORGANISM: Synechocystis PCC6803

<400> SEQUENCE: 60

```
caccagggtg aaagcggatg gggtgcatat tctcaagggg gggattgtag aacattccct      60
tgatattacc tgggaaatta tgaagattgt ggagatggat attccctccc ggcaaatgtt     120
cgcctgtttt gcggaggcca ttttgctaga gtttgagggc tggcgcacta atttttcctg     180
gggccgcaac caaatttccg ttaataaaat ggaggcgatt ggtgaagctt ctgtcaagca     240
tggcttttgc cctttagtag ctctttaggc cgacaggata gggcgtgtgt ggagctggtg     300
aacaaggtct gaaacagtgg ccagtagtca atatttcccc gtgctttcca tagaagatat     360
ctgcttaatc taaatattc ctgccttcct agagactta taaatgggtg aattcagagg      420
attcgtgcct aaaactgctg ggctagctca agagggact gtcttaggta aacttttgaa     480
tcaaagacta atttgacaac caattatcaa agctcaatgc tgctggtcaa agagtctggc     540
tcaattgaga taaacaatgg cccatgagaa aataaaccac caatgtggcg gccgccgctg     600
ctgctacgag agttccggcc agcatcaaag aaaattcctg ctcttcgatc gcctgttgca     660
taaggtggag ggaccaggcc accaaagcca catcaaaaat gagaatgggc accaacatat     720
gtaacaaaat gtaaaccttt ccgttacatt ctaatctatt ggccagcctt ggcaatcaaa     780
aatccggtaa tttaaccttt tctacggttt tgaagcagtg cccaggcaga ttttgcctgt     840
gattctcggg catccattca cttttgtcga tgctggaaaa tttctagccc agccagtgtc     900
ccccagtcta ctcaaaggcg atcgaacagc aaacacattg tccatgtgaa cattggtcag     960
tctccctcct cctgtcggat cagccgctcc tgaacttttc ttagggtgca aacttgattg    1020
gccggtaggc ggggcaatgg taactccaaa ttcggccagg attccacctc aacacaagga    1080
caaagagaat tgggaatttg actgtgggac aggggcaccg gcaacgcaca gcgggcacaa    1140
ctgat                                                                1145
```

<210> SEQ ID NO 61
<211> LENGTH: 25
<212> TYPE: DNA
<213> ORGANISM: Artificial Sequence
<220> FEATURE:
<223> OTHER INFORMATION: primer Sp-F

<400> SEQUENCE: 61

```
atcgattttc gttcgtgaat acatg                                            25
```

<210> SEQ ID NO 62
<211> LENGTH: 24
<212> TYPE: DNA

```
<213> ORGANISM: Artificial Sequence
<220> FEATURE:
<223> OTHER INFORMATION: primer Sp-R

<400> SEQUENCE: 62
catatgcaag ggtttattgt tttc                                          24

<210> SEQ ID NO 63
<211> LENGTH: 1158
<212> TYPE: DNA
<213> ORGANISM: Artificial Sequence
<220> FEATURE:
<223> OTHER INFORMATION: spectinomycin resistance gene

<400> SEQUENCE: 63
atcgattttc gttcgtgaat acatgttata taactataa ctaataacgt aacgtgactg      60
gcaagagata ttttaaaac aatgaatagg tttacactta ctttagtttt atggaaatga    120
aagatcatat catatataat ctagaataaa attaactaaa ataattatta tctagataaa    180
aaatttagaa gccaatgaaa tctataaata aactaaatta gtttattta attaacaact    240 atggatataa ataggtact aatcaaaata gtgaggagga tatatttgaa tacatacgaa    300
caaattaata aagtgaaaaa aatacttcgg aaacatttaa aaaataaccct tattggtact    360 tacatgtttg gatcaggagt tgagagtgga ctaaaaccaa atagtgatct tgactttta    420 gtcgtcgtat ctgaaccatt gacagatcaa agtaaagaaa tacttataca aaaaattaga    480
cctatttcaa aaaaaatagg agataaaagc aacttacgat atattgaatt aacaattatt    540
attcagcaag aaatggtacc gtggaatcat cctcccaaac aagaatttat ttatggagaa    600
tggttacaag agctttatga acaaggatac attcctcaga aggaattaaa ttcagattta    660
accataatgc tttaccaagc aaaacgaaaa aataaaagaa tatacggaaa ttatgactta    720
gaggaattac tacctgatat tccatttct gatgtgagaa gagccattat ggattcgtca    780
gaggaattaa tagataatta tcaggatgat gaaaccaact ctatattaac tttatgccgt    840
atgattttaa ctatggacac gggtaaaatc ataccaaaag atattgcggg aaatgcagtg    900
gctgaatctt ctccattaga acatagggag agaattttgt tagcagttcg tagttatctt    960
ggagagaata ttgaatggac taatgaaaat gtaaatttaa ctataaacta tttaaataac   1020
agattaaaaa aattataaaa aaattgaaaa aatggtggaa acactttttt caatttttt    1080 gttttattat ttaatatttg ggaaatattc attctaattg gtaatcagat tttagaaaac   1140 aataaacccct tgcatatg                                               1158

<210> SEQ ID NO 64
<211> LENGTH: 20
<212> TYPE: DNA
<213> ORGANISM: Artificial Sequence
<220> FEATURE:
<223> OTHER INFORMATION: primer sll0208up-R

<400> SEQUENCE: 64
gtcaaattcg gtgcggacag                                               20

<210> SEQ ID NO 65
<211> LENGTH: 38
<212> TYPE: DNA
<213> ORGANISM: Artificial Sequence
<220> FEATURE:
<223> OTHER INFORMATION: primer sll0208up/Pcpc560-F

<400> SEQUENCE: 65
```
cgcaccgaat tgacgctttc agcgggcaa ccaacgag                      38

<210> SEQ ID NO 66
<211> LENGTH: 40
<212> TYPE: DNA
<213> ORGANISM: Artificial Sequence
<220> FEATURE:
<223> OTHER INFORMATION: primer Sp/Trbc-R

<400> SEQUENCE: 66
cgaacgaaaa tcgatttccc cacttagata aaaaatccgg                   40

<210> SEQ ID NO 67
<211> LENGTH: 40
<212> TYPE: DNA
<213> ORGANISM: Artificial Sequence
<220> FEATURE:
<223> OTHER INFORMATION: primer Pcpc560-AtFAR1-fw

<400> SEQUENCE: 67
taggagatta attcaatgga atccaattgt gttcaatttc                   40

<210> SEQ ID NO 68
<211> LENGTH: 40
<212> TYPE: DNA
<213> ORGANISM: Artificial Sequence
<220> FEATURE:
<223> OTHER INFORMATION: primer Trbc-AtFAR1-rv

<400> SEQUENCE: 68
tgccaaaact gtaacttatt gtttaagcac atgggtgatg                   40

<210> SEQ ID NO 69
<211> LENGTH: 39
<212> TYPE: DNA
<213> ORGANISM: Artificial Sequence
<220> FEATURE:
<223> OTHER INFORMATION: primer Pcpc560-AtFAR4-fw

<400> SEQUENCE: 69
taggagatta attcaatgga ctccaattgc attcagttc                    39

<210> SEQ ID NO 70
<211> LENGTH: 43
<212> TYPE: DNA
<213> ORGANISM: Artificial Sequence
<220> FEATURE:
<223> OTHER INFORMATION: primer Trbc-AtFAR4-rv

<400> SEQUENCE: 70
tgccaaaact gtaacttatt ttttgagtac ataggtgatg agg               43

<210> SEQ ID NO 71
<211> LENGTH: 36
<212> TYPE: DNA
<213> ORGANISM: Artificial Sequence
<220> FEATURE:
<223> OTHER INFORMATION: primer pUC118/NS1up-F

<400> SEQUENCE: 71
ggatcctcta gagtcaatgc cttctccaag ggcggc                       36

<210> SEQ ID NO 72
<211> LENGTH: 37
<212> TYPE: DNA

```
<213> ORGANISM: Artificial Sequence
<220> FEATURE:
<223> OTHER INFORMATION: primer Kmr/NS1up-R

<400> SEQUENCE: 72
ttcgctgggt ttatccttct ggagcaggaa gatgtcg                               37

<210> SEQ ID NO 73
<211> LENGTH: 798
<212> TYPE: DNA
<213> ORGANISM: Synechocystis elongatus sp. strain PCC7942

<400> SEQUENCE: 73
aatgccttct ccaagggcgg cattcccctg actgttgaag gcgttgccaa tatcaagatt       60 gctgggaag aaccgaccat ccacaacgcg atcgagcggc tgcttggcaa aaaccgtaag      120
gaaatcgagc aaattgccaa ggagaccctc gaaggcaact tgcgtggtgt tttagccagc     180
ctcacgccgg agcagatcaa cgaggacaaa attgcctttg ccaaaagtct gctggaagag    240
gcggaggatg accttgagca gctgggtcaa gtcctcgata cgctgcaagt ccagaacatt    300
tccgatgagg tcggttatct ctcggctagt ggacgcaagc agcgggctga tctgcagcga    360
gatgcccgaa ttgctgaagc cgatgcccag gctgcctctg cgatccaaac ggccgaaaat    420
gacaagatca cggccctgcg tcggatcgat cgcgatgtag cgatcgccca gccgaggcc     480 gagcgccgga ttcaggatgc gttgacgcgg cgcgaagcgg tggtggccga agctgaagcg    540
gacattgcta ccgaagtcgc tcgtagccaa gcagaactcc ctgtgcagca ggagcggatc    600
aaacaggtgc agcagcaact tcaagccgat gtgatcgccc agctgaggc agcttgtaaa     660 cgggcgatcg cggaagcgcg gggggccgcc gcccgtatcg tcgaagatgg aaaagctcaa    720
gcggaaggga cccaacggct ggcggaggct tggcagaccg ctggtgctaa tgcccgcgac    780
atcttcctgc tccagaag                                                    798

<210> SEQ ID NO 74
<211> LENGTH: 36
<212> TYPE: DNA
<213> ORGANISM: Artificial Sequence
<220> FEATURE:
<223> OTHER INFORMATION: primer Kmr/NS1down-F

<400> SEQUENCE: 74
ggaatttgta tcgattcgag tccctgctcg tcacgc                                36

<210> SEQ ID NO 75
<211> LENGTH: 36
<212> TYPE: DNA
<213> ORGANISM: Artificial Sequence
<220> FEATURE:
<223> OTHER INFORMATION: primer pUC118/NS1down-R

<400> SEQUENCE: 75
gcatgcctgc aggtccggca tggcaatgtc tctctg                                36

<210> SEQ ID NO 76
<211> LENGTH: 781
<212> TYPE: DNA
<213> ORGANISM: Synechocystis elongatus sp. strain PCC7942

<400> SEQUENCE: 76
tcgagtccct gctcgtcacg ctttcaggca ccgtgccaga tatcgacgtg gagtcgatca       60
ctgtgattgg cgaaggggaa ggcagcgcta cccaaatcgc tagcttgctg gagaagctga     120
```

-continued

```
aacaaaccac gggcattgat ctggcgaaat ccctaccggg tcaatccgac tcgcccgctg    180
cgaagtccta agagatagcg atgtgaccgc gatcgcttgt caagaatccc agtgatcccg    240
aaccatagga aggcaagctc aatgcttgcc tcgtcttgag gactatctag atgtctgtgg    300
aacgcacatt tattgccatc aagcccgatg gcgttcagcg gggtttggtc ggtacgatca    360
tcggccgctt tgagcaaaaa ggcttcaaac tggtgggcct aaagcagctg aagcccagtc    420
gcgagctggc cgaacagcac tatgctgtcc accgcgagcg ccccttcttc aatggcctcg    480
tcgagttcat cacctctggg ccgatcgtgg cgatcgtctt ggaaggcgaa ggcgttgtgg    540
cggctgctcg caagttgatc ggcgctacca atccgctgac ggcagaaccg ggcaccatcc    600
gtggtgattt tggtgtcaat attggccgca acatcatcca tggctcggat gcaatcgaaa    660
cagcacaaca ggaaattgct ctctggttta gcccagcaga gctaagtgat tggacccca    720 cgattcaacc ctggctgtac gaataaggtc tgcattcctt cagagagaca ttgccatgcc    780
g    781
```

<210> SEQ ID NO 77
<211> LENGTH: 21
<212> TYPE: DNA
<213> ORGANISM: Artificial Sequence
<220> FEATURE:
<223> OTHER INFORMATION: primer NS1down-F

<400> SEQUENCE: 77
tcgagtccct gctcgtcacg c    21

<210> SEQ ID NO 78
<211> LENGTH: 38
<212> TYPE: DNA
<213> ORGANISM: Artificial Sequence
<220> FEATURE:
<223> OTHER INFORMATION: primer Kmr/Ptrc-F

<400> SEQUENCE: 78
ggaatttgta tcgatttgac aattaatcat ccggctcg    38

<210> SEQ ID NO 79
<211> LENGTH: 23
<212> TYPE: DNA
<213> ORGANISM: Artificial Sequence
<220> FEATURE:
<223> OTHER INFORMATION: primer Ptrc-R

<400> SEQUENCE: 79
ggtctgtttc ctgtgtgaaa ttg    23

<210> SEQ ID NO 80
<211> LENGTH: 74
<212> TYPE: DNA
<213> ORGANISM: Artificial Sequence
<220> FEATURE:
<223> OTHER INFORMATION: trc promoter

<400> SEQUENCE: 80
ttgacaatta atcatccggc tcgtataatg tgtggaattg tgagcggata acaatttcac    60
acaggaaaca gacc    74

<210> SEQ ID NO 81
<211> LENGTH: 38
<212> TYPE: DNA

```
<213> ORGANISM: Artificial Sequence
<220> FEATURE:
<223> OTHER INFORMATION: primer NS1down/Trbc-R

<400> SEQUENCE: 81
cgagcaggga ctcgattccc cacttagata aaaaatcc                              38

<210> SEQ ID NO 82
<211> LENGTH: 37
<212> TYPE: DNA
<213> ORGANISM: Artificial Sequence
<220> FEATURE:
<223> OTHER INFORMATION: primer Ptrc/NoKASII(-40)-F

<400> SEQUENCE: 82
cacaggaaac agaccatgac tgtgcgtcgt gcatcag                               37

<210> SEQ ID NO 83
<211> LENGTH: 37
<212> TYPE: DNA
<213> ORGANISM: Artificial Sequence
<220> FEATURE:
<223> OTHER INFORMATION: primer pUC118/orf1593up-F

<400> SEQUENCE: 83
ggatcctcta gagtcttgcc gccaatgtcg atgtagg                               37

<210> SEQ ID NO 84
<211> LENGTH: 38
<212> TYPE: DNA
<213> ORGANISM: Artificial Sequence
<220> FEATURE:
<223> OTHER INFORMATION: primer Sp/orf1593up-R

<400> SEQUENCE: 84
cgaacgaaaa tcgatcgctt tgaaagtcca gttcaagg                              38

<210> SEQ ID NO 85
<211> LENGTH: 1188
<212> TYPE: DNA
<213> ORGANISM: Synechocystis elongatus sp. strain PCC7942

<400> SEQUENCE: 85
ccaatgtcga tgtaggcccc atcggtgctg tattcgcaga ccttgccgcg taccagttgg      60
ccttttgggg aatccagcga ctgggcttcc aaggctaggg caaagtcgtc gtaggaaggg     120
gtgttggcgg cagaaggact catactgttc ggacgatgga ctttcgcaga atgcggttct     180
tcctactttg acactgcatt gcgatcgctc actagcccct gaggagacaa gtcacggcaa     240
tgttgcatgg atccatcccc gccgagcgct tctttcctta cctacgctgg cctgagattg     300
cggcgctacc cgatcgcgat cgcgtcctga tcattcagcc gatcggggcg atcgagcagc     360
acggtccgca tttgccgctg gtagtggata ccgcgatcgc aaccgctgtg accggcgagg     420
cattacgaag attgcctgcc gaaattgctg cctatgccct gccaaccctc tgctacggca     480
aatccaacga acattgccag tttccgggca cgatcagcct gcggacagaa accctgctgg     540
ccgttttgat cgacagcgct cacagcctct atgctgcggg gttccggcga ctgatctggc     600
taaatggcca tgggggggcag ccccaggttt tgcaactcgc ggctcgtgat ctgcgcgaac     660
aatttccagg tttcgaagtt ctgccactgt tcgtctggaa tgtacccaac cagattggtg     720
agctgttgac acctcgcgag cagactttgg gtctccatgc tggcgatgcg aaaccagcc      780 tgatgctgca tctgctgccc gatcaggtgc gaatggatca ggcgatcgcg aatatccgc      840
```

```
cagacttgga tgctgagggt ttgctgagct gggaaggcaa tctgccgatc gcttggctga      900
cccatgacct cagccagagc ggtgtcattg gcgatccaac cccagcaacc gctgcgaaag      960
gggcagaaat ttttgagcaa ttggtgcagg gttgggtgca agtgctgacg gtgatcgccc     1020
actggcagcg atcgtccctg ctgccaccaa agtaaatacc gctagagtgt agattggtgc     1080
gtaccccctg ggatccacca aatcccacat tctccctctc atccgtgtca ggagaccgca     1140
gactcatgcc gcagcttgaa gccagccttg aactggactt tcaaagcg                  1188
```

<210> SEQ ID NO 86
<211> LENGTH: 38
<212> TYPE: DNA
<213> ORGANISM: Artificial Sequence
<220> FEATURE:
<223> OTHER INFORMATION: primer Sp/orf1594down-F

<400> SEQUENCE: 86

```
aaaccttgc atatgatcac gatcgagaag atggaagc                                38
```

<210> SEQ ID NO 87
<211> LENGTH: 37
<212> TYPE: DNA
<213> ORGANISM: Artificial Sequence
<220> FEATURE:
<223> OTHER INFORMATION: primer pUC118/orf1594down-R

<400> SEQUENCE: 87

```
gcatgcctgc aggtcgccag ccatcaggca gtcaagc                                37
```

<210> SEQ ID NO 88
<211> LENGTH: 1197
<212> TYPE: DNA
<213> ORGANISM: Synechocystis elongatus sp. strain PCC7942

<400> SEQUENCE: 88

```
atcacgatcg agaagatgga agcgatcggt gaggcatcgg tgcgccacgg cttccaaccc       60
ttggcattgg caatttgagg tctgtgcatg gctgcacctg tcacgaagaa gccaattctg      120
ctggagtttg aaaagcccct agttgagctg gaggaacgga tcacgcaaat ccgcacccctc    180 gcagcggaca accaggtgga tgtgagcggc caaattcagc aactggaagc ccgggcgatt      240
caactgcggc gagaaatttt tagtaatctc tcgccagccc agcgcatcca agtgcgcgt      300 catccccgac gtccgagtac cttggactac atccaagcga tcagcgacga gtggattgaa      360
ttacacggcg atcgcaacgg tagtgatgac ctcgcactcg tgggtggtgt tggtgcgctc      420
gacggccagc cagtcgtttt cttgggccac caaaagggc gcgacaccaa ggacaacgtg       480
ctgcgcaact tcgggatggc ttcacccgc ggctatcgca aggcactgcg tttgatggag       540
catgccgatc gcttcgggat gccgattctg acctttatcg atacacccgg tgcttacgct      600
ggggtcagtg ctgaagaact gggtcaaggt gaggcaatcg cagtcaacct gcgcgaaatg      660
ttccgcttct cggtgccgat tctctgcaca gtgattggcg aaggcggttc gggcggggcc      720
ttgggcattg gcgtcggcga tcgcctgctg atgtttgagc attccgtcta cactgttgcc      780
agtcccgaag cctgcgcatc aattctctgg cgtgatgcgg gcaaggcagc ccaggcggca      840
gaagcgctca agattacggc gcgagacctc aagcaattag gcatccttga cgaaatcatc      900
accgaacctt tgggcggtgc ccattctgca ccgctggaaa cggcccagag tttgcgtcag      960
gttttgctgc gccatctgaa ggatttgcaa gccctcagtc cggctcagtt gcgcgagcag     1020
```
cgttatcaaa agtttcgcca gctcggggtg tttctggaaa gcagtgacta aacaccgccg    1080
cctggcccaa atggtataat cggatgcgtt acatttcgtc atgtcttggc gaatcttgca    1140
ttcccaggcc gtcacgtctt cggctaaaca tccacgcttg actgcctgat ggctggc       1197

<210> SEQ ID NO 89
<211> LENGTH: 23
<212> TYPE: DNA
<213> ORGANISM: Artificial Sequence
<220> FEATURE:
<223> OTHER INFORMATION: primer orf1594up-R

<400> SEQUENCE: 89
cgctttgaaa gtccagttca agg                                            23

<210> SEQ ID NO 90
<211> LENGTH: 38
<212> TYPE: DNA
<213> ORGANISM: Artificial Sequence
<220> FEATURE:
<223> OTHER INFORMATION: primer orf1593up/Ptrc-F

<400> SEQUENCE: 90
tggactttca aagcgttgac aattaatcat ccggctcg                            38

<210> SEQ ID NO 91
<211> LENGTH: 39
<212> TYPE: DNA
<213> ORGANISM: Artificial Sequence
<220> FEATURE:
<223> OTHER INFORMATION: primer orf1593up/PrrnA-F

<400> SEQUENCE: 91
tggactttca aagcgctccg tctactcttc tgtccatcc                           39

<210> SEQ ID NO 92
<211> LENGTH: 38
<212> TYPE: DNA
<213> ORGANISM: Artificial Sequence
<220> FEATURE:
<223> OTHER INFORMATION: primer PrrnA-R

<400> SEQUENCE: 92
aagggaaaac ctccttggct taattaatct acctaact                            38

<210> SEQ ID NO 93
<211> LENGTH: 102
<212> TYPE: DNA
<213> ORGANISM: Synechocystis elongatus sp. strain PCC7942

<400> SEQUENCE: 93
ctccgtctac tcttctgtcc atcccgaaaa aattttctc tgaggggtt gacgcgacta      60 ggcgagttag gtagattaat taagccaagg aggttttccc tt                       102

<210> SEQ ID NO 94
<211> LENGTH: 40
<212> TYPE: DNA
<213> ORGANISM: Artificial Sequence
<220> FEATURE:
<223> OTHER INFORMATION: primer Ptrc99A2-AtFAR1-F

<400> SEQUENCE: 94
cacaggaaac agaccatgga atccaattgt gttcaatttc                          40

```
<210> SEQ ID NO 95
<211> LENGTH: 39
<212> TYPE: DNA
<213> ORGANISM: Artificial Sequence
<220> FEATURE:
<223> OTHER INFORMATION: primer PrrnA2-AtFAR4-F

<400> SEQUENCE: 95
aggaggtttt cccttatgga ctccaattgc attcagttc                              39

<210> SEQ ID NO 96
<211> LENGTH: 436
<212> TYPE: PRT
<213> ORGANISM: Nannochloropsis oculata

<400> SEQUENCE: 96
```

Met Thr Val Arg Arg Ala Ser Gly Glu Val Ser Met Ala Asp Leu Pro
1               5                   10                  15

Pro Leu Val Arg Lys Arg Val Val Ile Thr Gly Val Gly Ala Val Ser
                20                  25                  30

Pro Leu Gly Trp Gly Asp Asp Phe Trp Asn Gly Leu Val Glu Gly Arg
            35                  40                  45

Ser Gly Ile Val Arg Leu Pro Ser Trp Ala Asp Glu Tyr Pro Ala Arg
    50                  55                  60

Ile Gly Gly Leu Val Pro Asp His Phe Lys Pro Ser Asp Tyr Met Asn
65                  70                  75                  80

Ala Lys Glu Val Lys Arg Gln Ala Arg Phe Thr His Phe Ala Met Ala
                85                  90                  95

Ala Ala Arg Met Ala Val Glu Asp Ala Lys Leu Asp Leu Glu Lys Val
                100                 105                 110

Asp Arg Ser Arg Ala Gly Cys Met Ile Gly Ser Gly Ile Gly Gly Val
                115                 120                 125

Glu Ile Phe Glu Lys Asn Cys Gly Glu Phe Asp Lys Lys Gly Gly Gly
            130                 135                 140

Leu Pro Gly Leu Lys Ala Val Ser Pro Phe Leu Ile Pro Ala Leu Ile
145                 150                 155                 160

Ala Asn Thr Ala Ala Gly Thr Val Ala Ile Glu Leu Gly Leu Lys Gly
                165                 170                 175

Pro Asn Tyr Cys Ser Val Ser Ala Cys Ala Ser Gly Thr His Thr Ile
                180                 185                 190

Gly Asp Ala Phe Phe Phe Leu Gln Asn Gly Met Ala Asp Val Cys Val
            195                 200                 205

Thr Gly Gly Thr Glu Ala Ala Ile Thr Pro Leu Cys Phe Ala Gly Phe
        210                 215                 220

Val Ala Ile Arg Ala Leu Thr Thr Ser Gly Asn Asp Asp Pro Thr Lys
225                 230                 235                 240

Ala Ser Lys Pro Phe Asp Lys Asn Arg Ala Gly Phe Val Met Ala Glu
                245                 250                 255

Gly Ala Gly Met Leu Val Leu Glu Thr Glu Glu His Ala Lys Ala Arg
                260                 265                 270

Gly Ala Thr Ile Tyr Ala Glu Leu Ala Gly Tyr Gly Ala Ser Cys Asp
            275                 280                 285

Ala His His Ile Thr Ala Pro His Pro Glu Gly Glu Gly Leu Ala Asn
        290                 295                 300

Ala Met Asn Met Ala Leu Thr Ser Ala Gly Leu Lys Pro Thr Asp Val
305                 310                 315                 320

```
Asp Tyr Ile Asn Ala His Gly Thr Ser Thr Ala Tyr Asn Asp Lys Phe
                325                 330                 335

Glu Thr Leu Ala Ile His Arg Val Phe Gly Glu His Ala Lys Lys Leu
            340                 345                 350

Lys Val Ser Ser Ile Lys Ser Met Thr Gly His Ser Leu Gly Ala Ala
        355                 360                 365

Gly Ala Phe Glu Ala Val Ala Cys Ala Lys Ala Ile Lys Glu Gly Ile
    370                 375                 380

Ile Pro Pro Thr Ile Asn Tyr Glu Thr Pro Asp Pro Asp Cys Asp Leu
385                 390                 395                 400

Asp Tyr Val Pro Asn Lys Ala Ile Lys His Asp Val Asn Val Ala Ile
                405                 410                 415

Ser Asp Asn Leu Gly Phe Gly Gly His Asn Ala Ala Leu Val Phe Lys
            420                 425                 430

Lys Tyr Val Ala
        435

<210> SEQ ID NO 97
<211> LENGTH: 1311
<212> TYPE: DNA
<213> ORGANISM: Nannochloropsis oculata

<400> SEQUENCE: 97
atgactgtgc gtcgtgcatc aggggaagtg agcatggcgg acttgccccc gcttgtccgc      60
aagagggtgg tgatcacggg tgtcggcgcc gtgtctcctc tcgggtgggg agacgacttc     120
tggaacggtc tcgtggaggg aaggagcggc attgtccgcc tcccttcgtg gcggacgag      180 taccccgcgc gaatcggagg cttggtcccg gatcacttta agccgagcga ctacatgaat     240
gccaaggagt gaaacgaca ggcccgcttc acccattttg ccatggcagc tgcccgtatg      300
gccgtggaag acgccaagct cgacctggag aaggtggacc gctcgcgtgc cgggtgcatg     360
ataggatccg gcattggtgg tgtagaaatc ttcgagaaaa actgtgggga attcgacaag     420
aagggcggag ggctccctgg cctcaaggct gtctccccct tcctgattcc ggccctcatc     480
gccaacaccg cagccgggac agtggctatt gaactcggct tgaagggccc gaactactgc     540
tctgtctccg cctgcgcctc gggcacgcat accatcggtg atgccttctt cttcctccaa     600
aacggcatgg cggacgtttg tgtaacgggc gggacggaag ccgccatcac cccccctctgt    660 tttgcgggat tgtcgccat cgcgcccctt accaccagtg caacgacga ccccaccaag      720 gcctccaagc cgttcgacaa gaaccgagcc ggtttcgtta tggccgaggg agcggggatg     780
ctcgtccttg agacggagga acacgcgaag gcccgaggtg ccaccatcta tgccgagctt     840
gctggctacg gcgcatcctg cgacgcccac acatcaccg cccccatcc cgaaggcgag      900 gggctggcga acgcgatgaa tatggctctg acgtccgccg gcctcaagcc tacggacgtg     960
gactacatta tgcccatgg aaccagcacg gcctacaacg acaaattcga gacgctggcc    1020
attcaccgcg tctttggcga gcacgccaag aagctgaagg tttcttccat caagtcaatg    1080
actggtcact ccctcggggc cgccggtgcc ttcgaggccg tggcgtgcgc gaaggcaatc    1140
aaggagggca tcatcccgcc caccatcaac tacgagactc ccgatccaga ctgcgacttg    1200
gactatgttc ccaacaaggc gatcaagcac gacgtgaatg tggccatctc cgataacctg    1260
ggcttcggcg gcacaacgc ggctttggtc ttcaagaagt atgttgccta g             1311

<210> SEQ ID NO 98
<211> LENGTH: 456
```

<212> TYPE: PRT
<213> ORGANISM: Nannochloropsis oculata

<400> SEQUENCE: 98

Met Pro Ser Ser Phe Phe Leu Arg Gln Thr Ser Ser Val Ser Ser Ser
1               5                   10                  15

Ser Ser Ser Ser Arg Thr Val Arg Arg Ala Ser Gly Glu Val Ser Met
            20                  25                  30

Ala Asp Leu Pro Pro Leu Val Arg Lys Arg Val Val Ile Thr Gly Val
        35                  40                  45

Gly Ala Val Ser Pro Leu Gly Trp Gly Asp Asp Phe Trp Asn Gly Leu
    50                  55                  60

Val Glu Gly Arg Ser Gly Ile Val Arg Leu Pro Ser Trp Ala Asp Glu
65                  70                  75                  80

Tyr Pro Ala Arg Ile Gly Gly Leu Val Pro Asp His Phe Lys Pro Ser
                85                  90                  95

Asp Tyr Met Asn Ala Lys Glu Val Lys Arg Gln Ala Arg Phe Thr His
            100                 105                 110

Phe Ala Met Ala Ala Ala Arg Met Ala Val Glu Asp Ala Lys Leu Asp
        115                 120                 125

Leu Glu Lys Val Asp Arg Ser Arg Ala Gly Cys Met Ile Gly Ser Gly
    130                 135                 140

Ile Gly Gly Val Glu Ile Phe Glu Lys Asn Cys Gly Glu Phe Asp Lys
145                 150                 155                 160

Lys Gly Gly Gly Leu Pro Gly Leu Lys Ala Val Ser Pro Phe Leu Ile
                165                 170                 175

Pro Ala Leu Ile Ala Asn Thr Ala Ala Gly Thr Val Ala Ile Glu Leu
            180                 185                 190

Gly Leu Lys Gly Pro Asn Tyr Cys Ser Val Ser Ala Cys Ala Ser Gly
        195                 200                 205

Thr His Thr Ile Gly Asp Ala Phe Phe Phe Leu Gln Asn Gly Met Ala
    210                 215                 220

Asp Val Cys Val Thr Gly Gly Thr Glu Ala Ala Ile Thr Pro Leu Cys
225                 230                 235                 240

Phe Ala Gly Phe Val Ala Ile Arg Ala Leu Thr Thr Ser Gly Asn Asp
                245                 250                 255

Asp Pro Thr Lys Ala Ser Lys Pro Phe Asp Lys Asn Arg Ala Gly Phe
            260                 265                 270

Val Met Ala Glu Gly Ala Gly Met Leu Val Leu Glu Thr Glu Glu His
        275                 280                 285

Ala Lys Ala Arg Gly Ala Thr Ile Tyr Ala Glu Leu Ala Gly Tyr Gly
    290                 295                 300

Ala Ser Cys Asp Ala His His Ile Thr Ala Pro His Pro Glu Gly Glu
305                 310                 315                 320

Gly Leu Ala Asn Ala Met Asn Met Ala Leu Thr Ser Ala Gly Leu Lys
                325                 330                 335

Pro Thr Asp Val Asp Tyr Ile Asn Ala His Gly Thr Ser Thr Ala Tyr
            340                 345                 350

Asn Asp Lys Phe Glu Thr Leu Ala Ile His Arg Val Phe Gly Glu His
        355                 360                 365

Ala Lys Lys Leu Lys Val Ser Ser Ile Lys Ser Met Thr Gly His Ser
    370                 375                 380

Leu Gly Ala Ala Gly Ala Phe Glu Ala Val Ala Cys Ala Lys Ala Ile
385                 390                 395                 400

Lys Glu Gly Ile Ile Pro Pro Thr Ile Asn Tyr Glu Thr Pro Asp Pro
            405                 410                 415

Asp Cys Asp Leu Asp Tyr Val Pro Asn Lys Ala Ile Lys His Asp Val
        420                 425                 430

Asn Val Ala Ile Ser Asp Asn Leu Gly Phe Gly Gly His Asn Ala Ala
    435                 440                 445

Leu Val Phe Lys Lys Tyr Val Ala
    450                 455

<210> SEQ ID NO 99
<211> LENGTH: 1371
<212> TYPE: DNA
<213> ORGANISM: Nannochloropsis oculata

<400> SEQUENCE: 99

| | | |
|---|---|---|
| atgccctcgt ccttcttcct ccggcagact tcctccgtca gcagcagcag cagcagcagc | 60 |
| aggactgtgc gtcgtgcatc aggggaagtg agcatggcgg acttgccccc gcttgtccgc | 120 |
| aagagggtgg tgatcacggg tgtcggcgcc gtgtctcctc tcgggtgggg agacgacttc | 180 |
| tggaacggtc tcgtggaggg aaggagcggc attgtccgcc tcccttcgtg gcggacgag | 240 |
| taccccgcgc gaatcggagg cttggtcccg gatcacttta agccgagcga ctacatgaat | 300 |
| gccaaggagg tgaaacgaca ggcccgcttc acccatttg ccatggcagc tgcccgtatg | 360 |
| gccgtggaag acgccaagct cgacctggag aaggtggacc gctcgcgtgc cgggtgcatg | 420 |
| ataggatccg gcattggtgg tgtagaaatc ttcgagaaaa actgtgggga attcgacaag | 480 |
| aagggcggag gctccctgg cctcaaggct gtctccccct tcctgattcc ggccctcatc | 540 |
| gccaacaccg cagccgggac agtggctatt gaactcggct tgaagggccc gaactactgc | 600 |
| tctgtctccg cctgcgcctc gggcacgcat accatcggtg atgccttctt cttcctccaa | 660 |
| aacggcatgg cggacgtttg tgtaacgggc gggacggaag ccgccatcac ccccctctgt | 720 |
| tttgcgggat tgtcgccat tcgcgccctt accaccagtg gcaacgacga ccccaccaag | 780 |
| gcctccaagc cgttcgacaa gaaccgagcc ggtttcgtta tggccgaggg agcggggatg | 840 |
| ctcgtccttg agacggagga acacgcgaag gcccgaggtg ccaccatcta tgccgagctt | 900 |
| gctggctacg gcgcatcctg cgacgcccac acatcaccg ccccccatcc cgaaggcgag | 960 |
| gggctggcga acgcgatgaa tatggctctg acgtccgccg gctcaagcc tacgacgtg | 1020 |
| gactacatta tgcccatgg aaccagcacg gcctacaacg acaaattcga cgctggcc | 1080 |
| attaccgcg tctttggcga gcacgccaag aagctgaagg tttcttccat caagtcaatg | 1140 |
| actggtcact ccctcggggc cgccggtgcc ttcgaggccg tggcgtgcgc gaaggcaatc | 1200 |
| aaggagggca tcatcccgcc caccatcaac tacgagactc ccgatccaga ctgcgacttg | 1260 |
| gactatgttc ccaacaaggc gatcaagcac gacgtgaatg tggccatctc cgataacctg | 1320 |
| ggcttcggcg gcacaacgc ggctttggtc ttcaagaagt atgttgccta g | 1371 |

<210> SEQ ID NO 100
<211> LENGTH: 493
<212> TYPE: PRT
<213> ORGANISM: Brassica rapa

<400> SEQUENCE: 100

Met Glu Ser Asn Cys Val Gln Phe Leu Gly Asp Lys Thr Ile Leu Ile
1               5                  10                  15

Thr Gly Ala Pro Gly Phe Leu Ala Lys Val Leu Val Glu Lys Ile Leu

```
            20                  25                  30
Arg Leu Gln Pro Asn Val Lys Lys Met Tyr Leu Leu Arg Ala Ser
            35                  40                  45

Asp Asp Lys Ala Ala Met Gln Arg Leu Arg Ser Glu Val Val Glu Ile
 50                  55                  60

Asp Leu Phe Arg Val Leu Arg Lys Asp Leu Gly Glu Glu Asn Leu Asp
 65                  70                  75                  80

Lys Leu Val His Glu Lys Ile Val Pro Val Pro Gly Asp Ile Ser Val
                     85                  90                  95

His Asn Leu Gly Leu Lys Asp Pro Asp Leu Leu Gln Arg Met Trp Asn
                 100                 105                 110

Glu Ile Asp Ile Ile Ile Asn Ile Ala Ala Thr Thr Asn Phe Asp Glu
                 115                 120                 125

Arg Tyr Asp Ile Gly Leu Gly Ile Asn Thr Phe Gly Ala Leu Asn Val
             130                 135                 140

Leu Asn Phe Ala Lys Lys Cys Val Lys Arg Gln Leu Leu His Val
145                 150                 155                 160

Ser Thr Ala Tyr Val Cys Gly Glu Asn Lys Gly Leu Phe Leu Glu Lys
                 165                 170                 175

Pro Phe Lys Met Gly Glu Ser Leu Ser Gly Asp Lys Lys Leu Asp Ile
             180                 185                 190

Asn Val Glu Phe Glu Leu Met Lys Gln Lys Leu Lys Glu Leu Lys His
             195                 200                 205

Gln Asp Cys Thr Glu Glu Ile Ser Gln Ser Met Lys Asp Leu Gly
         210                 215                 220

Met Thr Arg Ala Lys Leu His Gly Trp Pro Asn Thr Tyr Val Phe Thr
225                 230                 235                 240

Lys Ala Met Gly Glu Met Leu Ile Gly Ser Ser Arg Glu Asn Leu Pro
                 245                 250                 255

Leu Val Ile Ile Arg Pro Thr Met Ile Thr Ser Thr Leu Ala Glu Pro
             260                 265                 270

Phe Pro Gly Trp Ile Glu Gly Leu Arg Thr Ile Asp Ser Val Ile Val
             275                 280                 285

Ala Tyr Gly Lys Gly Arg Leu Lys Cys Phe Leu Ala Asp Ser Thr Ser
             290                 295                 300

Val Phe Asp Leu Ile Pro Ala Asp Met Val Val Asn Ala Met Ile Ala
305                 310                 315                 320

Thr Ala Thr Ala His Ser Gly Glu Thr Gly Ile Gln Thr Ile Tyr His
                 325                 330                 335

Val Gly Ser Ser Phe Gln Asn Pro Val Thr Phe Gly Gln Leu His Asp
             340                 345                 350

Thr Ala Ala Arg Tyr Phe Thr Lys Lys Pro Leu Val Ala Arg Asn Gly
             355                 360                 365

Ser Pro Ile Ile Val Ser Lys Gly Thr Ile Leu Pro Thr Met Ala Gln
         370                 375                 380

Phe Ser Leu Tyr Met Thr Leu Arg Tyr Lys Leu Pro Leu Gln Ile Leu
385                 390                 395                 400

Arg Leu Ile Asn Ile Ile Tyr Pro Trp Ser Glu Gly Asp Lys Tyr Asn
                 405                 410                 415

Asp Leu Ser Arg Lys Leu Lys Leu Ala Met Arg Leu Val Glu Leu Tyr
             420                 425                 430

Glu Pro Tyr Leu Leu Phe Lys Gly Ile Phe Asp Asp Leu Asn Thr Glu
             435                 440                 445
```

```
Arg Leu Arg Ile Arg Arg Lys Glu Asn Ile Lys Glu Met Asp Gly Ser
    450                 455                 460

Phe Glu Phe Asp Pro Lys Ser Ile Asn Trp Asp Asp Tyr Ile Ala Asn
465                 470                 475                 480

Ile His Ile Pro Gly Leu Ile Thr Tyr Val Leu Lys Gln
                485                 490

<210> SEQ ID NO 101
<211> LENGTH: 496
<212> TYPE: PRT
<213> ORGANISM: Brassica rapa

<400> SEQUENCE: 101

Met Glu Phe Asn Cys Val Gln Phe Leu Gln Asn Lys Thr Ile Leu Val
1               5                   10                  15

Thr Gly Ala Thr Gly Phe Leu Ala Lys Val Phe Val Glu Lys Ile Leu
            20                  25                  30

Arg Val Gln Pro Asn Val Lys Lys Leu Tyr Leu Val Val Arg Ala Ser
        35                  40                  45

Asp Ser Glu Ala Ala Met Lys Arg Leu Arg Ala Glu Val Phe Glu Lys
    50                  55                  60

Asp Leu Phe Lys Val Leu Arg Glu Asn Ile Gly Glu Asn Leu Asn
65                  70                  75                  80

Thr Leu Phe Ser Glu Lys Val Val Pro Val Ala Gly Asp Ile Ser Thr
                85                  90                  95

Asp Cys Phe Gly Val Lys Asp Ser Asn Leu Arg Glu Arg Met Gln Lys
            100                 105                 110

Glu Ile Asp Ile Val Val Asn Val Ala Ala Thr Thr Asn Phe Asp Glu
        115                 120                 125

Arg Tyr Asp Val Gly Leu Gly Ile Asn Thr Phe Gly Ala Leu Asn Val
    130                 135                 140

Leu Asn Phe Ala Lys Lys Cys Val Lys Ala Gln Leu Leu Leu His Val
145                 150                 155                 160

Ser Thr Ala Tyr Val Cys Gly Glu Lys Ser Gly Leu Leu Arg Glu Lys
                165                 170                 175

Pro Phe Ala Met Glu Glu Ile Arg Asn Glu Ala Gly His Gln Leu Asp
            180                 185                 190

Ile Asn Phe Glu Met Glu Leu Met Lys Lys Arg Leu Lys Glu Leu His
        195                 200                 205

Asp Gln Asp Cys Ser Asp Glu Asp Ile Thr Leu Ser Met Lys Glu Leu
    210                 215                 220

Gly Met Glu Arg Ala Lys Leu His Gly Trp Pro Asn Thr Tyr Val Phe
225                 230                 235                 240

Thr Lys Ser Met Gly Glu Met Leu Ile Gly Asn His Arg Glu Ser Leu
                245                 250                 255

Pro Leu Val Ile Ile Arg Pro Thr Met Ile Thr Ser Thr Leu Ser Glu
            260                 265                 270

Pro Phe Pro Gly Trp Ile Glu Gly Leu Arg Thr Val Asp Ser Val Ile
        275                 280                 285

Val Ala Tyr Gly Lys Gly Val Leu Lys Cys Phe Leu Val Asp Val Asn
    290                 295                 300

Ser Val Cys Asp Met Ile Pro Val Asp Met Val Ala Asn Ala Met Ile
305                 310                 315                 320

Thr Ala Thr Ala Thr His Ala Gly Gly Ser Gly Val His Met Val Tyr
```

-continued

```
               325                 330                 335
His Val Gly Ser Ser His Gln Asn Pro Val Thr Phe Gly Glu Ile His
            340                 345                 350

Glu Ile Ser Val Arg Tyr Phe Thr Lys Ser Pro Leu Arg Ser Arg Asn
            355                 360                 365

Gly Ser Leu Ile Ala Val Ser Lys Val Arg Leu Ile Ser Thr Met Ala
    370                 375                 380

Leu Phe Ser Leu Tyr Met Thr Leu Arg Phe Lys Leu Pro Leu Gln Leu
385                 390                 395                 400

Leu Lys Leu Ile Asp Ile Ile Tyr Pro Trp Arg Ser Gly Asp Lys Tyr
            405                 410                 415

Gly Asp Lys Asn Arg Lys Ile Asn Met Val Met Arg Leu Val Glu Leu
            420                 425                 430

Tyr Glu Pro Tyr Val Leu Phe Lys Gly Ile Phe Asp Asp Arg Asn Thr
            435                 440                 445

Lys Ser Leu Cys Ala Asn Gln Lys Glu Asp Glu Thr Lys Thr Ser Lys
            450                 455                 460

Gly Ser Met Phe Asp Phe Asp Pro Lys Gly Ile Asn Trp Gly Asp Tyr
465                 470                 475                 480

Leu Thr Ser Val His Ile Pro Gly Leu Ile Thr His Val Leu Lys Lys
                485                 490                 495
```

METHOD OF PRODUCING FATTY ALCOHOL

TECHNICAL FIELD

The present invention relates to a method of producing a fatty alcohol. Further, the present invention also relates to a transformant for use in this method.

BACKGROUND ART

Fatty alcohols are one of main components of lipids, and exist as surface protective substances (cuticle, suberin or the like), and also constitute WAX esters existing as storage lipids in plants.

The fatty alcohols obtained from natural fats and oils by purification or chemical synthesis are widely used as industrial use. For example, the fatty alcohols such as stearyl alcohol (linear saturated fatty alcohol having 18 carbon atoms), eicosanol (linear saturated fatty alcohol having 20 carbon atoms), and behenyl alcohol (linear saturated fatty alcohol having 22 carbon atoms) are used in cosmetics, shampoos, conditioners, lubricating oils and the like as an emulsifying agent or a surfactant.

In synthetic pathway of a fatty acid being a precursor of a fatty alcohol in plants or animals, an elongation reaction of the carbon chain is repeated starting from an acetyl-CoA and a malonyl-acyl carrier protein (hereinafter, also referred to as "ACP"), and finally an acyl-ACP (a composite consisting of an acyl group being a fatty acid residue and an ACP. Here, the number of carbon atoms indicates the number of carbon atoms of the acyl group, and indicates the same hereinafter in several cases) having about 18 carbon atoms is synthesized. A β-ketoacyl-ACP synthase (β-ketoacyl-acyl carrier protein synthase; hereinafter, also referred to as "KAS") is an enzyme involved in elongation of chain length of the acyl group, among enzymes involved in the fatty acid synthetic pathway. In plants, four kinds of KASs having different function respectively, namely KAS I, KAS II, KAS III and KAS IV are known to exist. Among them, KAS II is mainly involved in the elongation reaction to a stearoyl-ACP having 18 carbon atoms.

In the plants, it is known that an acyl-ACP having 16 or 18 carbon atoms, which is synthesized by the fatty acid synthetic pathway, is converted into an acyl-CoA having 16 or 18 carbon atoms by a thioesterase or a long-chain acyl-CoA synthetase, and the resulting materials further undergo the elongation reaction in an endoplasmic reticulum. Then, the acyl-CoA having 20 or more carbon atoms elongated in the endoplasmic reticulum is converted into a long-chain fatty alcohol having 20 or more carbon atoms by a fatty acyl-CoA reductase (hereinafter, referred to as "FAR").

As mentioned above, fatty alcohols are widely used in various applications. Therefore, attempts have been made on improving productivity of the fatty alcohols in vivo by using hosts such as yeast and bacteria. Furthermore, applications and usefulness of the fatty alcohols depend on the number of carbon atoms (chain length). Therefore attempts have been made also on controlling the number of carbon atoms of the fatty alcohols.

In general, it is considered that introduction and reinforcement of FAR are effective in order to provide microorganisms with ability to produce the fatty alcohols to improve productivity of the fatty alcohols. For example, Non-Patent Literatures 1 to 3 disclose methods of synthesizing fatty alcohols by introducing a gene encoding a FAR derived from *Arabidopsis thaliana* into *Escherichia coli* or bacteria. However, in these bacteria having no synthesis pathway of the fatty acid having 20 or more carbon atoms, an acyl-ACP or an acyl-CoA having 18 or less carbon atoms serves as a substrate of FAR in cells. Accordingly, the number of carbon atoms of the fatty alcohols synthesized when only FAR genes are introduced into these bacteria is 18 or less, and the long-chain fatty alcohol having 20 or more carbon atoms cannot be synthesized.

Further, Non-Patent Literature 4 discloses a method of providing ability to produce a long-chain fatty alcohol by introducing a gene encoding a FAR derived from *Arabidopsis thaliana*, for yeast (*Saccharomyces cerevisiae*) which has ability to produce an acyl-CoA having 20 or more carbon atoms, thereinto. However, Non-Patent Literature 4 discloses nothing at all on providing host microorganisms having no ability to synthesize the long-chain fatty acid having 20 or more carbon atoms with ability to synthesize long-chain fatty alcohols.

Patent Literature 1 discloses that a recombinant host cell of *Escherichia coli*, containing a gene encoding a protein such as a KAS and a FAR, produces a fatty alcohol having less than 18 carbon atoms. Patent Literature 2 discloses a method of producing fatty alcohols having 20 or more carbon atoms by using yeast wherein a FAR is expressed.

CITATION LIST

Patent Literatures

Patent Literature 1: WO 2013/152051 A1
Patent Literature 2: WO 2016/159869 A1

Non-Patent Literatures

Non-Patent Literature 1: Journal of Plant Physiology, 2009, vol. 166, p. 787-796
Non-Patent Literature 2: Metabolic Engineering, 2011 vol. 13, p. 169-176
Non-Patent Literature 3: Microbial Cell Factories, 2012, 11:65
Non-Patent Literature 4: Plant Physiology, 2010, vol. 153 (4), p. 1539-1554

SUMMARY OF INVENTION

The present invention relates to a method of producing long-chain fatty alcohols including fatty alcohols having 20 or more carbon atoms, which contains culturing a microorganism wherein expression of a gene encoding at least one kind of 3-ketoacyl-ACP synthase selected from the group consisting of the following proteins (A) to (F), and expression of a gene encoding at least one kind of fatty acyl-CoA reductase selected from the group consisting of the following proteins (G) to (R) are enhanced:
(A) a protein consisting of the amino acid sequence set forth in SEQ ID NO: 1;
(B) a protein consisting of an amino acid sequence having 60% or more identity with the amino acid sequence of the protein (A), and having β-ketoacyl-ACP synthase II activity;
(C) a protein consisting of the amino acid sequence set forth in SEQ ID NO: 96;
(D) a protein consisting of an amino acid sequence having 60% or more identity with the amino acid sequence of the protein (C), and having β-ketoacyl-ACP synthase II activity;
(E) a protein consisting of the amino acid sequence set forth in SEQ ID NO: 98;

(F) a protein consisting of an amino acid sequence having 60% or more identity with the amino acid sequence of the protein (E), and having β-ketoacyl-ACP synthase II activity;
(G) a protein consisting of the amino acid sequence set forth in SEQ ID NO: 3;
(H) a protein consisting of an amino acid sequence having 80% or more identity with the amino acid sequence of the protein (G), and having fatty acyl-CoA reductase activity;
(I) a protein consisting of the amino acid sequence set forth in SEQ ID NO: 5;
(J) a protein consisting of an amino acid sequence having 80% or more identity with the amino acid sequence of the protein (I), and having fatty acyl-CoA reductase activity;
(K) a protein consisting of the amino acid sequence set forth in SEQ ID NO: 7;
(L) a protein consisting of an amino acid sequence having 80% or more identity with the amino acid sequence of the protein (K), and having fatty acyl-CoA reductase activity;
(M) a protein consisting of the amino acid sequence set forth in SEQ ID NO: 9;
(N) a protein consisting of an amino acid sequence having 80% or more identity with the amino acid sequence of the protein (M), and having fatty acyl-CoA reductase activity;
(O) a protein consisting of the amino acid sequence set forth in SEQ ID NO: 100;
(P) a protein consisting of an amino acid sequence having 80% or more identity with the amino acid sequence of the protein (O), and having fatty acyl-CoA reductase activity;
(Q) a protein consisting of the amino acid sequence set forth in SEQ ID NO: 101; and
(R) a protein consisting of an amino acid sequence having 80% or more identity with the amino acid sequence of the protein (Q), and having fatty acyl-CoA reductase activity.

Other and further objects, features and advantages of the invention will appear more fully from the following description, appropriately referring to the accompanying drawings.

DESCRIPTION OF EMBODIMENTS

Figure 1:
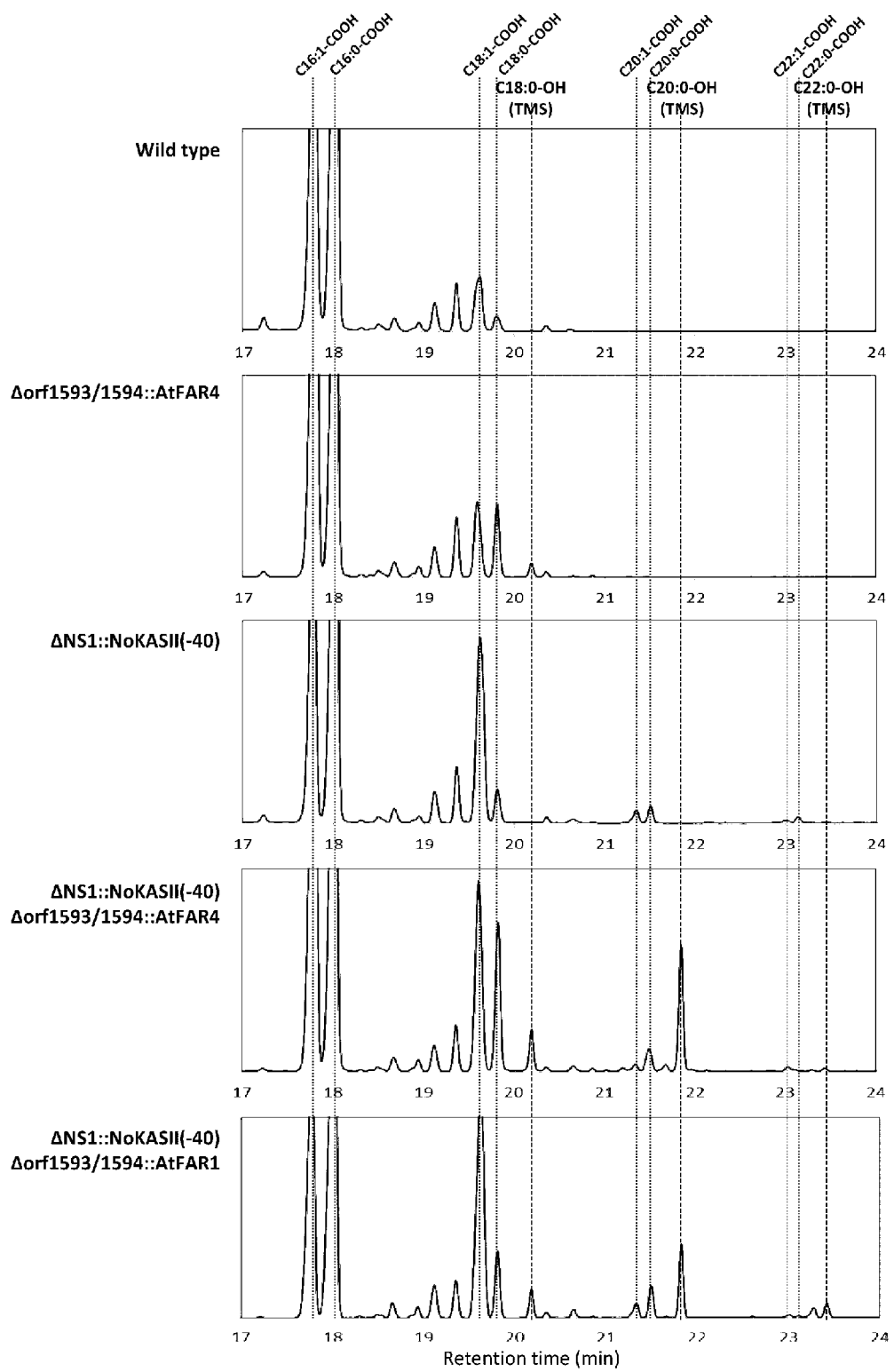
FIG. 1 is a graph showing a result of gas chromatography mass spectrometry analysis of fatty alcohols produced by transformants prepared in Preparation Example 3 in Example.

The present invention relates to providing a method of producing long-chain fatty alcohols, which improves productivity of long-chain fatty alcohols in host microorganisms.

Further, the present invention relates to providing a method of providing ability to produce long-chain fatty alcohols for a host microorganism which has no ability to produce a long-chain fatty alcohol.

Furthermore, the present invention relates to providing a transformant for which ability to produce long-chain fatty alcohol is provided.

The present inventors firstly identified a KAS having function of KAS II as an enzyme involved in synthesis of long-chain fatty acids, from alga belonging to the genus *Nannochloropsis* being one kind of algae. Then, the present inventors found that this protein has ability of synthesizing a fatty acid having 20 or more carbon atoms which is used as a precursor of a long-chain fatty alcohol.

Further, the present inventors focused on a FAR derived from *Arabidopsis thaliana* (hereinafter, also referred to as "AtFAR") and a FAR derived from *Brassica rapa* (hereinafter, also referred to as "BrFAR"), as a FAR which catalyzes a reaction of synthesizing a fatty alcohol by using an acyl-ACP as a substrate.

As a result of enhancing expression of a gene encoding the KAS and a gene encoding the AtFAR or the BrFAR in a cell of a host microorganism, the present inventors found that the host microorganism, which originally has no ability to produce a long-chain fatty acid having 20 or more carbon atoms, acquired the ability to produce a long-chain fatty acid, and further found that the host microorganism acquired ability to produce a long-chain fatty alcohol having 20 or more carbon atoms.

The present invention was completed based on these findings.

According to the method of producing the fatty alcohols of the present invention, the productivity of long-chain fatty alcohols in host microorganisms can be improved.

Further, according to the method of providing ability to produce the long-chain fatty alcohols of the present invention, the ability to produce the same can be provided for a host microorganism originally having no ability to produce a long-chain fatty acid.

Moreover, the transformant of the present invention is excellent in the productivity of long-chain fatty alcohols.

The term "lipid(s)" in the present specification, covers a simple lipid such as a neutral lipid (triacylglycerol, or the like), wax, and a ceramide; a complex lipid such as a phospholipid, a glycolipid, and a sulfolipid; and a derived lipid obtained from the lipid such as a fatty acid (free fatty acid), alcohols, and hydrocarbons.

The fatty acids categorized into the derived lipid generally refer to the fatty acids per se and mean "free fatty acids". In the present invention, a part of the fatty acids or a part of the acyl group in molecules of a simple lipid and a complex lipid is expressed as "fatty acid residue". Then, unless otherwise specified, a term "fatty acid" is used as a generic term for "free fatty acid" and "fatty acid residue".

Further, a term "fatty alcohol composition" in the present specification means a weight proportion of each fatty alcohol relative to the weight of whole fatty alcohols (total fatty alcohols). The weight (production amount) of the fatty alcohols or the fatty alcohol composition can be measured according to the method used in Examples.

In the present specification, the description of "Cx:y" for the fatty alcohol or the acyl group constituting the fatty alcohol means that the number of carbon atoms is "x" and the number of double bonds is "y". The description of "Cx" means a fatty alcohol or an acyl group having "x" as the number of carbon atoms. Further, the description of "Cx:y-COOH" means a fatty acid having "x" as the number of carbon atoms and "y" as the number of double bonds, and the description of "Cx:y-OH" means a fatty alcohol having "x" as the number of carbon atoms and "y" as the number of double bonds.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in this description, the "stringent conditions" includes, for example, the method described in Molecular Cloning—A LABORATORY MANUAL THIRD EDITION [Joseph Sambrook, David W. Russell., Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH7.0), 0.5% SDS, 5×Denhardt and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

The present inventors focused on a KASII derived from an alga belonging to the genus *Nannochloropsis*, and an AtFAR described in Non-Patent Literatures 1 to 4 and a BrFAR whose amino acid sequence is highly identical to the amino acid sequence of the AtFAR. Then, expression of each of the above-described KAS, AtFAR and BrFAR was enhanced in the cells of the host microorganisms to measure a formation amount of the fatty alcohols. As a result, even when the above-described proteins were each independently enhanced, production of the long-chain fatty alcohols was unable to be confirmed.

On the other hand, as shown in Examples mentioned later, a transformant provided with ability to produce the long-chain fatty alcohols can be prepared by enhancing the expression of both the KAS gene and the FAR gene in microorganisms originally have no ability to synthesize long-chain fatty acids having 20 or more carbon atoms, such as *Escherichia coli* and cyanobacteria.

The KAS is an enzyme involved in chain length elongation of acyl group in synthetic pathway of a fatty acid which is a precursor of a fatty alcohol. The KAS is one kind of fatty acid synthetic enzyme which catalyzes the condensation reaction of an acyl-ACP with a malonyl-ACP, and is involved in the synthesis of acyl-ACP. In the fatty acid synthetic pathway, generally, the elongation reaction of the carbon chain is repeated starting from an acetyl-CoA, and finally an acyl-ACP having 16 or 18 carbon atoms is synthesized.

In the first stage of the fatty acid synthesis, an acetoacetyl-ACP is formed by a condensation reaction between the acetyl-CoA and a malonyl-ACP. The KAS catalyzes this reaction. Then, the keto group of the acetoacetyl-ACP is reduced by a β-ketoacyl-ACP reductase, to produce a hydroxybutyryl-ACP. Subsequently, the hydroxybutyryl-ACP is dehydrated by a β-hydroxyacyl-ACP dehydrase, to produce a crotonyl-ACP. Finally, the crotonyl-ACP is reduced by an enoyl-ACP reductase, to produce a butyryl-ACP. The butyryl-ACP in which two carbon atoms are added to the carbon chain of the acyl group of the acetyl-ACP is produced by a series of these reactions. Hereinafter, the similar reactions are repeated to cause elongation of the carbon chain of the acyl-ACP, and an acyl-ACP having 16 or 18 carbon atoms is finally synthesized.

KAS is categorized into KAS I, KAS II, KAS III and KAS IV according to their substrate specificity. KAS III uses an acetyl-CoA having 2 carbon atoms as the substrate to catalyze the elongation reaction that the number of carbon atoms is increased from 2 to 4. KAS I mainly catalyzes the elongation reaction that the number of carbon atoms is increased from 4 to 16, to synthesize the palmitoyl-ACP having 16 carbon atoms. KAS II mainly catalyzes the elongation reaction to the long-chain acyl group having 16 to 18 carbon atoms or more, to synthesize a long-chain acyl-ACP. KAS IV mainly catalyzes the elongation reaction that the acyl-ACP having 6 carbon atoms is converted to the acyl-ACP having 14 carbon atoms, to synthesize a medium-chain acyl-ACP.

KAS that can be preferably used in the present invention is preferably the KAS II which mainly involved in synthesis of long-chain acyl-ACP having 16 or 18 carbon atoms. Specific examples of such KAS II include the following proteins (A) to (F).
(A) a protein consisting of the amino acid sequence set forth in SEQ ID NO: 1;
(B) a protein consisting of an amino acid sequence having 60% or more identity with the amino acid sequence of the protein (A), and having β-ketoacyl-ACP synthase activity (hereinafter, also referred to as "KAS activity");
(C) a protein consisting of the amino acid sequence set forth in SEQ ID NO: 96;
(D) a protein consisting of an amino acid sequence having 60% or more identity with the amino acid sequence of the protein (C), and having KAS activity;
(E) a protein consisting of the amino acid sequence set forth in SEQ ID NO: 98; and
(F) a protein consisting of an amino acid sequence having 60% or more identity with the amino acid sequence of the protein (E), and having KAS activity.

The proteins (A) to (F) (hereinafter, also referred to as "NoKASII") are one kind of KAS, and are involved in synthesis of long-chain fatty acids.

The protein (A) is a KAS derived from *Nannochloropsis oculata* strain NIES-2145 being an alga belonging to the genus *Nannochloropsis*.

Further, according to localization prediction based on ChloroP (http://www.cbs.dtu.dk/services/ChloroP/) or targetP (http://www.cbs.dtu.dk/services/TargetP/), the above-described protein (A) is considered to be a KAS of a chloroplast-localized type and an N-terminal 30 to 40 amino acid residue is considered to be a chloroplast transit signal sequence.

The proteins (A) to (F) described above have the KAS activity. In the present specification, the term "KAS activity" means the activity to catalyze the condensation reaction of the acetyl-CoA or the acyl-ACP with the malonyl-ACP. The KAS activity of the protein can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or in the cultured liquid by an ordinary technique. Alternatively, the KAS activity can be confirmed by introducing a DNA produced by linking a gene encoding the protein to the downstream of a promoter which functions in a host cell, into a host cell, culturing the thus-obtained cell under the conditions suitable for the expression of the introduced gene, purifying the protein, and conducting a chain length elongation reaction using various acyl-ACPs, as substrates.

Further, the proteins (A) to (F) are preferably KASII also having synthetic activity of a long-chain β-ketoacyl-ACP having 18 or more carbon atoms, among KASII-typed KASs which are mainly involved in elongation reaction to long-chain acyl group having 16 to 18 carbon atoms. In addition, in the present specification, the term "long-chain β-ketoacyl-ACP synthetic activity" means catalytic activity of an elongation reaction of synthesis of a long-chain acyl-ACP having 18 or more carbon atoms by applying an acyl-ACP having mainly 16 or more carbon atoms as a substrate.

The synthetic activity of the KAS to the long-chain β-ketoacyl-ACP can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or the cultured liquid by an ordinary technique. Alternatively, the synthetic activity to the long-chain β-ketoacyl-ACP can be confirmed by introducing a DNA produced by linking a gene encoding the protein to the downstream of a promoter which functions in a host cell, into a host cell, culturing the thus-obtained cell under the conditions suitable for the expression of the introduced gene, purifying the protein, and conducting a chain length elongation reaction using various acyl-ACPs, as substrates.

The protein (B) consists of an amino acid sequence having 60% or more identity with the amino acid sequence of the protein (A), and has KAS activity.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the KAS activity is kept and a part of the amino acid sequence is subjected to mutation.

In the protein (B), the identity with the amino acid sequence of the protein (A) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, specific examples of the protein (B) include a protein in which 1 or several (for example 1 or more and 190 or less, preferably 1 or more and 166 or less, more preferably 1 or more and 142 or less, further preferably 1 or more and 118 or less, furthermore preferably 1 or more and 95 or less, furthermore preferably 1 or more and 71 or less, furthermore preferably 1 or more and 47 or less, furthermore preferably 1 or more and 38 or less, furthermore preferably 1 or more and 23 or less, furthermore preferably 1 or more and 9 or less, and furthermore preferably 1 or more and 4 or less) amino acids are deleted, substituted, inserted or added to the amino acid sequence of the protein (A), and having ACP activity.

Further, as the protein (B), it is preferable that the protein consists of an amino acid sequence in which the identity with the amino acid sequence of the protein (A) is 60% or more, the protein has the KAS activity, and from which the chloroplast transit signal sequence is deleted.

Moreover, the protein (B) also preferably includes a protein consisting of an amino acid sequence formed such that a signal peptide engaging in transport or secretion of the protein is added to the amino acid sequence of the protein (A) or (B).

The protein (C) consists of an amino acid sequence of the $41^{st}$ to $475^{th}$ amino acids of the amino acid sequence set forth in SEQ ID NO: 1 and a methionine residue added on the side of the N-terminus. Note that the protein (B) also includes the protein (C). In the protein (C), from the protein consisting of the amino acid sequence set forth in SEQ ID NO: 1, the chloroplast transit signal sequence (the $2^{nd}$ to $40^{th}$ amino acid residues of the amino acid sequence set forth in SEQ ID NO: 1) on the side of the N-terminus is deleted.

In the protein (D), the identity with the amino acid sequence of the protein (C) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, specific examples of the protein (D) include a protein in which 1 or several (for example 1 or more and 174 or less, preferably 1 or more and 152 or less, more preferably 1 or more and 130 or less, further preferably 1 or more and 108 or less, furthermore preferably 1 or more and 87 or less, furthermore preferably 1 or more and 65 or less, furthermore preferably 1 or more and 43 or less, furthermore preferably 1 or more and 34 or less, furthermore preferably 1 or more and 21 or less, furthermore preferably 1 or more and 8 or less, and furthermore preferably 1 or more and 4 or less) amino acids are deleted, substituted, inserted or added to the amino acid sequence of the protein (C).

Moreover, the protein (D) also preferably includes a protein consisting of an amino acid sequence formed such that a signal peptide engaging in transport or secretion of the protein is added to the amino acid sequence of the protein (C) or (D).

The protein (E) consists of an amino acid sequence of the $21^{st}$ to $475^{th}$ amino acids of the amino acid sequence set forth in SEQ ID NO: 1 and a methionine residue added on the side of the N-terminus. Note that the protein (B) also includes the protein (E). In the protein (E), from the protein consisting of the amino acid sequence set forth in SEQ ID NO: 1, the chloroplast transit signal sequence (the $2^{nd}$ to $20^{th}$ amino acid residues of the amino acid sequence set forth in SEQ ID NO: 1) on the side of the N-terminus is deleted.

In the protein (F), the identity with the amino acid sequence of the protein (E) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, specific examples of the protein (F) include a protein in which 1 or several (for example 1 or more and 183 or less, preferably 1 or more and 160 or less, more preferably 1 or more and 137 or less, further preferably 1 or more and 114 or less, furthermore preferably 1 or more and 92 or less, furthermore preferably 1 or more and 69 or less, furthermore preferably 1 or more and 46 or less, furthermore preferably 1 or more and 37 or less, furthermore preferably 1 or more and 23 or less, furthermore preferably 1 or more and 10 or less, and furthermore preferably 1 or more and 5 or less) amino acids are deleted, substituted, inserted or added to the amino acid sequence of the protein (E).

Moreover, the protein (F) also preferably includes a protein consisting of an amino acid sequence formed such that a signal peptide engaging in transport or secretion of the protein is added to the amino acid sequence of the protein (E) or (F).

In the present invention, the KAS is preferably the protein (E) or (F). By using the protein (E) or (F) as a KAS, ability to produce long-chain fatty alcohols in the host microorganisms is further improved.

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SOE-PCR, the ODA method, and the Kunkel method. Further, commercially available kits such as PrimeSTAR Mutagenesis Basal Kit (Takara Bio), Transformer TM Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

The proteins (A) to (F) can be obtained by chemical techniques, genetic engineering techniques or the like that are ordinarily carried out. For example, a natural product-derived protein can be obtained through isolation, purification and the like from *Nannochloropsis oculata*. In addition, the proteins (A) to (F) can be obtained by artificial chemical synthesis based on the amino acid sequence set forth in SEQ ID NO: 1. Alternatively, as recombinant proteins, proteins (A) to (F) may also be produced by gene recombination technologies. In the case of producing a recombinant protein, the 3-ketoacyl-ACP synthase gene described below can be used.

Note that the algae such as *Nannochloropsis oculata* can be obtained from culture collection such as private or public research institutes or the like. For example, *Nannochloropsis oculata* strain NIES-2145 can be obtained from National Institute for Environmental Studies (NIES).

An example of a gene encoding the KAS (preferably, any one of the proteins (A) to (F)) (hereinafter, also referred to as "KAS gene") includes a gene consisting of at least one of the following DNAs (a) to (f) (hereinafter, also referred to as "NoKASII gene").
(a) a DNA consisting of the nucleotide sequence set forth in SEQ ID NO: 2;
(b) a DNA consisting of a nucleotide sequence having 60% or more identity with the nucleotide sequence of the DNA (a), and encoding a protein having KAS activity;
(c) a DNA consisting of the nucleotide sequence set forth in SEQ ID NO: 97;
(d) a DNA consisting of a nucleotide sequence having 60% or more identity with the nucleotide sequence of the DNA (c), and encoding a protein having KAS activity;
(e) a DNA consisting of the nucleotide sequence set forth in SEQ ID NO: 99; and
(f) a DNA consisting of a nucleotide sequence having 60% or more identity with the nucleotide sequence of the DNA (e), and encoding a protein having KAS activity.

The nucleotide sequence set forth in SEQ ID NO: 2 is a nucleotide sequence of a gene encoding a protein consisting of the amino acid sequence set forth in SEQ ID NO: 1 (KAS derived from *Nannochloropsis oculata* strain NIES-2145).

In the DNA (b), the identity with the nucleotide sequence of the DNA (a) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, the DNA (b) is also preferably a DNA in which 1 or several (for example 1 or more and 571 or less, preferably 1 or more and 499 or less, more preferably 1 or more and 428 or less, further preferably 1 or more and 357 or less, further preferably 1 or more and 285 or less, further preferably 1 or more and 214 or less, further preferably 1 or more and 142 or less, further preferably 1 or more and 114 or less, further preferably 1 or more and 71 or less, further preferably 1 or more and 28 or less, and furthermore preferably 1 or more and 14 or less) nucleotides are deleted, substituted, inserted or added to the nucleotide sequence set forth in SEQ ID NO: 2, and encoding the protein (A) or (B) having KAS activity. Furthermore, the DNA (b) is also preferably a DNA capable of hybridizing with a DNA consisting of the nucleotide sequence complementary with the DNA (a) under a stringent condition, and encoding the protein (A) or (B) having KAS activity.

Further, the DNA (b) may be a DNA consisting of a nucleotide sequence in which the identity with the nucleotide sequence of the DNA (a) is 60% or more, and encoding the protein (A) or (B) having KAS activity, and from which the nucleotide sequence encoding the chloroplast transit signal sequence is deleted.

Moreover, the DNA (b) also preferably includes a DNA consisting of a nucleotide sequence encoding such that a signal peptide engaging in transport or secretion of the protein is added to the nucleotide sequence of the DNA (a) or (b).

The DNA (c) consists of a nucleotide sequence of the $121^{st}$ to $1428^{th}$ nucleotides of the nucleotide sequence set forth in SEQ ID NO: 2 and a start codon (ATG) added on the side of the 5' end, and encoding the protein (C) (a protein consisting of the amino acid sequence set forth in SEQ ID NO: 96). Note that the above-described DNA (b) also includes the DNA (c). In the DNA (c), from the DNA consisting of the nucleotide sequence set forth in SEQ ID NO: 2, the nucleotide sequence encoding the chloroplast transit signal sequence (the 4th to $120^{th}$ nucleotides of the nucleotide sequence set forth in SEQ ID NO: 2) is deleted.

In the DNA (d), the identity with the nucleotide sequence of the DNA (c) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, the DNA (d) is also preferably a DNA in which 1 or several (for example 1 or more and 523 or less, preferably 1 or more and 457 or less, more preferably 1 or more and 392 or less, further preferably 1 or more and 327 or less, further preferably 1 or more and 261 or less, further preferably 1 or more and 196 or less, further preferably 1 or more and 130 or less, further preferably 1 or more and 104 or less, further preferably 1 or more and 65 or less, further preferably 1 or more and 26 or less, and furthermore preferably 1 or more and 13 or less) nucleotides are deleted, substituted, inserted or added to the nucleotide sequence of the DNA (c), and encoding the protein (C) or (D) having KAS activity. Furthermore, the DNA (d) is also preferably a DNA capable of hybridizing with a DNA consisting of the nucleotide sequence complementary with the DNA (c) under a stringent condition, and encoding the protein (C) or (D) having KAS activity.

Moreover, the DNA (d) also preferably includes a DNA consisting of a nucleotide sequence encoding such that a signal peptide engaging in transport or secretion of the protein is added to the nucleotide sequence of the DNA (c) or (d).

The DNA (e) consists of a nucleotide sequence of the $61^{st}$ to $1428^{th}$ nucleotides of the nucleotide sequence set forth in SEQ ID NO: 2 and a start codon (ATG) added on the side of the 5' end, and encoding the protein (E) (a protein consisting of the amino acid sequence set forth in SEQ ID NO: 98). Note that the above-described DNA (b) also includes the DNA (e). In the DNA (e), from the DNA consisting of the nucleotide sequence set forth in SEQ ID NO: 2, the nucleotide sequence encoding the chloroplast transit signal sequence (the $4^{th}$ to $60^{th}$ nucleotides of the nucleotide sequence set forth in SEQ ID NO: 2) is deleted.

In the DNA (f), the identity with the nucleotide sequence of the DNA (e) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, the DNA (f) is also preferably a DNA in which 1 or several (for example 1 or more and 549 or less, preferably 1 or more and 480 or less, more preferably 1 or more and 412 or less, further preferably 1 or more and 343 or less, further preferably 1 or more and 275 or less, further preferably 1 or more and 206 or less, further preferably 1 or more and 138 or less, further preferably 1 or more and 110 or less, further preferably 1 or more and 69 or less, further preferably 1 or more and 28 or less, and furthermore preferably 1 or more and 14 or less) nucleotides are deleted, substituted, inserted or added to the nucleotide sequence of the DNA (e), and encoding the protein (E) or (F) having KAS activity. Furthermore, the DNA (f) is also preferably a DNA capable of hybridizing with a DNA consisting of the nucleotide sequence complementary with the DNA (e) under a stringent condition, and encoding the protein (E) or (F) having KAS activity.

Moreover, the DNA (f) may be a DNA consisting of a nucleotide sequence in which a nucleotide sequence encoding a signal peptide engaging in transport or secretion of the protein is added to the nucleotide sequence of the DNA (e) or (f).

In the present invention, the KAS gene is preferably a gene consisting of the DNA (e) or (f). By using a gene consisting of the DNA (e) or (f) as a KAS gene, ability to produce long-chain fatty alcohols in the host microorganisms is further improved.

In the present specification, "FAR" is an enzyme having fatty acyl-CoA reductase activity (hereinafter, also referred to as "FAR activity") which catalyzes a reaction of synthesizing a fatty alcohol by using an acyl-CoA or an acyl-ACP as a substrate. The FAR is also referred to as a fatty acyl reductase or a fatty acid reductase. A plurality of methods of converting an acyl-CoA or an acyl-ACP into a fatty alcohol is known. Among these, in formation of the fatty alcohols through FAR, a fatty alcohol is formed from an acyl-CoA or an acyl-ACP by a monoenzymatic reaction.

It can be confirmed that the protein has the FAR activity by a system using a FAR gene deletion strain, for example. Alternatively, it can also be confirmed by examining synthesis of fatty alcohols by introducing the DNA in which a gene encoding the above-described protein is ligated downstream of a promoter functioning in a host cell, into the FAR gene deletion strain. Alternatively, it can also be confirmed by measuring an increase of fatty alcohol amount according to an ordinary method by preparing the FAR or cell lysate containing the same to react the resultant material with the reaction solution containing fatty acyl-CoA, fatty acyl-ACP or the like.

FAR that is preferred for the present invention is preferably a FAR having substrate specificity to long-chain acyl-CoA or long-chain acyl-ACP. Specific examples of such FAR include the following proteins (G) to (R). The following proteins (G) to (R) all have FAR activity.

(G) a protein consisting of the amino acid sequence set forth in SEQ ID NO: 3;
(H) a protein consisting of an amino acid sequence having 80% or more identity with the amino acid sequence of the protein (G), and having FAR activity;
(I) a protein consisting of the amino acid sequence set forth in SEQ ID NO: 5;
(J) a protein consisting of an amino acid sequence having 80% or more identity with the amino acid sequence of the protein (I), and having FAR activity;
(K) a protein consisting of the amino acid sequence set forth in SEQ ID NO: 7;
(L) a protein consisting of an amino acid sequence having 80% or more identity with the amino acid sequence of the protein (K), and having FAR activity;
(M) a protein consisting of the amino acid sequence set forth in SEQ ID NO: 9;
(N) a protein consisting of an amino acid sequence having 80% or more identity with the amino acid sequence of the protein (M), and having FAR activity;
(O) a protein consisting of the amino acid sequence set forth in SEQ ID NO: 100;
(P) a protein consisting of an amino acid sequence having 80% or more identity with the amino acid sequence of the protein (O), and having FAR activity;
(Q) a protein consisting of the amino acid sequence set forth in SEQ ID NO: 101; and
(R) a protein consisting of an amino acid sequence having 80% or more identity with the amino acid sequence of the protein (Q), and having FAR activity.

A protein consisting of the amino acid sequence set forth in SEQ ID NO: 3 (protein (G); hereinafter, also referred to as "AtFAR1"), a protein consisting of the amino acid sequence set forth in SEQ ID NO: 5 (protein (I); hereinafter, also referred to as "AtFAR3"), a protein consisting of the amino acid sequence set forth in SEQ ID NO: 7 (protein (K); hereinafter, also referred to as "AtFAR4"), and a protein consisting of the amino acid sequence set forth in SEQ ID NO: 9 (protein (M); hereinafter, also referred to as "AtFAR5") are all one kind of FAR derived from *Arabidopsis thaliana*. In the present specification, the above-described FARs derived from *Arabidopsis thaliana* are also referred to as "AtFAR", as a whole.

Both a protein consisting of the amino acid sequence set forth in SEQ ID NO: 100 (protein (O); hereinafter, also referred to as "BrFAR1") and a protein consisting of the amino acid sequence set forth in SEQ ID NO: 101 (protein (Q); hereinafter, also referred to as "BrFAR5") are one kind of FAR derived from *Brassica rapa*. In the present specification, the above-described FARs derived from *Brassica rapa* are also referred to as "BrFAR", as a whole.

In the protein (H), the identity with the amino acid sequence of the protein (G) is preferably 85% or more, more preferably 90% or more, further preferably 92% or more, further preferably 95% or more, further preferably 98% or more, and furthermore preferably 99% or more, in view of FAR activity. Further, specific examples of the protein (H)

include a protein in which 1 or several (for example 1 or more and 99 or less, preferably 1 or more and 74 or less, more preferably 1 or more and 50 or less, further preferably 1 or more and 40 or less, furthermore preferably 1 or more and 25 or less, furthermore preferably 1 or more and 10 or less, and furthermore preferably 1 or more and 5 or less) amino acids are deleted, substituted, inserted or added to the amino acid sequence of the protein (G).

In the protein (J), the identity with the amino acid sequence of the protein (I) is preferably 85% or more, more preferably 90% or more, further preferably 92% or more, further preferably 95% or more, further preferably 98% or more, and furthermore preferably 99% or more, in view of FAR activity. Further, specific examples of the protein (J) include a protein in which 1 or several (for example 1 or more and 99 or less, preferably 1 or more and 74 or less, more preferably 1 or more and 50 or less, further preferably 1 or more and 40 or less, furthermore preferably 1 or more and 25 or less, furthermore preferably 1 or more and 10 or less, and furthermore preferably 1 or more and 5 or less) amino acids are deleted, substituted, inserted or added to the amino acid sequence of the protein (I).

In the protein (L), the identity with the amino acid sequence of the protein (K) is preferably 85% or more, more preferably 90% or more, further preferably 92% or more, further preferably 95% or more, further preferably 98% or more, and furthermore preferably 99% or more, in view of FAR activity. Further, specific examples of the protein (L) include a protein in which 1 or several (for example 1 or more and 99 or less, preferably 1 or more and 74 or less, more preferably 1 or more and 50 or less, further preferably 1 or more and 40 or less, furthermore preferably 1 or more and 25 or less, furthermore preferably 1 or more and 10 or less, and furthermore preferably 1 or more and 5 or less) amino acids are deleted, substituted, inserted or added to the amino acid sequence of the protein (K).

In the protein (N), the identity with the amino acid sequence of the protein (M) is preferably 85% or more, more preferably 90% or more, further preferably 92% or more, further preferably 95% or more, further preferably 98% or more, and furthermore preferably 99% or more, in view of FAR activity. Further, specific examples of the protein (N) include a protein in which 1 or several (for example 1 or more and 100 or less, preferably 1 or more and 75 or less, more preferably 1 or more and 50 or less, further preferably 1 or more and 40 or less, furthermore preferably 1 or more and 25 or less, furthermore preferably 1 or more and 10 or less, and furthermore preferably 1 or more and 5 or less) amino acids are deleted, substituted, inserted or added to the amino acid sequence of the protein (M).

In the protein (P), the identity with the amino acid sequence of the protein (O) is preferably 85% or more, more preferably 90% or more, further preferably 92% or more, further preferably 95% or more, further preferably 98% or more, and furthermore preferably 99% or more, in view of FAR activity. Further, specific examples of the protein (P) include a protein in which 1 or several (for example 1 or more and 99 or less, preferably 1 or more and 74 or less, more preferably 1 or more and 50 or less, further preferably 1 or more and 40 or less, furthermore preferably 1 or more and 25 or less, furthermore preferably 1 or more and 10 or less, and furthermore preferably 1 or more and 5 or less) amino acids are deleted, substituted, inserted or added to the amino acid sequence of the protein (O).

In the protein (R), the identity with the amino acid sequence of the protein (Q) is preferably 85% or more, more preferably 90% or more, further preferably 92% or more, further preferably 95% or more, further preferably 98% or more, and furthermore preferably 99% or more, in view of FAR activity. Further, specific examples of the protein (R) include a protein in which 1 or several (for example 1 or more and 100 or less, preferably 1 or more and 75 or less, more preferably 1 or more and 50 or less, further preferably 1 or more and 40 or less, furthermore preferably 1 or more and 25 or less, furthermore preferably 1 or more and 10 or less, and furthermore preferably 1 or more and 5 or less) amino acids are deleted, substituted, inserted or added to the amino acid sequence of the protein (Q).

A method of introducing the mutation into an amino acid sequence includes the methods described above for the KAS.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the FAR activity is kept and a part of the amino acid sequence is subjected to mutation.

Table 1 collectively shows identities of amino acid sequences among various plant-derived FARs mentioned above, enumerated as FAR genes that can be used in the present invention.

TABLE 1

Identities of amino acid sequences among various FARs

| | AtFAR1 | AtFAR3 | AtFAR4 | AtFAR5 | BrFAR1 | BrFAR5 |
|---|---|---|---|---|---|---|
| AtFAR1 (Protein (G)) | | 52% | 73% | 67% | 85% | 68% |
| AtFAR3 (Protein (I)) | — | | 53% | 50% | 52% | 50% |
| AtFAR4 (Protein (K)) | — | — | | 68% | 74% | 68% |
| AtFAR5 (Protein (M)) | — | — | — | | 69% | 87% |
| BrFAR1 (Protein (O)) | — | — | — | — | | 69% |
| BrFAR5 (Protein (Q)) | — | — | — | — | — | |

The proteins (G) to (R) can be obtained by chemical techniques, genetic engineering techniques or the like that are ordinarily carried out. For example, a natural product-derived protein can be obtained through isolation, purification and the like from *Arabidopsis thaliana* or *Brassica rapa*. In addition, the proteins (G) to (R) can be obtained by artificial chemical synthesis based on the amino acid sequence set forth in SEQ ID NO: 3, 5, 7, 9, 100 or 101. Alternatively, as recombinant proteins, proteins (G) to (R) may also be produced by gene recombination technologies. In the case of producing a recombinant protein, the gene encoding the FAR described below can be used.

An example of the gene encoding the FAR (preferably, any one of the proteins (G) to (R)) (hereinafter, also referred to as "FAR gene") includes a gene consisting of at least one of the following DNAs (g) to (r).

(g) a DNA consisting of the nucleotide sequence set forth in SEQ ID NO: 4;
(h) a DNA consisting of a nucleotide sequence having 80% or more identity with the nucleotide sequence of the DNA (g), and encoding a protein having FAR activity;
(i) a DNA consisting of the nucleotide sequence set forth in SEQ ID NO: 6;
(j) a DNA consisting of a nucleotide sequence having 80% or more identity with the nucleotide sequence of the DNA (i), and encoding a protein having FAR activity;
(k) a DNA consisting of the nucleotide sequence set forth in SEQ ID NO: 8;
(l) a DNA consisting of a nucleotide sequence having 80% or more identity with the nucleotide sequence of the DNA (k), and encoding a protein having FAR activity;
(m) a DNA consisting of the nucleotide sequence set forth in SEQ ID NO: 10;
(n) a DNA consisting of a nucleotide sequence having 80% or more identity with the nucleotide sequence of the DNA (m), and encoding a protein having FAR activity;
(o) a DNA consisting of the nucleotide sequence set forth in SEQ ID NO: 35;
(p) a DNA consisting of a nucleotide sequence having 80% or more identity with the nucleotide sequence of the DNA (o), and encoding a protein having FAR activity;
(q) a DNA consisting of the nucleotide sequence set forth in SEQ ID NO: 36; and
(r) a DNA consisting of a nucleotide sequence having 80% or more identity with the nucleotide sequence of the DNA (q), and encoding a protein having FAR activity.

The nucleotide sequence set forth in SEQ ID NO: 4 is a nucleotide sequence of a gene (hereinafter, also referred to as "AtFAR1 gene") encoding the protein (AtFAR1) consisting of the amino acid sequence set forth in SEQ ID NO: 3.

The nucleotide sequence set forth in SEQ ID NO: 6 is a nucleotide sequence of a gene (hereinafter, also referred to as "AtFAR3 gene") encoding the protein (AtFAR3) consisting of the amino acid sequence set forth in SEQ ID NO: 5.

The nucleotide sequence set forth in SEQ ID NO: 8 is a nucleotide sequence of a gene (hereinafter, also referred to as "AtFAR4 gene") encoding the protein (AtFAR4) consisting of the amino acid sequence set forth in SEQ ID NO: 7.

The nucleotide sequence set forth in SEQ ID NO: 10 is a nucleotide sequence of a gene (hereinafter, also referred to as "AtFAR5 gene") encoding the protein (AtFAR5) consisting of the amino acid sequence set forth in SEQ ID NO: 9.

The nucleotide sequence set forth in SEQ ID NO: 35 is a nucleotide sequence of a gene (hereinafter, also referred to as "BrFAR1 gene") encoding the protein (BrFAR1) consisting of the amino acid sequence set forth in SEQ ID NO: 100.

The nucleotide sequence set forth in SEQ ID NO: 36 is a nucleotide sequence of a gene (hereinafter, also referred to as "BrFAR5 gene") encoding the protein (BrFAR5) consisting of the amino acid sequence set forth in SEQ ID NO: 101.

In the DNA (h), the identity with the nucleotide sequence of the DNA (g) is preferably 85% or more, more preferably 90% or more, further preferably 92% or more, further preferably 95% or more, further preferably 98% or more, and furthermore preferably 99% or more, in view of FAR activity.

Further, the DNA (h) is also preferably a DNA in which 1 or several (for example 1 or more and 296 or less, preferably 1 or more and 222 or less, more preferably 1 or more and 148 or less, further preferably 1 or more and 119 or less, further preferably 1 or more and 74 or less, further preferably 1 or more and 30 or less, and furthermore preferably 1 or more and 15 or less) nucleotides are deleted, substituted, inserted or added to the nucleotide sequence of the DNA (g), and encoding a protein having FAR activity.

Furthermore, the DNA (h) is also preferably a DNA capable of hybridizing with a DNA consisting of the nucleotide sequence complementary with the DNA (g) under a stringent condition, and encoding a protein having FAR activity.

In the DNA (j), the identity with the nucleotide sequence of the DNA (i) is preferably 85% or more, more preferably 90% or more, further preferably 92% or more, further preferably 95% or more, further preferably 98% or more, and furthermore preferably 99% or more, in view of FAR activity.

Further, the DNA (j) is also preferably a DNA in which 1 or several (for example 1 or more and 297 or less, preferably 1 or more and 223 or less, more preferably 1 or more and 149 or less, further preferably 1 or more and 119 or less, further preferably 1 or more and 75 or less, further preferably 1 or more and 30 or less, and furthermore preferably 1 or more and 15 or less) nucleotides are deleted, substituted, inserted or added to the nucleotide sequence of the DNA (i), and encoding a protein having FAR activity.

Furthermore, the DNA (j) is also preferably a DNA capable of hybridizing with a DNA consisting of the nucleotide sequence complementary with the DNA (i) under a stringent condition, and encoding a protein having FAR activity.

In the DNA (l), the identity with the nucleotide sequence of the DNA (k) is preferably 85% or more, more preferably 90% or more, further preferably 92% or more, further preferably 95% or more, further preferably 98% or more, and furthermore preferably 99% or more, in view of FAR activity.

Further, the DNA (l) is also preferably a DNA in which 1 or several (for example 1 or more and 297 or less, preferably 1 or more and 223 or less, more preferably 1 or more and 149 or less, further preferably 1 or more and 119 or less, further preferably 1 or more and 75 or less, further preferably 1 or more and 30 or less, and furthermore preferably 1 or more and 15 or less) nucleotides are deleted, substituted, inserted or added to the nucleotide sequence of the DNA (k), and encoding a protein having FAR activity.

Furthermore, the DNA (l) is also preferably a DNA capable of hybridizing with a DNA consisting of the nucleotide sequence complementary with the DNA (k) under a stringent condition, and encoding a protein having FAR activity.

In the DNA (n), the identity with the nucleotide sequence of the DNA (m) is preferably 85% or more, more preferably 90% or more, further preferably 92% or more, further preferably 95% or more, further preferably 98% or more, and furthermore preferably 99% or more, in view of FAR activity.

Further, the DNA (n) is also preferably a DNA in which 1 or several (for example 1 or more and 299 or less, preferably 1 or more and 224 or less, more preferably 1 or more and 150 or less, further preferably 1 or more and 120 or less, further preferably 1 or more and 75 or less, further preferably 1 or more and 30 or less, and furthermore preferably 1 or more and 15 or less) nucleotides are deleted, substituted, inserted or added to the nucleotide sequence of the DNA (m), and encoding a protein having FAR activity.

Furthermore, the DNA (n) is also preferably a DNA capable of hybridizing with a DNA consisting of the nucleotide sequence complementary with the DNA (m) under a stringent condition, and encoding a protein having FAR activity.

In the DNA (p), the identity with the nucleotide sequence of the DNA (o) is preferably 85% or more, more preferably 90% or more, further preferably 92% or more, further preferably 95% or more, further preferably 98% or more, and furthermore preferably 99% or more, in view of FAR activity.

Further, the DNA (p) is also preferably a DNA in which 1 or several (for example 1 or more and 297 or less, preferably 1 or more and 223 or less, more preferably 1 or more and 149 or less, further preferably 1 or more and 119 or less, further preferably 1 or more and 75 or less, further preferably 1 or more and 30 or less, and furthermore preferably 1 or more and 15 or less) nucleotides are deleted, substituted, inserted or added to the nucleotide sequence of the DNA (o), and encoding a protein having FAR activity.

Furthermore, the DNA (p) is also preferably a DNA capable of hybridizing with a DNA consisting of the nucleotide sequence complementary with the DNA (o) under a stringent condition, and encoding a protein having FAR activity.

In the DNA (r), the identity with the nucleotide sequence of the DNA (q) is preferably 85% or more, more preferably 90% or more, further preferably 92% or more, further preferably 95% or more, further preferably 98% or more, and furthermore preferably 99% or more, in view of FAR activity.

Further, the DNA (r) is also preferably a DNA in which 1 or several (for example 1 or more and 299 or less, preferably 1 or more and 225 or less, more preferably 1 or more and 150 or less, further preferably 1 or more and 120 or less, further preferably 1 or more and 75 or less, further preferably 1 or more and 30 or less, and furthermore preferably 1 or more and 15 or less) nucleotides are deleted, substituted, inserted or added to the nucleotide sequence of the DNA (q), and encoding a protein having FAR activity.

Furthermore, the DNA (r) is also preferably a DNA capable of hybridizing with a DNA consisting of the nucleotide sequence complementary with the DNA (q) under a stringent condition, and encoding a protein having FAR activity.

Table 2 collectively shows identities of nucleotide sequences among various FAR genes mentioned above, enumerated as FAR genes that can be used in the present invention.

genome, can be selected. Especially, the method of introducing the KAS gene and the FAR gene into a host microorganism to enhance both the KAS gene and the FAR gene expression is preferable. The host for transformant of the present invention may be a host which does not have ability of producing a long-chain fatty acid having 20 or more carbon atoms.

Hereinafter, in the present specification, a cell in which expression of a gene encoding a target protein herein is enhanced is also referred to as the "transformant", and a cell in which the expression of the gene encoding the target protein is not enhanced is also referred to as the "host" or "wild type strain".

The transformant of the present invention in which expression of the KAS gene and the FAR gene are enhanced is excellent in the productivity of long-chain fatty alcohols. Further, in the transformant of the present invention, the productivity of long-chain fatty alcohols (a production amount of long-chain fatty alcohols or a proportion of long-chain fatty alcohols in the total fatty alcohols to be produced) is tend to increase, in comparison with a host. In addition, even a host originally having no ability to produce a long-chain fatty alcohol acquires the ability to produce the long-chain fatty alcohol. In addition, in the present specification, the term "long-chain fatty alcohol" means a fatty alcohol in which acyl group, that constitutes the fatty alcohol, has 20 or more carbon atoms, preferably 20, 22, 24 or 26 carbon atoms, more preferably 20 or 22 carbon atoms.

Among the transformants of the present invention, a transformant in which expression of the KAS gene and FAR gene are enhanced can be preferably applied to production of long-chain fatty alcohols having 20 or more carbon atoms, more preferably long-chain fatty alcohols having 20 to 26 carbon atoms, further preferably saturated long-chain fatty alcohols or mono-unsaturated long-chain fatty alcohols having 20 to 26 carbon atoms, and further preferably saturated long-chain fatty alcohols or mono-unsaturated long-chain fatty alcohols having 20 or 22 carbon atoms.

The productivity of fatty alcohols in the host and the transformant can be measured by the method used in Examples described below.

The method of introducing the KAS gene and the FAR gene into a host microorganism to enhance the expression of the genes is described.

The KAS gene and the FAR gene can be obtained by genetic engineering techniques that are ordinarily carried out. For example, the KAS gene can be artificially synthesized based on the amino acid sequence set forth in SEQ ID

TABLE 2

Identities of nucleotide sequences among various FAR genes

| | AtFAR1 | AtFAR3 | AtFAR4 | AtFAR5 | BrFAR1 | BrFAR5 |
|---|---|---|---|---|---|---|
| AtFAR1 (DNA (g)) | | 59% | 76% | 71% | 86% | 72% |
| AtFAR3 (DNA (i)) | — | | 60% | 58% | 59% | 58% |
| AtFAR4 (DNA (k)) | — | — | | 74% | 75% | 74% |
| AtFAR5 (DNA (m)) | — | — | — | | 73% | 88% |
| BrFAR1 (DNA (o)) | — | — | — | — | | 72% |
| BrFAR5 (DNA (q)) | — | — | — | — | — | |

A method of enhancing the expression of the KAS gene and the FAR gene can be appropriately selected from an ordinarily method. For example, a method of introducing the KAS gene and the FAR gene into a host microorganism, and a method of modifying expression regulation regions of the gene (promoter, terminator, or the like) in a host microorganism having the KAS gene and the FAR gene on a NO: 1, 96 or 98, or the nucleotide sequence set forth in SEQ ID NO: 2, 97 or 99. Similar to that, the FAR gene can be artificially synthesized based on the amino acid sequence set forth in SEQ ID NO: 3, 5, 7, 9, 100 or 101, or the nucleotide sequence set forth in SEQ ID NO: 4, 6, 8, 10, 35 or 36.

The synthesis of the KAS gene and the FAR gene can be achieved by utilizing, for example, the services of Invitrogen. Further, the gene can also be obtained by cloning from *Nannochloropsis oculata, Arabidopsis thaliana* and *Brassica rapa*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. In addition, depending on the type of the host to be used, a part of the nucleotide sequence of the genes may be optimized. For example, GeneArt Gene Synthesis service from Thermo Fisher Scientific can be used therefor.

*Nannochloropsis oculata* NIES-2145 used in Examples can be obtained from National Institute for Environmental Studies (NIES).

Each the KAS gene and the FAR gene used for the present invention may be used alone or in combination with two or more kinds thereof.

The transformant that can be preferably used in the present invention is obtained by introducing the KAS gene and the FAR gene into a host according to an ordinarily method. Specifically, the transformant can be produced by preparing a recombinant vector or a gene expression cassette which is capable of expressing the KAS gene and the FAR gene in a host cell, introducing this vector or cassette into a host cell, and thereby transforming the host cell.

The host microorganism for the transformant can be appropriately selected from ordinarily used hosts.

As the microorganisms, prokaryotes and eukaryotes can be used, and microorganisms belonging to the genus *Escherichia*, microorganisms belonging to the genus *Bacillus*, prokaryotes such as cyanobacteria (blue-green bacteria), and eukaryotic microorganisms such as yeast and filamentous fungi or the like can be used. Among these, prokaryotes are preferred, microorganisms belonging to the genus *Escherichia* or cyanobacteria are more preferred, and *Escherichia coli* or cyanobacteria are further preferred.

Cyanobacteria which are preferably used as the host of the transformants of the present invention are one group of prokaryotes that perform photosynthesis using chlorophyll, and have an ability to produce oxygen through photosynthesis and fix carbon dioxide. More than billion years ago, cyanobacteria were engulfed by eukaryotic cells. Such intracellular symbiont (primary symbiosis), cyanobacteria, are considered as an origin of chloroplasts. Thus cyanobacteria have been widely used in photosynthesis studies as an ancestor organism of chloroplasts. Further, cyanobacteria grow faster than other plants, and have high photosynthetic ability. Furthermore, cyanobacteria also have a transformation ability.

Cyanobacteria are highly diversified. In view of cell morphology, there are bacteria having a unicellular shape such as *Synechocystis* sp. PCC6803, bacteria having a filamentous shape formed of many cells connected like a string such as *Anabaena* sp. PCC7120 forming heterocysts and fixing nitrogen, bacteria having a spiral shape and a branched shape, and the like.

In view of growth environment, there are species adapted in various conditions including thermophilic bacteria such as *Thermosynechococcus elongatus* BP-1 isolated from Beppu Onsen; and oceanic bacteria such as *Synechococcus* sp. CC9311 living in the coast or *Synechococcus* sp. WH8102 living in the outer sea.

As bacteria having feature intrinsic to the species, *Microcystis aeruginosa*, which has gas vacuoles and can produce toxin; *Gloeobacter violaceus* PCC7421 having no thylakoid and a light harvesting antenna, i.e., phycobilisome, bound to plasma membrane; and oceanic *Acaryochloris marina* having chlorophyll d as a main (>95%) photosynthetic pigment in place of chlorophyll a, as is in general photosynthetic organisms, are also mentioned.

In cyanobacteria, carbon dioxide fixed by photosynthesis is converted into acetyl-CoA via a large number of enzymatic reaction processes. In the initial stage of fatty acid synthesis, malonyl-CoA is synthesized from acetyl-CoA and carbon dioxide by the function of acetyl-CoA carboxylase. Next, malonyl-CoA is converted into malonyl-ACP by the function of malonyl-CoA:ACP transacylase. Thereafter, while β-ketoacyl-ACP synthase progressively works, two carbon units are sequentially added to synthesize acyl-ACP, which are increased in two carbons and used as an intermediate for synthesizing e.g., a membrane lipid.

Every kind of cyanobacteria can be used as the host of the transformant of the present invention. Specific examples of the cyanobacteria include cyanobacteria of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*. Among these, cyanobacteria of the genus *Synechocystis*, the genus *Synechococcus*, the genus *Thermosynechococcus*, or the genus *Anabaena* are preferable, and cyanobacteria of the genus *Synechocystis* or the genus *Synechococcus* are more preferable. Further, the host used in the present invention is preferably *Synechocystis* sp. PCC6803, *Synechocystis* sp. PCC7509, *Synechocystis* sp. PCC6714, *Synechococcus elongatus* sp. PCC7942, *Thermosynechococcus elongatus* BP-1, *Trichodesmium erythraeum* IMS101, *Acaryochloris mariana* MBIC11017, *Crocosphaera watsonii* WH8501, or *Anabaena* sp. PCC7120, more preferably *Synechocystis* sp. PCC6803 or *Synechococcus elongatus* sp. PCC7942.

A vector for use as the plasmid vector for gene expression or a vector containing the gene expression cassette (plasmid) may be any vector capable of introducing the gene encoding the objective protein into a host, and expressing the gene in the host cell. For example, a vector which has expression regulation regions such as a promoter and a terminator in accordance with the type of the host to be introduced, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the expression vector that can be preferably used in the present invention include pBluescript (pBS) II SK(−) (manufactured by Stratagene), a pSTV-based vector (manufactured by Takara Bio), a pUC-based vector (manufactured by Takara Bio), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (Mckenzie, T. et al., 1986, Plasmid 15(2), p. 93-103), pBR322 (manufactured by Takara Bio), pRS403 (manufactured by Stratagene), pMW218/219 (manufactured by Nippon Gene), a pRI-based vector (manufactured by Takara Bio), a pBI-based vector (manufactured by Clontech), and an IN3-based vector (manufactured by Inplanta Innovations).

Moreover, a kind of promoter regulating the expression of the gene encoding an objective protein introduced into the expression vector can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), a promoter of rrnA operon gene encoding Rubisco operon (rbc), PSI reaction center protein (psaAB), D1 protein of PSII (psbA), c-phycocyanin β subunit (cpcB) and ribosomal RNA, cauliflower mosaic virus 35S RNA promoter, promoters for housekeeping genes (e.g., tubulin promoter, actin promoter and ubiquitin promoter), *Brassica napus* or *Brassica raga*-derived Napin gene promoter, plant-derived Rubisco promoter, a promoter of a violaxanthin/(chlorophyll a)-binding protein gene derived from the genus *Nannochloropsis* (VCP1 promoter, VCP2 promoter) (Oliver Kilian, et al., Proceedings of the National Academy of Sciences of the United States of America, 2011, vol. 108(52)), and a promoter of an oleosin-like protein LDSP (lipid droplet surface protein) gene derived from the genus *Nannochloropsis* (Astrid Vieler, et al., PLOS Genetics, 2012; 8(11): e1003064. doi: 10.1371).

Moreover, a kind of selection marker for confirming introduction of the gene encoding a target protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, a gentamicin resistance gene, and a hygromycin resistance gene. Further, it is also possible to use a deletion of an auxotrophy-related gene or the like as the selection marker gene.

Introduction of the gene encoding an objective protein to the vector can be conducted by an ordinary technique such as restriction enzyme treatment and ligation.

Further, the gene to be introduced is preferably optimized in codon in accordance with use frequency of codon in the host microorganism. Information of codons used in each of organisms is available from Codon Usage Database (www.kazusa.or.jp/codon/).

The method for transformation can be appropriately selected from ordinary techniques according to a kind of the host to be used. Examples of the method for transformation include a spontaneous transformation method, a transformation method of using calcium ion, a general competent cell transformation method, a protoplast transformation method, an electroporation method, an LP transformation method, a method of using *Agrobacterium*, a particle gun method, and the like.

In a case where cyanobacteria are used as host microorganisms, the KAS gene and the FAR gene introduced into the cyanobacteria are preferably incorporated into the genome of cyanobacteria by homologous recombination or the like. Positions into which the KAS gene and the FAR gene are incorporated into the genome can be appropriately set.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR method using a genome as a template or the like.

In a host having the KAS gene and the FAR gene on a genome, a method of modifying expression regulation regions of the genes and enhancing the expression of the genes is described.

The "expression regulation region" indicates the promoter or the terminator, in which these sequences are generally involved in regulation of the expression amount (transcription amount, translation amount) of the gene adjacent thereto. In a host having the above-described gene on a genome, productivity of long-chain fatty alcohols can be improved by modifying expression regulation regions of the genes and enhancing the expression of the genes.

Specific examples of the method of modifying the expression regulation regions include interchange of promoters. In the host having the various genes on the genome, the expression of the various genes can be enhanced by interchanging the promoter of the gene with a promoter having higher transcriptional activity.

The above-described modification of a promoter can employ according to an ordinarily method such as homologous recombination. Specifically, a linear DNA fragment containing upstream and downstream regions of a target promoter and containing other promoter instead of the target promoter is constructed, and the resultant DNA fragment is incorporated into a host cell to cause double crossover homologous recombination on the side upstream and downstream of the target promoter of the host genome. As a result, the target promoter on the genome is substituted with other promoter fragment, and the promoter can be modified. The method of modifying a target promoter according to such homologous recombination can be conducted with, for example, referring to literature such as Besher et al., Methods in molecular biology, 1995, vol. 47, p. 291-302.

In the transformant of the present invention, productivity of long-chain fatty alcohols is improved in comparison with the host in which the expression of the KAS gene and the FAR gene are not enhanced. In addition, even in a case where a host microorganism originally has no ability to produce a long-chain fatty alcohol having 20 or more carbon atoms, the host microorganism acquires the ability to produce the long-chain fatty alcohol by enhancing expression of both the KAS gene and the FAR gene.

Accordingly, if the transformant of the present invention is cultured under suitable conditions and then the long-chain fatty alcohols are collected from an obtained cultured product, the long-chain fatty alcohols can be efficiently produced. Herein, the term "cultured product" means liquid medium and a transformant subjected to cultivation.

The culture condition of the transformant of the present invention can be appropriately selected in accordance with the type of the host, and any ordinary used culture condition for the host can be employed. In addition, from a view point of synthetic efficiency of long-chain fatty alcohols, for example, precursor substances involved in long-chain fatty alcohol biosynthesis system may be added to the medium.

For example, in the case of using *Escherichia coli* as a host microorganism, culturing of *Escherichia coli* may be carried out in LB medium or Overnight Express Instant TB Medium (Novagen) at 30 to 37° C. for half a day to 3 days.

In a case where cyanobacteria are used as a host microorganism, culturing thereof may be carried out, according to liquid culture or a modified method thereof, by using a medium to be ordinarily used for culturing of cyanobacteria, such as a BG-11 medium (J. Gen. Microbiol., 1979, vol. 111, p. 1-61), an A medium (Proc. Natl. Acad. Sci. U.S.A., 1980, vol. 77, p. 6052-6056) and an AA medium (Plant Physiol., 1955, vol. 30, p. 366-372). The culture period may be a period during which bacterial cells are sufficiently grown to accumulate fatty acids in high concentrations, for example, from 7 to 45 days, preferably from 7 to 30 days, and more preferably from 10 to 14 days, by an aeration/spinner culture or shaking culture.

A method of collecting the long-chain fatty alcohols from the cultured product is appropriately selected from an ordinary method. For example, the long-chain fatty alcohols can be isolated and collected from the above-described cultured product or growth product by means of filtration, centrifugation, cell disruption, gel filtration chromatography, ion exchange chromatography, chloroform/methanol extraction, hexane extraction, ethanol extraction, or the like. In the case of carrying out the larger scale culturing, the long-chain fatty alcohols can be obtained by collecting oil components from the cultured product or growth product through pressing or extraction, and then performing general purification processes such as degumming, deacidification, decoloration, dewaxing, and deodorization.

From viewpoints of simplification and ease of a collection step of the fatty alcohols produced by the transformant, it is preferable to secrete the fatty alcohols produced by the transformant extracellularly to be allowed to exist in the medium. Alternatively, it is preferable to separate, according to an ordinary method, the microorganisms from at least a part of the medium containing the fatty alcohols after culturing.

The amount of the long-chain fatty alcohols in the amount of the total fatty alcohols produced by the transformant of the present invention is preferably 1% or more, more preferably 2% or more, more preferably 5% or more, and more preferably 10% or more, with respect to the weight of the total fatty alcohols. The upper limit thereof is not particularly limited, but it is preferably 99% or less, and more preferably 95% or less.

The long-chain fatty alcohol obtained by the production method of the present invention can be utilized, as an emulsifier or a surfactant, for cosmetic products, shampoo, conditioner, lubricating oil or the like.

With regard to the embodiments described above, the present invention also discloses methods of producing fatty alcohols, method of providing ability to produce long-chain fatty alcohols, proteins, genes, transformants, methods of producing a transformant, described below.

<1> A method of producing a long-chain fatty alcohol, which contains culturing a microorganism wherein expression of a KAS and a FAS, or a KAS gene and a FAR gene are enhanced.

<2> A method of providing ability to produce a long-chain fatty alcohol for a microorganism (preferably, a microorganism which originally has no ability to produce a long-chain fatty alcohol), which contains enhancing expression of a KAS and a FAR, or a KAS gene and a FAR gene in a cell of the microorganism.

<3> The method described in the above item <1> or <2>, wherein the expression of the KAS gene and the FAR gene in a cell of the microorganism are enhanced to enhance the expression of the KAS and the FAR.

<4> The method described in any one of the above items <1> to <3>, wherein the KAS gene and the FAR gene are introduced into the microorganism, to enhance the expression of the KAS and the FAR introduced therein.

<5> A method of producing a long-chain fatty alcohol including a fatty alcohol having 20 or more carbon atoms, containing the steps of:
culturing a microorganism into which at least one kind of KAS gene selected from the group consisting of the proteins (A) to (F) and at least one kind of FAR gene selected from the group consisting of the proteins (G) to (R) are introduced; and
separating solution containing fatty alcohols including long-chain fatty alcohols form media.

<6> The method described in any one of the above items <1> to <5>, wherein the KAS is a KAS II mainly involved in synthesizing a long-chain acyl-ACP having 16 or 18 carbon atoms.

<7> The method described in any one of the above items <1> to <6>, wherein the KAS is at least one kind of protein selected from the group consisting of the following proteins (A) to (F), preferably at least one kind of protein selected from the group consisting of the following protein (E) and (F):

(A) a protein consisting of the amino acid sequence set forth in SEQ ID NO: 1;
(B) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (A), and having KAS activity;
(C) a protein consisting of the amino acid sequence set forth in SEQ ID NO: 96;
(D) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (C), and having KAS activity;
(E) a protein consisting of the amino acid sequence set forth in SEQ ID NO: 98; and
(F) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (E), and having KAS activity.

<8> The method described in the above item <7>, wherein the protein (B) consists of an amino acid sequence in which 1 or several, preferably 1 or more and 190 or less, more preferably 1 or more and 166 or less, further preferably 1 or more and 142 or less, furthermore preferably 1 or more and 118 or less, furthermore preferably 1 or more and 95 or less, furthermore preferably 1 or more and 71 or less, furthermore preferably 1 or more and 47 or less, furthermore preferably 1 or more and 38 or less, furthermore preferably 1 or more and 23 or less, furthermore preferably 1 or more and 9 or less, and furthermore preferably 1 or more and 4 or less amino acids are deleted, substituted, inserted or added to the amino acid sequence of the protein (A).

<9> The method described in the above item <7>, wherein the protein (D) consists of an amino acid sequence in which 1 or several, preferably 1 or more and 174 or less, more preferably 1 or more and 152 or less, further preferably 1 or more and 130 or less, furthermore preferably 1 or more and 108 or less, furthermore preferably 1 or more and 87 or less, furthermore preferably 1 or more and 65 or less, furthermore preferably 1 or more and 43 or less, furthermore preferably 1 or more and 34 or less, furthermore preferably 1 or more and 21 or less, furthermore preferably 1 or more and 8 or less, and furthermore preferably 1 or more and 4 or less amino acids are deleted, substituted, inserted or added to the amino acid sequence of the protein (C).

<10> The method described in the above item <7>, wherein the protein (F) consists of an amino acid sequence in which 1 or several, preferably 1 or more and 183 or less, more preferably 1 or more and 160 or less, further preferably 1 or more and 137 or less, furthermore preferably 1 or more and 114 or less, furthermore preferably 1 or more and 92 or less, furthermore preferably 1 or more and 69 or less, furthermore preferably 1 or more and 46 or less, furthermore preferably 1 or more and 37 or less, furthermore preferably 1 or more and 23 or less, furthermore preferably 1 or more and 10 or less, and furthermore preferably 1 or more and 5 or less amino acids are deleted, substituted, inserted or added to the amino acid sequence of the protein (E).

<11> The method described in any one of the above items <7> to <10>, wherein the proteins (A) to (F) are a KAS having long-chain β-ketoacyl-ACP synthase activity (activity of catalyzing an elongation reaction of a long-chain acyl-ACP having 18 or more carbon atoms by mainly using an acyl-ACP having 16 or more carbon atoms).

<12> The method described in any one of the above items <1> to <11>, wherein the gene encoding the KAS, preferably encoding any one of the proteins (A) to (F) is a gene consisting of at least one kind of DNA selected from the group consisting of the following DNAs (a) to (f), preferably a gene consisting of at least one kind of DNA selected from the group consisting of the following DNAs (e) and (f):

(a) a DNA consisting of the nucleotide sequence set forth in SEQ ID NO: 2;
(b) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence of the DNA (a), and encoding a protein having KAS activity;
(c) a DNA consisting of the nucleotide sequence set forth in SEQ ID NO: 97;
(d) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence of the DNA (c), and encoding a protein having KAS activity;
(e) a DNA consisting of the nucleotide sequence set forth in SEQ ID NO: 99; and
(f) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence of the DNA (e), and encoding a protein having KAS activity.

<13> The method described in the above item <12>, wherein the DNA (b) is a DNA consisting of a nucleotide sequence in which 1 or several, preferably 1 or more and 571 or less, more preferably 1 or more and 499 or less, further preferably 1 or more and 428 or less, furthermore preferably 1 or more and 357 or less, furthermore preferably 1 or more and 285 or less, furthermore preferably 1 or more and 214 or less, furthermore preferably 1 or more and 142 or less, furthermore preferably 1 or more and 114 or less, furthermore preferably 1 or more and 71 or less, furthermore preferably 1 or more and 28 or less, and furthermore preferably 1 or more and 14 or less nucleotides, are deleted, substituted, inserted or added to the nucleotide sequence of the DNA (a), and encoding the protein (A) or (B) having KAS activity, or a DNA capable of hybridizing with a DNA consisting of the nucleotide sequence complementary with the DNA (a) under a stringent condition, and encoding the protein (A) or (B) having KAS activity.

<14> The method described in the above item <12>, wherein the DNA (d) is a DNA consisting of a nucleotide sequence in which 1 or several, preferably 1 or more and 523 or less, more preferably 1 or more and 457 or less, further preferably 1 or more and 392 or less, furthermore preferably 1 or more and 327 or less, furthermore preferably 1 or more and 261 or less, furthermore preferably 1 or more and 196 or less, furthermore preferably 1 or more and 130 or less, furthermore preferably 1 or more and 104 or less, furthermore preferably 1 or more and 65 or less, furthermore preferably 1 or more and 26 or less, and furthermore preferably 1 or more and 13 or less nucleotides, are deleted, substituted, inserted or added to the nucleotide sequence of the DNA (c), and encoding the protein (C) or (D) having KAS activity, or a DNA capable of hybridizing with a DNA consisting of the nucleotide sequence complementary with the DNA (c) under a stringent condition, and encoding the protein (C) or (D) having KAS activity.

<15> The method described in the above item <12>, wherein the DNA (f) is a DNA consisting of a nucleotide sequence in which 1 or several, preferably 1 or more and 549 or less, more preferably 1 or more and 480 or less, further preferably 1 or more and 412 or less, furthermore preferably 1 or more and 343 or less, furthermore preferably 1 or more and 275 or less, furthermore preferably 1 or more and 206 or less, furthermore preferably 1 or more and 138 or less, furthermore preferably 1 or more and 110 or less, furthermore preferably 1 or more and 69 or less, furthermore preferably 1 or more and 28 or less, and furthermore preferably 1 or more and 14 or less nucleotides, are deleted, substituted, inserted or added to the nucleotide sequence of the DNA (e), and encoding the protein (E) or (F) having KAS activity, or a DNA capable of hybridizing with a DNA consisting of the nucleotide sequence complementary with the DNA (e) under a stringent condition, and encoding the protein (E) or (F) having KAS activity.

<16> The method described in any one of the above items <1> to <15>, wherein the FAR is at least one kind of protein selected from the group consisting of the following proteins (G) to (R):

(G) a protein consisting of the amino acid sequence set forth in SEQ ID NO: 3;
(H) a protein consisting of an amino acid sequence having 80% or more, preferably 85% or more, more preferably 90% or more, more preferably 92% or more, more preferably 95% or more, more preferably 98% or more, and further preferably 99% or more identity with the amino acid sequence of the protein (G), and having FAR activity;
(I) a protein consisting of the amino acid sequence set forth in SEQ ID NO: 5;
(J) a protein consisting of an amino acid sequence having 80% or more, preferably 85% or more, more preferably 90% or more, more preferably 92% or more, more preferably 95% or more, more preferably 98% or more, and further preferably 99% or more identity with the amino acid sequence of the protein (I), and having FAR activity;
(K) a protein consisting of the amino acid sequence set forth in SEQ ID NO: 7;
(L) a protein consisting of an amino acid sequence having 80% or more, preferably 85% or more, more preferably 90% or more, more preferably 92% or more, more preferably 95% or more, more preferably 98% or more, and further preferably 99% or more identity with the amino acid sequence of the protein (K), and having FAR activity;
(M) a protein consisting of the amino acid sequence set forth in SEQ ID NO: 9;
(N) a protein consisting of an amino acid sequence having 80% or more, preferably 85% or more, more preferably 90% or more, more preferably 92% or more, more preferably 95% or more, more preferably 98% or more, and further preferably 99% or more identity with the amino acid sequence of the protein (M), and having FAR activity;
(O) a protein consisting of the amino acid sequence set forth in SEQ ID NO: 100;
(P) a protein consisting of an amino acid sequence having 80% or more, preferably 85% or more, more preferably 90% or more, more preferably 92% or more, more preferably 95% or more, more preferably 98% or more, and further preferably 99% or more identity with the amino acid sequence of the protein (O), and having FAR activity;
(Q) a protein consisting of the amino acid sequence set forth in SEQ ID NO: 101; and
(R) a protein consisting of an amino acid sequence having 80% or more, preferably 85% or more, more preferably 90% or more, more preferably 92% or more, more preferably 95% or more, more preferably 98% or more, and further preferably 99% or more identity with the amino acid sequence of the protein (Q), and having FAR activity.
<17> The method described in the above item <16>, wherein the protein (H) consists of an amino acid sequence in which 1 or several, preferably 1 or more and 99 or less, more preferably 1 or more and 74 or less, further preferably 1 or more and 50 or less, furthermore preferably 1 or more and 40 or less, furthermore preferably 1 or more and 25 or less, furthermore preferably 1 or more and 10 or less, and furthermore preferably 1 or more and 5 or less amino acids are deleted, substituted, inserted or added to the amino acid sequence of the protein (G).
<18> The method described in the above item <16>, wherein the protein (J) consists of an amino acid sequence in which 1 or several, preferably 1 or more and 99 or less, more preferably 1 or more and 74 or less, further preferably 1 or more and 50 or less, furthermore preferably 1 or more and 40 or less, furthermore preferably 1 or more and 25 or less, furthermore preferably 1 or more and 10 or less, and furthermore preferably 1 or more and 5 or less amino acids are deleted, substituted, inserted or added to the amino acid sequence of the protein (I).
<19> The method described in the above item <16>, wherein the protein (L) consists of an amino acid sequence in which 1 or several, preferably 1 or more and 99 or less, more preferably 1 or more and 74 or less, further preferably 1 or more and 50 or less, furthermore preferably 1 or more and 40 or less, furthermore preferably 1 or more and 25 or less, furthermore preferably 1 or more and 10 or less, and furthermore preferably 1 or more and 5 or less amino acids are deleted, substituted, inserted or added to the amino acid sequence of the protein (K).
<20> The method described in the above item <16>, wherein the protein (N) consists of an amino acid sequence in which 1 or several, preferably 1 or more and 100 or less, more preferably 1 or more and 75 or less, further preferably 1 or more and 50 or less, furthermore preferably 1 or more and 40 or less, furthermore preferably 1 or more and 25 or less, furthermore preferably 1 or more and 10 or less, and furthermore preferably 1 or more and 5 or less amino acids are deleted, substituted, inserted or added to the amino acid sequence of the protein (M).
<21> The method described in the above item <16>, wherein the protein (P) consists of an amino acid sequence in which 1 or several, preferably 1 or more and 99 or less, more preferably 1 or more and 74 or less, further preferably 1 or more and 50 or less, furthermore preferably 1 or more and 40 or less, furthermore preferably 1 or more and 25 or less, furthermore preferably 1 or more and 10 or less, and furthermore preferably 1 or more and 5 or less amino acids are deleted, substituted, inserted or added to the amino acid sequence of the protein (O).
<22> The method described in the above item <16>, wherein the protein (R) consists of an amino acid sequence in which 1 or several, preferably 1 or more and 100 or less, more preferably 1 or more and 75 or less, further preferably 1 or more and 50 or less, furthermore preferably 1 or more and 40 or less, furthermore preferably 1 or more and 25 or less, furthermore preferably 1 or more and 10 or less, and furthermore preferably 1 or more and 5 or less amino acids are deleted, substituted, inserted or added to the amino acid sequence of the protein (Q).
<23> The method described in any one of the above items <1> to <22>, wherein the gene encoding the FAR, preferably encoding any one of the proteins (G) to (R) is a gene consisting of at least one kind of DNA selected from the group consisting of the following DNAs (g) to (r):
(g) a DNA consisting of the nucleotide sequence set forth in SEQ ID NO: 4;
(h) a DNA consisting of a nucleotide sequence having 80% or more, preferably 85% or more, more preferably 90% or more, further preferably 92% or more, furthermore preferably 95% or more, furthermore preferably 98% or more, and furthermore preferably 99% or more identity with the nucleotide sequence of the DNA (g), and encoding a protein having FAR activity;
(i) a DNA consisting of the nucleotide sequence set forth in SEQ ID NO: 6;
(j) a DNA consisting of a nucleotide sequence having 80% or more, preferably 85% or more, more preferably 90% or more, further preferably 92% or more, furthermore preferably 95% or more, furthermore preferably 98% or more, and furthermore preferably 99% or more identity with the nucleotide sequence of the DNA (i), and encoding a protein having FAR activity;
(k) a DNA consisting of the nucleotide sequence set forth in SEQ ID NO: 8;
(l) a DNA consisting of a nucleotide sequence having 80% or more, preferably 85% or more, more preferably 90% or more, further preferably 92% or more, furthermore preferably 95% or more, furthermore preferably 98% or more, and furthermore preferably 99% or more identity with the nucleotide sequence of the DNA (k), and encoding a protein having FAR activity;
(m) a DNA consisting of the nucleotide sequence set forth in SEQ ID NO: 10;
(n) a DNA consisting of a nucleotide sequence having 80% or more, preferably 85% or more, more preferably 90% or more, further preferably 92% or more, furthermore preferably 95% or more, furthermore preferably 98% or more, and furthermore preferably 99% or more identity with the nucleotide sequence of the DNA (m), and encoding a protein having FAR activity;
(o) a DNA consisting of the nucleotide sequence set forth in SEQ ID NO: 35;
(p) a DNA consisting of a nucleotide sequence having 80% or more, preferably 85% or more, more preferably 90% or more, further preferably 92% or more, furthermore preferably 95% or more, furthermore preferably 98% or more, and furthermore preferably 99% or more identity with the nucleotide sequence of the DNA (o), and encoding a protein having FAR activity;
(q) a DNA consisting of the nucleotide sequence set forth in SEQ ID NO: 36; and
(r) a DNA consisting of a nucleotide sequence having 80% or more, preferably 85% or more, more preferably 90% or more, further preferably 92% or more, furthermore preferably 95% or more, furthermore preferably 98% or more, and furthermore preferably 99% or more identity with the nucleotide sequence of the DNA (q), and encoding a protein having FAR activity;
<24> The method described in the above item <23>, wherein the DNA (h) is a DNA consisting of a nucleotide sequence in which 1 or several, preferably 1 or more and 296 or less, more preferably 1 or more and 222 or less, further preferably 1 or more and 148 or less, furthermore preferably 1 or more and 119 or less, furthermore preferably 1 or more and 74 or less, furthermore preferably 1 or more and 30 or less, and furthermore preferably 1 or more and 15 or less nucleotides, are deleted, substituted, inserted or added to the nucleotide sequence of the DNA (g), and encoding a protein having FAR activity, or a DNA capable of hybridizing with a DNA consisting of the nucleotide sequence complementary with the DNA (g) under a stringent condition, and encoding a protein having FAR activity.
<25> The method described in the above item <23>, wherein the DNA (j) is a DNA consisting of a nucleotide sequence in which 1 or several, preferably 1 or more and 297 or less, more preferably 1 or more and 223 or less, further preferably 1 or more and 149 or less, furthermore preferably 1 or more and 119 or less, furthermore preferably 1 or more and 75 or less, furthermore preferably 1 or more and 30 or less, and furthermore preferably 1 or more and 15 or less nucleotides, are deleted, substituted, inserted or added to the nucleotide sequence of the DNA (i), and encoding a protein having FAR activity, or a DNA capable of hybridizing with a DNA consisting of the nucleotide sequence complementary with the DNA (i) under a stringent condition, and encoding a protein having FAR activity.
<26> The method described in the above item <23>, wherein the DNA (I) is a DNA consisting of a nucleotide sequence in which 1 or several, preferably 1 or more and 297 or less, more preferably 1 or more and 223 or less, further preferably 1 or more and 149 or less, furthermore preferably 1 or more and 119 or less, furthermore preferably 1 or more and 75 or less, furthermore preferably 1 or more and 30 or less, and furthermore preferably 1 or more and 15 or less nucleotides, are deleted, substituted, inserted or added to the nucleotide sequence of the DNA (k), and encoding a protein having FAR activity, or a DNA capable of hybridizing with a DNA consisting of the nucleotide sequence complementary with the DNA (k) under a stringent condition, and encoding a protein having FAR activity.
<27> The method described in the above item <23>, wherein the DNA (n) is a DNA consisting of a nucleotide sequence in which 1 or several, preferably 1 or more and 299 or less, more preferably 1 or more and 224 or less, further preferably 1 or more and 150 or less, furthermore preferably 1 or more and 120 or less, furthermore preferably 1 or more and 75 or less, furthermore preferably 1 or more and 30 or less, and furthermore preferably 1 or more and 15 or less nucleotides, are deleted, substituted, inserted or added to the nucleotide sequence of the DNA (m), and encoding a protein having FAR activity, or a DNA capable of hybridizing with a DNA consisting of the nucleotide sequence complementary with the DNA (m) under a stringent condition, and encoding a protein having FAR activity.
<28> The method described in the above item <23>, wherein the DNA (p) is a DNA consisting of a nucleotide sequence in which 1 or several, preferably 1 or more and 297 or less, more preferably 1 or more and 223 or less, further preferably 1 or more and 149 or less, furthermore preferably 1 or more and 119 or less, furthermore preferably 1 or more and 75 or less, furthermore preferably 1 or more and 30 or less, and furthermore preferably 1 or more and 15 or less nucleotides, are deleted, substituted, inserted or added to the nucleotide sequence of the DNA (o), and encoding a protein having FAR activity, or a DNA capable of hybridizing with a DNA consisting of the nucleotide sequence complementary with the DNA (o) under a stringent condition, and encoding a protein having FAR activity.
<29> The method described in the above item <23>, wherein the DNA (r) is a DNA consisting of a nucleotide sequence in which 1 or several, preferably 1 or more and 299 or less, more preferably 1 or more and 225 or less, further preferably 1 or more and 150 or less, furthermore preferably 1 or more and 120 or less, furthermore preferably 1 or more and 75 or less, furthermore preferably 1 or more and 30 or less, and furthermore preferably 1 or more and 15 or less nucleotides, are deleted, substituted, inserted or added to the nucleotide sequence of the DNA (q), and encoding a protein having FAR activity, or a DNA capable of hybridizing with a DNA consisting of the nucleotide sequence complementary with the DNA (q) under a stringent condition, and encoding a protein having FAR activity.
<30> The method of producing a long-chain fatty alcohol described in any one of the above items <1> to <29>, wherein a host of the microorganism is a microorganism which has no ability to produce a long-chain fatty alcohol having 20 or more carbon atoms.
<31> The method described in any one of the above items <1> or <30>, wherein the microorganism is prokaryote, and preferably *Escherichia coli* or cyanobacteria.
<32> The method described in the above item <31>, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*, preferably cyanobacteria of the genus *Synechocystis* or the genus *Synechococcus*.
<33> The method described in the above item <31> or <32>, wherein the KAS gene and the FAR gene are incorporated into the genome of cyanobacteria to enhance expression of the genes.
<34> The method described in any one of the above items <1> or <33>, wherein the long-chain fatty alcohol is a long-chain fatty alcohol having 20 or more carbon atoms, preferably a long-chain fatty alcohol having 20 to 26 carbon atoms, more preferably a saturated long-chain fatty alcohol or a mono-unsaturated long-chain fatty alcohol having 20 to 26 carbon atoms, more preferably a saturated long-chain fatty alcohol or mono-unsaturated long-chain fatty alcohol having 20 or 22 carbon atoms.

<35> The method described in any one of the above items <1> or <34>, wherein the amount of the long-chain fatty alcohols in the amount of the total fatty alcohols produced by the microorganism is 1% or more, preferably 2% or more, more preferably 5% or more, and more preferably 10% or more, and 99% or less, and preferably 95% or less, with respect to the weight of the total fatty alcohols.

<36> The method of producing a long-chain fatty alcohol described in any one of the above items <1> to <35>, wherein the long-chain fatty alcohol after culturing exists in an extracellular medium.

<37> The method of producing a long-chain fatty alcohol described in the above item <36>, which contains the step of separating the microorganism from at least a part of the medium containing the fatty alcohols after culturing.

<38> The method of producing a long-chain fatty alcohol described in any one of the above items <1> to <37>, wherein the amount of the long-chain fatty alcohols having 20 or more carbon atoms in the amount of the total fatty alcohols produced by the microorganism is 1% or more with respect to the weight of the total fatty alcohols.

<39> A transformant of a microorganism, wherein expression of the KAS and the FAR, or the KAS gene and the FAR gene are enhanced.

<40> The transformant described in the above item <39>, wherein expression of the KAS gene and the FAR gene are enhanced in a cell of the microorganism, and expression of the KAS and the FAR are enhanced.

<41> A transformant of a microorganism, containing a KAS gene or a recombinant vector containing the same and a FAR gene, or a KAS gene or a recombinant vector containing the same.

<42> A method of preparing a transformant, which contains introducing the KAS gene and the FAR gene, or a recombinant vector containing the KAS gene and a recombinant vector containing the FAR gene into a host microorganism.

<43> The transformant or the method or preparing the same described in any one of the above items <39> to <42>, wherein the KAS is at least one kind of protein selected form the group consisting of the proteins (A) to (F) specified in the above items <7> to <11>, preferably at least one kind of protein selected from the group consisting of the proteins (E) and (F).

<44> The transformant or the method or preparing the same described in any one of the above items <39> to <43>, wherein the KAS gene, preferably a gene encoding at least one kind of protein selected from the group consisting of the proteins (A) to (F) is a gene consisting of at least one kind of DNA selected form the group consisting of the DNAs (a) to (f) specified in the above items <12> to <15>, preferably a gene consisting of at least one kind of DNA selected from the group consisting of the DNAs (e) and (f).

<45> The transformant or the method or preparing the same described in any one of the above items <39> to <44>, wherein the FAR is at least one kind of protein selected form the group consisting of the proteins (G) to (R) specified in the above items <16> to <22>.

<46> The transformant or the method or preparing the same described in any one of the above items <39> to <45>, wherein the FAR gene, preferably a gene encoding at least one kind of protein selected from the group consisting of the proteins (G) to (R) is a gene consisting of at least one kind of DNA selected form the group consisting of the DNAs (g) to (r) specified in the above items <23> to <29>.

<47> The transformant or the method or preparing the same described in any one of the above items <39> to <46>, wherein a host of the microorganism is a microorganism which has no ability to produce a long-chain fatty alcohol having 20 or more carbon atoms.

<48> The transformant or the method or preparing the same described in any one of the above items <39> to <47>, wherein the microorganism is prokaryote, and preferably *Escherichia coli* or cyanobacteria.

<49> The transformant or the method of producing the same described in the above item <48>, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*, preferably cyanobacteria of the genus *Synechocystis* or the genus *Synechococcus*.

<50> Use of the transformant or a transformant obtained by the method of producing a transformant described in any one of the above items <39> to <49>, for producing a long-chain fatty alcohol.

<51> The use described in the above item <50>, wherein the long-chain fatty alcohol is a long-chain fatty alcohol having 20 or more carbon atoms, preferably a long-chain fatty alcohol having 20 to 26 carbon atoms, more preferably a saturated long-chain fatty alcohol or a mono-unsaturated long-chain fatty alcohol having 20 to 26 carbon atoms, and further preferably a saturated long-chain fatty alcohol or mono-unsaturated long-chain fatty alcohol having 20 or 22 carbon atoms.

<52> The proteins (G) to (R) specified in any one of the above items <16> to <22>.

<53> A gene encoding the protein described in the above item <52>.

<54> A gene consisting of at least one kind of DNA selected from the group consisting of the DNA (g) to (r) specified in any one of the above items <23> to <29>.

<55> A recombinant vector containing the gene described in the above item <53> or <54>.

EXAMPLES

Hereinafter, the present invention will be described more in detail with reference to Examples, but the present invention is not limited thereto. Herein, the nucleotide sequences of the primers used in Examples are shown in Tables 3 to 5.

TABLE 3

| SEQ ID NO: | Primer | Nucleotide sequence (5'→3') |
|---|---|---|
| 11 | pBS-SK-fw | GCGTTAATATTTTGTTAAAATTCGC |
| 12 | pBS-SK-rv | CTCTAGAGCGGCCGCCACCGCGG |
| 13 | pBS/NoKASII(-ATG)-fw | GCGGCCGCTCTAGAGGAGAAGCTGACCCTCGCAGTGG |
| 14 | pBS/NoKASII-rv | ACAAAATATTAACGCCTAGGCAACATACTTCTTGAAGACC |
| 15 | pBS/NoKASII(-20)-fw | GCGGCCGCTCTAGAGCCCTCGTCCTTCTTCCTCCGGC |

TABLE 3-continued

| SEQ ID NO: | Primer | Nucleotide sequence (5'→3') |
|---|---|---|
| 16 | pBS/NoKASII(-40)-fw | GCGGCCGCTCTAGAGACTGTGCGTCGTGCATCAGG |
| 17 | pBS/NoKASII(-60)-fw | GCGGCCGCTCTAGAGAGGGTGGTGATCACGGGTGTC |
| 18 | RBS/pBS-SK-rv | ATGTATATCTCCTTCTTACTCTAGAGCGGCCGCCACC |
| 19 | RBS/AtFAR1-fw | GAAGGAGATATACATATGGAATCCAATTGTGTTCAATTTC |
| 20 | pBS-SK/AtFAR1-rv | ACAAAATATTAACGCTTATTGTTTAAGCACATGGGTGATG |
| 21 | RBS/AtFAR2(-120)-fw | GAAGGAGATATACATATGGGACTTGGCATAATCAGTTTCC |
| 22 | pBS-SK/AtFAR2-rv | ACAAAATATTAACGCTTAAGCTCTTCCTTTCAAGACATG |
| 23 | RBS/AtFAR3-fw | GAAGGAGATATACATATGTCGACAGAAATGGAGGTCG |
| 24 | pBS-SK/AtFAR3-rv | ACAAAATATTAACGCTTAGAAGACATACTTAAGCAGCCC |
| 25 | RBS/AtFAR4-fw | GAAGGAGATATACATATGGACTCCAATTGCATTCAGTTC |
| 26 | pBS-SK/AtFAR4-rv | ACAAAATATTAACGCTTATTTTTTGAGTACATAGGTGATGAGG |
| 27 | RBS/AtFAR5-fw | GAAGGAGATATACATATGGAACTCAATTGTGTTCAATTTCT |
| 28 | pBS-SK/AtFAR5-rv | ACAAAATATTAACGCTCACTTCTTAAGCACGTGTGTGAC |
| 30 | RBS/NoKASII-rv | ATGTATATCTCCTTCCTAGGCAACATACTTCTTGAAGACC |
| 31 | RBS/BrFAR1-fw | GAAGGAGATATACATATGGAATCCAACTGTGTTCAGTTTC |
| 32 | pBS-SK/BrFAR1-rv | ACAAAATATTAACGCTTACTGTTTAAGAACATAGGTGATGAGG |
| 33 | RBS/BrFAR5-fw | GAAGGAGATATACATATGGAATTCAACTGTGTTCAATTTCTC |
| 34 | pBS-SK/BrFAR5-rv | ACAAAATATTAACGCTTATTTCTTAAGTACGTGTGTGATGAGG |

TABLE 4

| SEQ ID NO: | Primer | Nucleotide sequence (5'→3') |
|---|---|---|
| 43 | Kmr-F | GATAAACCCAGCGAACCA |
| 44 | Kmr-R | ATCGATACAAATTCCTCG |
| 50 | Trbc-F | GTTACAGTTTTGGCAATTAC |
| 54 | Trbc/NoKASII-R | TGCCAAAACTGTAACCTAGGCAACATACTTCTTGAAGACC |
| 61 | Sp-F | ATCGATTTTCGTTCGTGAATACATG |
| 62 | Sp-R | CATATGCAAGGGTTTATTGTTTTC |
| 66 | Sp/Trbc-R | CGAACGAAAATCGATTTCCCCACTTAGATAAAAAATCCGG |
| 68 | Trbc-AtFAR1-rv | TGCCAAAACTGTAACTTATTGTTTAAGCACATGGGTGATG |
| 70 | Trbc-AtFAR4-rv | TGCCAAAACTGTAACTTATTTTTTGAGTACATAGGTGATGAGG |
| 71 | pUC118/NS1up-F | GGATCCTCTAGAGTCAATGCCTTCTCCAAGGGCGGC |
| 72 | Kmr/NS1up-R | TTCGCTGGGTTTATCCTTCTGGAGCAGGAAGATGTCG |
| 74 | Kmr/NS1down-F | GGAATTTGTATCGATTCGAGTCCCTGCTCGTCACGC |
| 75 | pUC118/NS1down-R | GCATGCCTGCAGGTCCGGCATGGCAATGTCTCTCTG |
| 77 | NS1down-F | TCGAGTCCCTGCTCGTCACGC |
| 78 | Kmr/Ptrc-F | GGAATTTGTATCGATTTGACAATTAATCATCCGGCTCG |
| 79 | Ptrc-R | GGTCTGTTTCCTGTGTGAAATTG |
| 81 | NS1down/Trbc-R | CGAGCAGGGACTCGATTCCCCACTTAGATAAAAAATCC |
| 82 | Ptrc/NoKASII(-40)-F | CACAGGAAACAGACCATGACTGTGCGTCGTGCATCAG |
| 83 | pUC118/orf1593up-F | GGATCCTCTAGAGTCTTGCCGCCAATGTCGATGTAGG |
| 84 | Sp/orf1593up-R | CGAACGAAAATCGATCGCTTTGAAAGTCCAGTTCAAGG |
| 86 | Sp/orf1594down-F | AAACCCTTGCATATGATCACGATCGAGAAGATGGAAGC |
| 87 | pUC118/orf1594down-R | GCATGCCTGCAGGTCGCCAGCCATCAGGCAGTCAAGC |
| 89 | orf1594up-R | CGCTTTGAAAGTCCAGTTCAAGG |
| 90 | orf1593up/Ptrc-F | TGGACTTTCAAAGCGTTGACAATTAATCATCCGGCTCG |
| 91 | orf1593up/PrrnA-F | TGGACTTTCAAAGCGCTCCGTCTACTCTTCTGTCCATCC |

TABLE 4-continued

| SEQ ID NO: | Primer | Nucleotide sequence (5'→3') |
|---|---|---|
| 92 | PrrnA-R | AAGGGAAAACCTCCTTGGCTTAATTAATCTACCTAACT |
| 94 | Ptrc99A2-AtFAR1-F | CACAGGAAACAGACCATGGAATCCAATTGTGTTCAATTTC |
| 95 | PrrnA2-AtFAR4-F | AGGAGGTTTTCCCTTATGGACTCCAATTGCATTCAGTTC |

TABLE 5

| SEQ ID NO: | Primer | Nucleotide sequence (5'→3') |
|---|---|---|
| 37 | pUC118/slr0168up-F | GGATCCTCTAGAGTCATCGCCTGTTGGCCTACC |
| 38 | Kmr/slr0168up-R | TTCGCTGGGTTTATCTACCGTTCAAATTCTGTGGG |
| 40 | Kmr/slr0168down-F | GGAATTTGTATCGATAGCGGAAGATATTACGGGAC |
| 41 | pUC118/slr0168down-R | GCATGCCTGCAGGTCAATCACGTTGGGTCCCAAG |
| 46 | slr0168up-R | TACCGTTCAAATTCTGTGGG |
| 47 | slr0168up/Pcpc560-F | AGAATTTGAACGGTAACCTGTAGAGAAGAGTCCCTG |
| 48 | Pcpc560-R | TGAATTAATCTCCTACTTGAC |
| 51 | Km/Trbc-R | TTCGCTGGGTTTATCTTCCCCACTTAGATAAAAATCC |
| 53 | Pcpc560/NoKASII(-40)-F | TAGGAGATTAATTCAATGACTGTGCGTCGTGCATCAG |
| 55 | pUC118/sII0208up-F | GGATCCTCTAGAGTCATTCCTCGCCCATTTTCAGG |
| 56 | Sp/sII0208up-R | CGAACGAAAATCGATCGCTTTGAAAGTCCAGTTCAAGG |
| 58 | Sp/sII0209down-F | AAACCCTTGCATATGATCACGATCGAGAAGATGGAAGC |
| 59 | pUC118/sII0209down-R | GCATGCCTGCAGGTCATCAGTTGTGCCCGCTGTGC |
| 64 | sII0208up-R | GTCAAATTCGGTGCGGACAG |
| 65 | sII0208up/Pcpc560-F | CGCACCGAATTTGACGCTTTCAGCGGGCAACCAACGAG |
| 67 | Pcpc560-AtFAR1-fw | TAGGAGATTAATTCAATGGAATCCAATTGTGTTCAATTTC |
| 69 | Pcpc560-AtFAR4-fw | TAGGAGATTAATTCAATGGACTCCAATTGCATTCAGTTC |

Preparation Example 1 Preparation of a Transformant which is Obtained by Introducing a NoKASII Gene and an AtFAR Gene into *Escherichia coli*

(1) Construction of Plasmid for NoKASII Gene Expression Wherein Oligonucleotides at N-Terminal Side Thereof was Modified The pBS-SK(−) plasmid (manufactured by Agilent Technologies) was used as a template, and PCR was carried out by using the primer pBS-SK-fw and the primer pBS-SK-ry described in Table 3 to amplify a linearized pBS-SK(−) plasmid.

Further, a cDNA library prepared from *Nannochloropsis oculata* strain NIES-2145 was used as a template, and PCRs were carried out by using the primer pBS/NoKASII(−ATG)-fw and the primer pBS/NoKASII-rv, the primer pBS/NoKASII(−20)-fw and the primer pBS/NoKASII-rv, the primer pBS/NoKASII(−40)-fw and the primer pBS/NoKASII-rv, and the primer pBS/NoKASII(−60)-fw and the primer pBS/NoKASII-ry described in Table 3 respectively, to amplify a NoKASIR-ATG) fragment, a NoKASII(−20) fragment, a NoKASII(−40) fragment and a NoKASII(−60) fragment. The NoKASII(−ATG) fragment consists of the nucleotide sequence of the $7^{th}$ to $1428^{th}$ nucleotides of the nucleotide sequence set forth in SEQ ID NO: 2. The NoKASII(−20) fragment consists of the nucleotide sequence of the $61^{st}$ to $1428^{th}$ nucleotides of the nucleotide sequence set forth in SEQ ID NO: 2. The NoKASII(−40) fragment consists of the nucleotide sequence of the $121^{st}$ to $1428^{th}$ nucleotides of the nucleotide sequence set forth in SEQ ID NO: 2. The NoKASII(−60) fragment consists of the nucleotide sequence of the $181^{st}$ to $1428^{th}$ nucleotides of the nucleotide sequence set forth in SEQ ID NO: 2.

The linearized pBS-SK(−) plasmid and the NoKASII(−ATG) fragment, the NoKASII(−20) fragment, the NoKASII (−40) fragment or the NoKASII(−60) fragment were linked by using the In-Fusion (registered trademark) PCR cloning system (Clontech), to prepare a pBS-SK(−)-NoKASII plasmid, a pBS-SK(−)-NoKASII(−20) plasmid, a pBS-SK(−)-NoKASII(−40) plasmid and a pBS-SK(−)-NoKASII(−60) plasmid.

The plasmid was designed so that the 29 amino acid residues of the lacZ derived from pBS-SK(−) was fused on the N-terminal side of amino acid sequence of the NoKASII.

(2) Construction of Plasmid for AtFAR Gene Expression

The pBS-SK(−) plasmid (manufactured by Agilent Technologies) was used as a template, and PCR was carried out by using the primer RBS/pBS-SK-ry and the primer pBS-SK-fw described in Table 3 to amplify a linearized pBS-SK (−) plasmid.

Further, a cDNA library prepared from *Arabidopsis thaliana* was used as a template, and PCR was carried out by using the primer RBS/AtFAR1-fw and the primer pBS-SK/AtFAR1-ry described in Table 3, to amplify an AtFAR1 gene fragment (Gene ID: AT5G22500.1, SEQ ID NO: 4).

Similar to the method described above, PCRs were carried out by using the primer RBS/AtFAR2(−120)-fw and the primer pBS-SK/AtFAR2-rv, the primer RBS/AtFAR3-fw and the primer pBS-SK/AtFAR3-rv, the primer RBS/AtFAR4-fw and the primer pBS-SK/AtFAR4-rv, and the primer RBS/AtFAR5-fw and the primer pBS-SK/AtFAR5-ry described in Table 3 respectively, to amplify an AtFAR2 (−120) gene fragment (Gene ID: AT3G11980.1; SEQ ID NO: 29), an AtFAR3 gene fragment (Gene ID: AT4G33790.1; SEQ ID NO: 6), an AtFAR4 gene fragment (Gene ID: AT3G44540.1; SEQ ID NO: 8), and an AtFAR5 gene fragment (Gene ID: AT3G44550.1; SEQ ID NO: 10).

The linearized pBS-SK(−) plasmid and the AtFAR1 gene fragment, the AtFAR2(−120) gene fragment, the AtFAR3 gene fragment, the AtFAR4 gene fragment or the AtFAR5 gene fragment were linked by using the In-Fusion (registered trademark) PCR cloning system (Clontech), to prepare a pBS-SK(−)-AtFAR1 plasmid, a pBS-SK(−)-AtFAR2(−120) plasmid, a pBS-SK(−)-AtFAR3 plasmid, a pBS-SK(−)-AtFAR4 plasmid and a pBS-SK(−)-AtFAR5 plasmid.

(3) Construction of Plasmid for NoKASII Gene and AtFAR Gene Expression

The pBS-SK(−)-NoKASII plasmid, the pBS-SK(−)-NoKASII(−20) plasmid, or the pBS-SK(−)-NoKASII(−40) plasmid was used as a template, and PCRs were carried out by using the primer pBS-SK-fw and the primer RBS/NoKASII-ry described in Table 3 to amplify a linearized pBS-SK(−)-NoKASII plasmid, a linearized pBS-SK(−)-NoKASII(−20) plasmid and a linearized pBS-SK(−)-NoKASII(−40) plasmid, respectively.

The linearized pBS-SK(−)-NoKASII plasmid and the AtFAR1 gene fragment, the AtFAR2(−120) gene fragment, the AtFAR3 gene fragment, the AtFAR4 gene fragment or the AtFAR5 gene fragment were linked by using the In-Fusion (registered trademark) PCR cloning system (Clontech), to prepare a pBS-SK(−)-NoKASII-RBS-AtFAR1 plasmid, a pBS-SK(−)-NoKASII-RBS-AtFAR2(−120) plasmid, a pBS-SK(−)-NoKASII-RBS-AtFAR3 plasmid, a pBS-SK(−)-NoKASII-RBS-AtFAR4 plasmid and a pBS-SK(−)-NoKASII-RBS-AtFAR5 plasmid.

Similar to that described above, the linearized pBS-SK(−)-NoKASII(−20) plasmid and the AtFAR1 gene fragment, the AtFAR2(−120) gene fragment, the AtFAR3 gene fragment, the AtFAR4 gene fragment or the AtFAR5 gene fragment were linked by using the In-Fusion (registered trademark) PCR cloning system (Clontech), to prepare a pBS-SK(−)-NoKASII(−20)-RBS-AtFAR1 plasmid, a pBS-SK(−)-NoKASII(−20)-RBS-AtFAR2(−120) plasmid, a pBS-SK(−)-NoKASII(−20)-RBS-AtFAR3 plasmid, a pBS-SK(−)-NoKASII(−20)-RBS-AtFAR4 plasmid and a pBS-SK(−)-NoKASII(−20)-RBS-AtFAR5 plasmid.

Similar to that described above, the linearized pBS-SK(−)-NoKASII(−40) plasmid and the AtFAR1 gene fragment, the AtFAR2(−120) gene fragment, the AtFAR3 gene fragment, the AtFAR4 gene fragment or the AtFAR5 gene fragment were linked by using the In-Fusion (registered trademark) PCR cloning system (Clontech), to prepare a pBS-SK(−)-NoKASII(−40)-RBS-AtFAR1 plasmid, a pBS-SK(−)-NoKASII(−40)-RBS-AtFAR2(−120) plasmid, a pBS-SK(−)-NoKASII(−40)-RBS-AtFAR3 plasmid, a pBS-SK(−)-NoKASII(−40)-RBS-AtFAR4 plasmid and a pBS-SK(−)-NoKASII(−40)-RBS-AtFAR5 plasmid.

(4) Introduction of a Plasmid for NoKASII Gene Expression Wherein Oligonucleotide at N-Terminal Side Thereof was Modified, a Plasmid for AtFAR Gene Expression, and Plasmid for NoKASII Gene and AtFAR Gene Expression into *Escherichia coli*

*Escherichia coli* strain K27AFadD (obtained from Coli-genetic stock center, see http://cgsc.biology.yale.edu/Strain.php?ID=5655) inoculated in 1 mL of LB medium was cultured at 37° C. until $OD_{600}$ became about 0.3 to 0.4.

Bacteria cells were collected by centrifugation, and 100 μL of an ice-cooled TSS solution (10% PEG6000, 5% DMSO, 35 mM $MgSO_4$) and the above-described plasmid solution were mixed, and allowed to stand on ice for 30 minutes. Then, heat shock at 42° C. for 1 minute was applied thereto, and the resulting solution was applied to an ampicillin-containing LB plate, and cultured overnight at 30° C. After culturing, strains into which the plasmid was introduced were selected by applying drug resistance as an indicator.

Preparation Example 2 Preparation of Transformant by Introducing NoKASII Gene and BrFAR Gene into *Escherichia coli*

(1) Construction of Plasmid for BrFAR Gene Expression

PCR was carried out to amplify a BrFAR1 gene fragment (NCBI Accession number: XM_009122403; SEQ ID NO: 35) by using a cDNA library prepared form *Brassica raga* as a template, and the primer RBS/BrFAR1-fw and the primer pBS-SK/BrFAR1-ry described in Table 3.

In a similar manner as described above, PCR was carried out by using the primer RBS/BrFAR5-fw and the primer pBS-SK/BrFAR5-ry described in Table 3 to amplify a BrFAR5 gene fragment (NCBI Accession number: XM_009152061; SEQ ID NO: 36).

(2) Construction of Plasmid for NoKASII Gene and BrFAR Gene Expression

The linearized pBS-SK(−)-NoKASII plasmid, the linearized pBS-SK(−)-NoKASII(−20) plasmid or the linearized pBS-SK(−)-NoKASII(−40) plasmid, which were prepared by a method similar to that described in Preparation Example 1, and the BrFAR1 gene fragment or the BrFAR5 gene fragment were linked by using the In-Fusion (registered trademark) PCR cloning system (Clontech), to prepare a pBS-SK(−)-NoKASII-RBS-BrFAR1 and pBS-SK(−)-NoKASII-RBS-BrFAR5 plasmid, a pBS-SK(−)-NoKASII(−20)-RBS-BrFAR1 and pBS-SK(−)-NoKASII(−20)-RBS-BrFAR5 plasmid, and a pBS-SK(−)-NoKASII(−40)-RBS-BrFAR1 and pBS-SK(−)-NoKASII(−40)-RBS-BrFAR5 plasmid.

(3) Introduction of a Plasmid for NoKASII Gene and BrFAR Gene Expression into *Escherichia coli*

*Escherichia coli* strain K27AFadD (obtained from Coli-genetic stock center, see http://cgsc.biology.yale.edu/Strain.php?ID=5655) inoculated in 1 mL of LB medium was cultured at 37° C. until $OD_{600}$ became about 0.3 to 0.4.

Bacteria cells were collected by centrifugation, and 100 μL of an ice-cooled TSS solution (10% PEG6000, 5% DMSO, 35 mM $MgSO_4$) and the above-described plasmid solution were mixed, and allowed to stand on ice for 30 minutes. Then, heat shock at 42° C. for 1 minute was applied thereto, and the resulting solution was applied to an ampicillin-containing LB plate, and cultured overnight at 30° C. After culturing, strains into which the plasmid was introduced were selected by applying drug resistance as an indicator.

Test Example 1 Production of Fatty Alcohols

The colonies of the transformants prepared in Preparation Examples 1 and 2 were inoculated into 2 mL of Overnight Express Instant TB Medium (manufactured by Takara), and cultured at 30° C. for 24 hours by shaking (160 rpm).

The bacterial cells were collected by separating 1 mL of culture fluid into a glass test tube, and by centrifuging at 3,000 rpm. A precipitate obtained by removing a supernatant was suspended into 0.5 mL of distilled water, and as an internal standard, 25 μL of C23:0 alcohol (1-tricosanol) (1 mg/mL) dissolved in chloroform was added thereto, respectively. Then, 0.5 mL of chloroform and 1 mL of methanol were added thereto, and the resultant mixture was stirred and further left to stand for 30 minutes. Then, 0.5 mL of chloroform and 0.5 mL of 1.5% KCl solution were added thereto, and the resultant mixture was stirred. The resultant mixture was centrifuged at 3,000 rpm for 15 minutes, and then an organic layer (lower layer) was collected into a test tube with cap by using a Pasteur pipette, and dried and solidified by a nitrogen gas.

To a dried and solidified lipid fraction, 0.7 mL of 0.5 N KOH methanol solutions was added, and the resultant mixture was saponified at 80° C. for 30 minutes. Further, 1 mL of boron trifluoride-methanol solution was added thereto, and a methyl esterification reaction was carried out thereon at 80° C. for 10 minutes. To this reaction fluid, 0.2 to 0.5 mL of hexane and 1 mL of saturated saline solution were added and the resultant mixture was centrifuged for 10 minutes at room temperature, and then a hexane layer being an upper layer was collected.

The collected hexane layer was transferred to a test tube with a screw cap, and dried into solid by nitrogen, and 100 µL of a silylating agent TMSI-H containing hexamethyld-isilazane and trimethylchlorosilane dissolved in pyridine (manufactured by GL Sciences Inc.) was added thereto. The resulting mixture was allowed to react at 80° C. for 30 minutes, and then 300 µL of hexane and 0.5 mL of 1.5% KCl solution were added thereto, and stirred. Further, the resulting mixed liquid was subjected to centrifugation at room temperature for 10 minutes, and a hexane layer being an upper layer was collected and provided for GC analysis.

First, fatty acid methyl esters and trimethylsilylated fatty alcohols were identified by gas chromatography mass spectrometry analysis. Next, based on a peak area of waveform data obtained by gas chromatography analysis, proportions (%) of amounts of various fatty acids in the total amount of fatty acids produced by each transformant, and proportions (%) of amounts of various fatty alcohols in the total amount of fatty alcohols were calculated.

Conditions of gas chromatography mass spectrometry analysis and gas chromatographic analysis are shown.
<Gas Chromatography Mass Spectrometry Analysis>
Analysis apparatus: 7890A GC system (manufactured by Agilent), 5975 Inert XL MSD (manufactured by Agilent)
Capillary column: DB-1 MS (30 m×20 µm×0.25 µm; manufactured by J&W Scientific)
Mobile phase: High purity Helium
Flow rate inside the column: 1.0 mL/min
Temperature rise program: 100° C. (for 1 min)→12.5° C./min (to 200° C.)→5° C./min (to 250° C.)→250° C. (for 9 min)
Equilibration time: for 0.5 min
Injection port: split injection (split ratio: 0.1:1)
Pressure: 55.793 psi
Amount of injection: 5 µL
Cleaning vial: methanol/chloroform
Detector temperature: 350° C.
<Gas chromatographic analysis >
Analysis apparatus: 7890A GC system (Agilent)
Capillary column: DB-1 MS (30 m×20 µm×0.25 µm; manufactured by J&W Scientific)
Mobile phase: Helium
Flow rate inside the column: 0.25 mL/min
Temperature rise program: 80° C. (for 0 min)→15° C./min (to 320° C.)
Equilibration time: for 0.5 min
Injection port: split injection (split ratio: 75:1)
Pressure: 48.475 psi
Amount of injection: 5 µL
Cleaning vial: methanol/chloroform
Detector temperature: 350° C.

Table 6 shows compositions (%) of various fatty acids produced by each transformant, and Tables 7 to 10 show compositions (%) of various fatty alcohols, respectively. These results are shown in terms of an average value and a standard deviation in a series of three culture experiments.

TABLE 6

| | % of total fatty acid | | | | | | | | |
|---|---|---|---|---|---|---|---|---|---|
| | C12:0-COOH | C14:1-COOH | C14:0-COOH | C15:0-COOH | C16:1-COOH | C16:0-COOH | C17:1-COOH | C17:0-COOH | C18:1-COOH |
| ΔFadD | 0.54 ± 0.01 | 0.41 ± 0.01 | 4.79 ± 0.07 | 1.25 ± 0.11 | 1.23 ± 0.11 | 45.36 ± 0.47 | 27.69 ± 0.37 | n.d. | 5.79 ± 0.18 |
| NoKASII(-ATG) | n.d. | n.d. | 1.42 ± 0.05 | 2.07 ± 0.04 | 7.98 ± 0.61 | 44.19 ± 0.21 | 17.66 ± 0.83 | 3.93 ± 0.14 | 16.75 ± 0.44 |
| NoKASII(-20) | n.d. | n.d. | 1.02 ± 0.11 | 0.97 ± 0.37 | 13.40 ± 0.83 | 32.77 ± 0.31 | 14.24 ± 0.57 | 2.03 ± 0.54 | 23.43 ± 0.64 |
| NoKASII(-40) | n.d. | n.d. | 1.47 ± 0.05 | 1.53 ± 0.16 | 5.01 ± 0.31 | 43.54 ± 1.04 | 19.77 ± 0.64 | 3.45 ± 0.30 | 13.92 ± 0.12 |
| NoKASII(-60) | n.d. | n.d. | 1.65 ± 0.04 | 1.62 ± 0.01 | 4.55 ± 3.73 | 47.46 ± 1.53 | 20.63 ± 1.11 | 2.19 ± 0.12 | 16.10 ± 0.70 |

| | % of total fatty acid | | | | | | | | |
|---|---|---|---|---|---|---|---|---|---|
| | C18:0-COOH | C19:1-COOH | C20:1-COOH | C20:0-COOH | C22:1-COOH | C22:0-COOH | C24:1-COOH | C26:1-COOH | C28:1-COOH |
| ΔFadD | 0.78 ± 0.05 | 12.16 ± 0.33 | n.d. | n.d. | n.d. | n.d. | n.d. | n.d. | n.d. |
| NoKASII(-ATG) | 2.62 ± 0.03 | 3.15 ± 0.23 | 0.23 ± 0.01 | n.d. | n.d. | n.d. | n.d. | n.d. | n.d. |
| NoKASII(-20) | 4.46 ± 0.12 | 2.22 ± 0.17 | 1.58 ± 0.07 | 0.41 ± 0.02 | 0.73 ± 0.02 | 0.31 ± 0.02 | 1.22 ± 0.09 | 0.71 ± 0.06 | 0.50 ± 0.04 |
| NoKASII(-40) | 4.37 ± 0.11 | 5.38 ± 0.30 | 0.58 ± 0.01 | 0.25 ± 0.00 | 0.16 ± 0.01 | 0.10 ± 0.00 | 0.23 ± 0.01 | 0.13 ± 0.01 | 0.09 ± 0.00 |
| NoKASII(-60) | 1.58 ± 0.03 | 4.22 ± 0.35 | n.d. | n.d. | n.d. | n.d. | n.d. | n.d. | n.d. | n.d.: Not Detected

TABLE 7

| | % of total fatty alcohol | | | | |
|---|---|---|---|---|---|
| | C14:0-OH | C16:1-OH | C16:0-OH | C18:1-OH | C18:0-OH |
| ΔFadD | n.d. | n.d. | n.d. | n.d. | n.d. |
| AtFAR1 | 3.00 ± 0.08 | n.d. | 83.37 ± 0.54 | 12.27 ± 0.52 | 1.36 ± 0.05 |
| AtFAR2(-120) | 13.83 ± 1.30 | 2.44 ± 0.16 | 76.62 ± 1.78 | 7.11 ± 0.33 | n.d. |

TABLE 7-continued

| | | | | | |
|---|---|---|---|---|---|
| AtFAR3 | 0.00 ± 0.00 | n.d. | 93.90 ± 10.57 | 6.10 ± 10.57 | n.d. |
| AtFAR4 | 4.92 ± 2.00 | n.d. | 67.81 ± 7.06 | 24.46 ± 6.58 | 2.80 ± 2.54 |
| AtFAR5 | 0.48 ± 0.01 | n.d. | 68.18 ± 0.36 | 29.20 ± 0.38 | 2.14 ± 0.03 |
| BrFAR1 | 2.20 ± 1.00 | n.d. | 59.43 ± 4.54 | 33.30 ± 3.38 | 5.06 ± 4.95 |
| BrFAR5 | 2.05 ± 0.22 | n.d. | 85.26 ± 0.52 | 12.69 ± 0.73 | n.d. |

| | % of total fatty alcohol | | | | | |
|---|---|---|---|---|---|---|
| | C20:1-OH | C20:0-OH | C22:1-OH | C22:0-OH | C24:1-OH | C26:1-OH |
| ΔFadD | n.d. | n.d. | n.d. | n.d. | n.d. | n.d. |
| AtFAR1 | n.d. | n.d. | n.d. | n.d. | n.d. | n.d. |
| AtFAR2(-120) | n.d. | n.d. | n.d. | n.d. | n.d. | n.d. |
| AtFAR3 | n.d. | n.d. | n.d. | n.d. | n.d. | n.d. |
| AtFAR4 | n.d. | n.d. | n.d. | n.d. | n.d. | n.d. |
| AtFAR5 | n.d. | n.d. | n.d. | n.d. | n.d. | n.d. |
| BrFAR1 | n.d. | n.d. | n.d. | n.d. | n.d. | n.d. |
| BrFAR5 | n.d. | n.d. | n.d. | n.d. | n.d. | n.d. | n.d.: Not Detected

TABLE 8

| | % of total fatty alcohol | | | | | |
|---|---|---|---|---|---|---|
| | C16:0-OH | C17:0-OH | C18:1-OH | C18:0-OH | C20:1-OH | C20:0-OH |
| NoKASII | n.d. | n.d. | n.d. | n.d. | n.d. | n.d. |
| NoKASII + AtFAR1 | 66.42 ± 0.22 | 4.78 ± 0.25 | 6.53 ± 0.10 | 19.70 ± 0.35 | 2.57 ± 0.03 | n.d. |
| NoKASII + AtFAR2(-120) | 86.83 ± 0.16 | n.d. | 11.10 ± 0.11 | 2.07 ± 0.06 | n.d. | n.d. |
| NoKASII + AtFAR3 | n.d. | n.d. | n.d. | n.d. | n.d. | n.d. |
| NoKASII + AtFAR4 | 38.68 ± 1.28 | 5.21 ± 1.42 | 12.64 ± 0.32 | 36.10 ± 1.99 | 5.95 ± 0.64 | 1.43 ± 0.22 |
| NoKASII + AtFAR5 | 34.86 ± 0.03 | 2.83 ± 0.23 | 31.70 ± 0.25 | 20.42 ± 0.31 | 8.11 ± 0.09 | 0.85 ± 0.01 |
| NoKASII + BrFAR1 | 56.78 ± 8.50 | 4.53 ± 1.00 | 9.82 ± 1.58 | 26.27 ± 6.34 | 2.11 ± 0.68 | 0.49 ± 0.51 |
| NoKASII + BrFAR5 | 61.18 ± 0.20 | 2.78 ± 0.25 | 12.34 ± 0.43 | 19.15 ± 0.51 | 3.67 ± 0.09 | 0.47 ± 0.03 |

| | % of total fatty alcohol | | | |
|---|---|---|---|---|
| | C22:1-OH | C22:0-OH | C24:1-OH | C26:1-OH |
| NoKASII | n.d. | n.d. | n.d. | n.d. |
| NoKASII + AtFAR1 | n.d. | n.d. | n.d. | n.d. |
| NoKASII + AtFAR2(-120) | n.d. | n.d. | n.d. | n.d. |
| NoKASII + AtFAR3 | n.d. | n.d. | 55.72 ± 2.06 | 44.28 ± 2.06 |
| NoKASII + AtFAR4 | n.d. | n.d. | n.d. | n.d. |
| NoKASII + AtFAR5 | 1.05 ± 0.03 | n.d. | 0.18 ± 0.00 | n.d. |
| NoKASII + BrFAR1 | n.d. | n.d. | n.d. | n.d. |
| NoKASII + BrFAR5 | 0.41 ± 0.03 | n.d. | n.d. | n.d. | n.d.: Not Detected

TABLE 9

| | % of total fatty alcohol | | | | | |
|---|---|---|---|---|---|---|
| | C16:0-OH | C17:0-OH | C18:1-OH | C18:0-OH | C20:1-OH | C20:0-OH |
| NoKASII(-20) | n.d. | n.d. | n.d. | n.d. | n.d. | n.d. |
| NoKASII(-20) + AtFAR1 | 49.96 ± 1.48 | 3.67 ± 0.40 | 2.41 ± 0.28 | 37.03 ± 1.22 | 3.08 ± 0.14 | 3.05 ± 0.04 |
| NoKASII(-20) + AtFAR2(-120) | 86.83 ± 0.08 | n.d. | 9.10 ± 0.26 | 4.06 ± 0.20 | n.d. | n.d. |

TABLE 9-continued

| | | | | | | |
|---|---|---|---|---|---|---|
| NoKASII(-20) + AtFAR3 | n.d. | n.d. | n.d. | n.d. | n.d. | n.d. |
| NoKASII(-20) + AtFAR4 | 15.50 ± 1.83 | 2.25 ± 0.86 | 5.20 ± 0.68 | 47.19 ± 1.97 | 14.66 ± 1.72 | 8.39 ± 0.49 |
| NoKASII(-20) + AtFAR5 | 26.56 ± 0.79 | 2.00 ± 0.11 | 20.99 ± 0.03 | 28.38 ± 0.03 | 13.27 ± 0.33 | 2.50 ± 0.13 |
| NoKASII(-20) + BrFAR1 | 47.79 ± 6.52 | 3.10 ± 0.21 | 4.15 ± 0.34 | 40.49 ± 5.88 | 2.42 ± 0.21 | 2.05 ± 0.35 |
| NoKASII(-20) + BrFAR5 | 29.59 ± 1.42 | n.d. | 11.54 ± 0.39 | 33.74 ± 0.83 | 13.56 ± 0.65 | 3.66 ± 0.24 |

| | % of total fatty alcohol | | | |
|---|---|---|---|---|
| | C22:1-OH | C22:0-OH | C24:1-OH | C26:1-OH |
| NoKASII(-20) | n.d. | n.d. | n.d. | n.d. |
| NoKASII(-20) + AtFAR1 | 0.80 ± 0.10 | n.d. | n.d. | n.d. |
| NoKASII(-20) + AtFAR2(-120) | n.d. | n.d. | n.d. | n.d. |
| NoKASII(-20) + AtFAR3 | n.d. | n.d. | 42.00 ± 5.31 | 58.00 ± 5.31 |
| NoKASII(-20) + AtFAR4 | 4.17 ± 0.60 | 1.29 ± 0.21 | 1.35 ± 0.09 | n.d. |
| NoKASII(-20) + AtFAR5 | 4.15 ± 0.12 | 0.53 ± 0.01 | 1.62 ± 0.08 | n.d. |
| NoKASII(-20) + BrFAR1 | n.d. | n.d. | n.d. | n.d. |
| NoKASII(-20) + BrFAR5 | 7.91 ± 1.04 | n.d. | n.d. | n.d. | n.d.: Not Detected

TABLE 10

| | % of total fatty alcohol | | | | |
|---|---|---|---|---|---|
| | C16:0-OH | C17:0-OH | C18:1-OH | C18:0-OH | C20:1-OH |
| NoKASII(-40) | n.d. | n.d. | n.d. | n.d. | n.d. |
| NoKASII(-40) + AtFAR1 | 45.35 ± 1.08 | 15.62 ± 2.99 | 4.59 ± 0.96 | 28.51 ± 0.57 | 4.10 ± 0.58 |
| NoKASII(-40) + AtFAR2(-120) | 85.64 ± 0.84 | n.d. | 12.06 ± 0.82 | 2.29 ± 0.07 | n.d. |
| NoKASII(-40) + AtFAR3 | n.d. | n.d. | n.d. | n.d. | n.d. |
| NoKASII(-40) + AtFAR4 | 24.06 ± 3.09 | 8.41 ± 1.58 | 9.54 ± 0.39 | 45.08 ± 2.14 | 9.27 ± 1.34 |
| NoKASII(-40) + AtFAR5 | 24.79 ± 2.92 | 4.83 ± 1.24 | 21.82 ± 1.44 | 29.97 ± 1.03 | 12.53 ± 2.13 |
| NoKASII(-40) + BrFAR1 | 36.10 ± 1.93 | 3.97 ± 0.88 | 9.64 ± 0.48 | 42.66 ± 1.66 | 4.61 ± 0.30 |
| NoKASII(-40) + BrFAR5 | 60.10 ± 0.97 | 3.99 ± 0.57 | 19.50 ± 1.23 | 13.65 ± 0.20 | 2.77 ± 0.23 |

| | % of total fatty alcohol | | | | |
|---|---|---|---|---|---|
| | C20:0-OH | C22:1-OH | C22:0-OH | C24:1-OH | C26:1-OH |
| NoKASII(-40) | n.d. | n.d. | n.d. | n.d. | n.d. |
| NoKASII(-40) + AtFAR1 | 1.83 ± 0.11 | n.d. | n.d. | n.d. | n.d. |
| NoKASII(-40) + AtFAR2(-120) | n.d. | n.d. | n.d. | n.d. | n.d. |
| NoKASII(-40) + AtFAR3 | n.d. | n.d. | n.d. | 47.21 ± 0.84 | 52.79 ± 0.84 |
| NoKASII(-40) + AtFAR4 | 3.64 ± 0.53 | n.d. | n.d. | n.d. | n.d. |
| NoKASII(-40) + AtFAR5 | 1.94 ± 0.21 | 3.15 ± 0.80 | n.d. | n.d. | n.d. |
| NoKASII(-40) + BrFAR1 | 2.60 ± 0.19 | 0.42 ± 0.37 | n.d. | n.d. | n.d. |
| NoKASII(-40) + BrFAR5 | n.d. | n.d. | n.d. | n.d. | n.d. | n.d.: Not Detected

As shown in Table 6, long-chain fatty acids (fatty acids having 20 or more carbon atoms), which were not observed in the ΔFadD strain being a control, were detected in the transformants prepared by introducing a gene encoding the NoKASII, the NoKASII(−20) in which 20 residues of amino acids at N-terminal side of NoKASII containing a putative chloroplast localization signal were deleted or the NoKASII (−40) in which 40 residues thereof were deleted. Here, the long-chain fatty acid is a substrate for a long-chain fatty alcohol having 20 or more carbon atoms, and a supply amount of acyl-ACP having 20 or more carbon atoms increased in the transformants prepared by introducing each of the NoKASII, the NoKASII(−20) gene or the NoKASII (−40) gene thereinto.

As shown in Table 7, when various FAR genes were independently introduced, fatty alcohols having 18 or less carbon atoms were detected. However, no long-chain fatty alcohol was detected.

On the other hand, as shown in Tables 8 to 10, formation of fatty alcohols having 20 to 26 carbon atoms was confirmed in strains prepared by introducing the NoKASII gene, the NoKASII (−20) gene or the NoKASII (−40) gene, together with the AtFAR1 gene, the AtFAR3 gene, the AtFAR4 gene, the AtFAR5 gene, the BrFAR1 gene or the BrFAR5 gene and expressing both. Accordingly, expression of both the KASII gene and the FAR gene is necessary for producing long-chain fatty alcohols.

However, no formation of alcohols having 20 or more carbon atoms was observed in strains prepared by introducing the NoKASII gene, NoKASII(−20) gene or NoKASII (−40) gene, and the AtFAR2(−120) gene and expressing both. Therefore, it is necessary to use appropriately in combination of the NoKASII gene with the FAR gene wherein the FAR uses acyl-ACP having 20 or more carbon atoms as the substrate. In addition, identities of the amino acid sequence of AtFAR2(−120) to the amino acid sequences of every kind of FARs are, 39% to the AtFAR1, 38% to the AtFAR3, 41% to the AtFAR4, 40% to the AtFAR5, 40% to the BrFAR1, and 40% to the BrFAR5.

Moreover, even when the same FAR gene was introduced thereinto, a proportion of amounts of long-chain fatty alcohols in the total fatty alcohols was the highest when the NoKASII(−20) gene was introduced thereinto, and tended to be higher subsequently when the NoKASII(−40) gene was introduced thereinto, and when the NoKASII gene was introduced thereinto.

Preparation Example 3 Preparation of Transformant by Introducing NoKASII Gene and AtFAR Gene into Cyanobacteria (1) Construction of Plasmid for Kanamycin Resistance Gene Expression Using genomic DNA of Synechococcus elongatus sp. strain PCC7942 as a template, and the primer pUC118/NS1up-F and the primer Kmr/NS1up-R described in Table 4, PCR was carried out to amplify the upstream fragment of a neutral site NS1 region (NS1up fragment; SEQ ID NO: 73). Further, using the genomic DNA described above as a template, and the primer Kmr/NS1down-F and the primer pUC118/NS1down-R described in Table 4, PCR was carried out to amplify the downstream fragment of a neutral site NS1 region (NS1down fragment; SEQ ID NO: 76).

Furthermore, using a plasmid of pJH1 (Trieu-Cuot P et al., Gene, 1983, vol. 23, p. 331-341) as a template, and the primer Kmr-F and the primer Kmr-R described in Table 4, PCR was carried out to amplify a kanamycin resistance marker gene fragment (Kmr fragment; SEQ ID NO: 45).

A pUC118-NS1::Km plasmid was obtained by inserting the NS1up fragment, the NS1down fragment, and the Kmr fragment into a place between the HincII sites of the pUC118 plasmid (manufactured by Takara Bio) by using the In-Fusion (registered trademark) PCR cloning system (Clontech).

(2) Construction of Plasmid for NoKASII Gene Expression

Using the pUC118-NS1::Km plasmid as a template and the primer Kmr-R and the primer NS1down-F described in Table 4, PCR was carried out to amplify a linearized pUC118-NS1::Km plasmid.

Then, using a trc promoter sequence, which was artificially synthesized form the sequence of a pTrc99A cloning plasmid (NCBI Accession number: M22744), as a template, and the primer Kmr/Ptrc-F and the primer Ptrc-R described in Table 4, PCR was carried out to amplify a trc promoter fragment (Ptrc fragment; SEQ ID NO: 80).

Further, PCR was carried out by using genomic DNA of the wild-type strains of Synechocystis sp. strain PCC6803 as a template, and the primer Trbc-F and the primer NS1down/Trbc-R described in Table 4 to amplify a terminator fragment of a rbc gene (Trbc fragment, SEQ ID NO: 52).

Furthermore, using a cDNA library prepared from Nannochloropsis oculata strain NIES-2145 as a template, and the primer Ptrc/NoKASII(−40)-F and the primer Trbc/NoKASII-R described in Table 4, PCR was carried out to amplify a chloroplast transit signal deleted NoKASII gene fragment (NoKASII(−40) fragment; a nucleotide sequence of the $121^{st}$ to $1428^{th}$ nucleotides set forth in SEQ ID NO: 2 wherein a start codon (ATG) was added to 5' end side thereof; SEQ ID NO: 97).

Then, the linearized pUC118-NS1::Km plasmid, the Ptrc fragment, the Trbc fragment, and the NoKASII(−40) fragment were mixed, and the resultant mixture was cloned by using the In-Fusion (registered trademark) PCR Cloning system (Clontech) to obtain a pUC118-NS1::Km-Ptrc-NoKASII(−40)-Trbc plasmid in which the kanamycin resistance gene cassette, the trc promoter region, the NoKASII (−40) gene, and the rbc terminator were inserted in this order into a neutral site NS1 region derived from Synechococcus elongatus sp. strain PCC7942.

(3) Construction of Plasmid for Spectinomycin Resistance Gene Expression

Using genomic DNA of the wild-type strain of Synechococcus elongatus sp. PCC7942 as a template, and the primer pUC118/orf1593up-F and the primer Sp/orf1593up-R described in Table 4, PCR was carried out to amplify the upstream fragment of an orf1593 region (orf1593up fragment; SEQ ID NO: 85). Further, using the genomic DNA described above as a template, and the primer Sp/orf1594down-F and the primer pUC118/orf1594down-R described in Table 4, PCR was carried out to amplify the downstream fragment of an orf1594 region (orf1594down fragment; SEQ ID NO: 88).

Furthermore, using a pDG1726 plasmid (Guerout-Fleury et al., Gene, 1995, vol. 167, p. 335-336) as a template, and the primer Sp-F and the primer Sp-R described in Table 4, PCR was carried out to amplify a spectinomycin resistance marker gene fragment (Sp fragment; SEQ ID NO: 63).

A pUC118-orf1593/1594::Sp plasmid was obtained by inserting the orf1593up fragment, the orf1594down fragment, and the Sp fragment into a place between the HincII sites of the pUC118 plasmid (manufactured by Takara Bio) by using the In-Fusion (registered trademark) PCR cloning system (Clontech).

(4) Construction of Plasmid for AtFAR Gene Expression

Using the pUC118-orf1593/1594::Sp plasmid as a template and the primer Sp-F and the primer orf1594up-R described in Table 4, PCR was carried out to amplify a linearized pUC118-orf1593/1594::Sp plasmid.

Then, using a trc promoter sequence, which was artificially synthesized form the sequence of a pTrc99A cloning plasmid (NCBI Accession number: M22744) as a template, and the primer orf1593up/Ptrc-F and the primer Ptrc-R described in Table 4, PCR was carried out to amplify a trc promoter fragment (Ptrc fragment, SEQ ID NO: 80). In a manner similar to that described above, using genomic DNA of *Synechococcus elongatus* sp. strain PCC7942 as a template, and the primer orf1593up/PrrnA-F and the primer PrrnA-R described in Table 4, PCR was carried out to amplify a promoter fragment of an rrnA operon gene derived from *Synechococcus elongatus* sp. strain PCC7942 (Prrn fragment; SEQ ID NO: 93).

Further, PCR was carried out by using genomic DNA of the wild-type strains of *Synechocystis* sp. strain PCC6803, and the primer Trbc-F and the primer Sp/Trbc-R described in Table 4 to amplify a terminator fragment of a rbc gene (Trbc fragment, SEQ ID NO: 52).

Furthermore, using a cDNA library prepared from *Arabidopsis thaliana* as a template, and the primer Ptrc99A2-AtFAR1-F and the primer Trbc/AtFAR1-ry described in Table 4, PCR was carried out to amplify an AtFAR1 gene fragment (SEQ ID NO: 4). In a manner similar to that described above, using the primer PrrnA2-AtFAR4-F and the primer Trbc/AtFAR4-ry described in Table 4, PCR was carried out to amplify an AtFAR4 gene fragment (SEQ ID NO: 8).

Then, the linearized pUC118-orf1593/1594::Sp plasmid, the Ptrc fragment, the Trbc fragment, and the AtFAR1 gene fragment were mixed, and the resultant mixture was cloned by using the In-Fusion (registered trademark) PCR Cloning system (Clontech) to obtain a pUC118-orf1593/1594::Ptrc-AtFAR1-Trbc-Sp plasmid in which the trc promoter, the AtFAR1 gene fragment, and the rbc terminator and the spectinomycin resistance gene cassette were inserted in this order into an orf1593/1594 region derived from *Synechococcus* sp. strain PCC7942.

By a method in a manner similar to that described above, the linearized pUC118-orf1593/1594::Sp plasmid, the PrrnA fragment, the Trbc fragment, and the AtFAR4 gene fragment were mixed, and the resultant mixture was cloned by using the In-Fusion (registered trademark) PCR Cloning system (Clontech) to obtain a pUC118-orf1593/1594::PrrnA-AtFAR4-Trbc-Sp plasmid in which a promoter of an rrnA operon gene, the AtFAR4 gene fragment, and the rbc terminator and the spectinomycin resistance gene cassette were inserted in this order into an orf1593/1594 region derived from *Synechococcus elongatus* sp. strain PCC7942.

(5) Introduction of Plasmid for NoKASII Gene Expression and Plasmid for AtFAR Gene Expression into Cyanobacteria Using thus-obtained pUC118-NS1::Km-Ptrc-NoKASII(-40)-Trbc plasmid, pUC118-orf1593/1594::Ptrc-AtFAR1-Trbc-Sp plasmid and pUC118-orf1593/1594::PrrnA-AtFAR4-Trbc-Sp plasmid, *Synechococcus elongatus* sp. strain PCC7942 was transformed by a spontaneous transformation method, and the resultant material was selected by kanamycin resistance and spectinomycin resistance.

In this way, a ΔNS1::NoKASII(-40)Δorf1593/1594::AtFAR1 strain and a ΔNS1::NoKASII(-40)Δorf1593/1594::AtFAR4 strain were obtained, in which the construct for the NoKASII(-40) gene expression was introduced into the NS1 region and the AtFAR1 gene or the AtFAR4 gene was introduced into the orf1593/1594 region on a genome of *Synechococcus elongatus* sp. strain PCC7942.

In addition, in a manner similar to that described above, a ΔNS1::NoKASII(-40) strain into which the construct for NoKASII(-40) gene expression was introduced, and a Δorf1593/1594::AtFAR4 strain wherein the AtFAR4 gene was introduced into the orf1593/1594 region, were obtained respectively.

Test Example 2 Production of Fatty Alcohols

In a 50 mL Erlenmeyer flask to which 20 mL of BG-11 medium having the composition shown in Table 9 below was added, the transformant prepared in Preparation Example 3, and *Synechococcus elongatus* sp. strain PCC7942 (wild type) were cultured for 14 days. The cultivations were conducted by using a rotary shaker (120 rpm) at 30° C. under predetermined lighting (60 $\mu$E·m$^{-2}$·sec$^{-1}$), and an initial bacterial cell concentration set to 0.2 in OD$_{730}$. In addition, suitable antibiotic was added to the BG-11 medium for cultivation of the transformants to be 25 $\mu$g/mL in a concentration.

TABLE 11

| Composition of BG-11 liquid medium Stock solution | |
|---|---|
| A solution | 2 mL |
| B solution | 50 mL |
| C solution | 2 mL |
| D solution | 1 mL |
| 1.0M TES-KOH (pH 8.2) | 5 mL |
| Total | 1000 mL |

| Composition of stock solution | | | |
|---|---|---|---|
| A solution | | B solution | |
| Citric acid•H$_2$O | 0.33 g | NaNO$_3$ | 30 g |
| Ferric ammonium citrate | 0.3 g | K$_2$HPO$_4$ | 0.78 g |
| Na$_2$EDTA | 0.05 g | MgSO$_4$•7H$_2$O | 1.5 g |
| total | 100 mL | total | 100 mL |

C solution CaCl$_2$.2H$_2$O 1.9 g/100 mL
D solution
[H$_3$BO$_3$ 2.86 g, MnCl$_2$.4H$_2$O 1.81 g, ZnSO$_4$.7H$_2$O 0.22 g, CuSO$_4$.5H$_2$O 0.08 g, Na$_2$MoO$_4$ 0.021 g, Co(NO$_3$).6H$_2$O 0.0494 g, H$_2$SO$_4$ single drop, H$_2$O]/1000 mL The bacterial cells were collected by separating 2 to 5 mL of culture fluid into a glass test tube, and by centrifuging at 3,000 rpm. A precipitate obtained by removing a supernatant was suspended into 0.5 mL of distilled water, and as an internal standard, 25 $\mu$L of C23:0 alcohol (1-tricosanol) (1 mg/mL) dissolved in chloroform was added thereto. Then, 0.5 mL of chloroform and 1 mL of methanol were added thereto, and the resultant mixture was stirred and further left to stand for 30 minutes. Then, 0.5 mL of chloroform and 0.5 mL of 1.5% KCl solution were added thereto, and the resultant mixture was stirred. The resultant mixture was centrifuged at 3,000 rpm for 15 minutes, and then an organic layer (lower layer) was collected into a test tube with cap by using a Pasteur pipette, and dried and solidified by a nitrogen gas.

To a dried and solidified lipid fraction, 0.7 mL of 0.5 N KOH methanol solutions was added, and the resultant mixture was stirred and saponified at 80° C. for 30 minutes. Further, 1 mL of boron trifluoride-methanol solution was added thereto, and a methyl esterification reaction was carried out thereon at 80° C. for 10 minutes. To this reaction fluid, 0.2 to 0.5 mL of hexane and 1 mL of saturated saline solution were added and the resultant mixture was centrifuged for 10 minutes at room temperature, and then a hexane layer being an upper layer was collected.

The collected hexane layer was transferred to a test tube with a screw cap, and dried into solid by nitrogen, and 100 µL of a silylating agent TMSI-H containing hexamethyldisilazane and trimethylchlorosilane dissolved in pyridine (manufactured by GL Sciences Inc.) was added thereto. The resulting mixture was allowed to react at 80° C. for 30 minutes, and then 300 µL of hexane and 0.5 mL of 1.5% KCl solution were added thereto, and stirred. Further, the resulting mixed liquid was subjected to centrifugation at room temperature for 10 minutes, and a hexane layer being an upper layer was collected and provided for GC analysis.

First, fatty acid methyl esters and trimethylsilylated fatty alcohols were identified by gas chromatography mass spectrometry analysis. Next, based on a peak area of waveform data obtained by gas chromatography analysis, proportions (%) of amounts of various fatty alcohols in the total amount of fatty alcohols produced by each transformant were calculated. Conditions of gas chromatography mass spectrometry analysis and gas chromatography analysis are the same with the conditions in Test Example 1.

FIG. 1 shows a chromatograph obtained by gas chromatography mass spectrometry analysis. Further, Table 12 shows the results of calculating the proportion (%) of the amounts of various fatty alcohols in the total amount of fatty alcohols by each transformant.

TABLE 12

| | % of total fatty alcohol | | |
|---|---|---|---|
| | C18:0-OH | C20:0-OH | C22:0-OH |
| wild type | n.d. | n.d. | n.d. |
| Δorf1593/1594::AtFAR4 | 100.00 | n.d. | n.d. |
| ΔNS1::NoKASII(−40) | n.d. | n.d. | n.d. |
| ΔNS1::NoKASII(−40)Δorf1593/1594::AtFAR4 | 26.86 | 73.14 | n.d. |
| ΔNS1::NoKASII(−40)Δorf1593/1594::AtFAR1 | 29.10 | 60.26 | 10.64 | n.d.: Not Detected

As shown in FIG. 1, *Synechococcus elongatus* sp. strain PCC7942 acquires ability to produce long-chain fatty acids having 20 or more carbon atoms by introducing a NoKASII gene thereinto. Moreover, as shown in FIG. 1 and Table 12, when the AtFAR4 gene was introduced into a wild strain, production of fatty alcohols having 18 carbon atoms was confirmed. However, in these strains, no long-chain fatty alcohol having 20 or more carbon atoms was detected.

On the other hand, as shown in FIG. 1 and Table 12, production of the long-chain fatty alcohol having 20 carbon atoms was confirmed by introducing the NoKASII gene and the AtFAR4 gene into the *Synechococcus elongatus* sp. strain PCC7942.

Further, ability to produce long-chain fatty alcohols having 20 and 22 carbon atoms was able to be provided by introducing the NoKASII gene and the AtFAR1 gene into the *Synechococcus elongatus* sp. strain PCC7942.

As described above, introduction of both the NoKASII gene and the AtFAR gene is important for acquiring the ability to produce the long-chain fatty alcohols and improving productivity in cyanobacteria.

Preparation Example 4 Preparation of Transformant by Introducing NoKASII Gene and AtFAR Gene into Cyanobacteria (1) Construction of Plasmid for Kanamycin Resistance Gene Expression Using genomic DNA of *Synechocystis* sp. strain PCC6803 as a template, and the primer pUC118/slr0168up-F and the primer Kmr/slr0168up-R described in Table 5, PCR was carried out to amplify the upstream fragment of a neutral site slr0168 region (slr0168up fragment; SEQ ID NO: 39). Further, using the genomic DNA described above as a template, and the primer Kmr/slr0168down-F and the primer pUC118/slr0168down-R described in Table 5, PCR was carried out to amplify the downstream fragment of a neutral site slr0168 region (slr0168down fragment; SEQ ID NO: 42).

A pUC118-slr0168::Km plasmid was obtained by inserting the slr0168up fragment, the slr0168down fragment, and a Kmr fragment prepared by a method in a manner similar to that described in Preparation Example 3, into the HincII site of the pUC118 plasmid (manufactured by Takara Bio) by using the In-Fusion (registered trademark) PCR cloning system (Clontech).

(2) Construction of Plasmid for NoKASII Expression

Using the pUC118-slr0168::Km plasmid as a template and the primer Kmr-F described in Table 4 and the primer slr0168up-R described in Table 5, PCR was carried out to amplify a linearized pUC118-slr0168::Km plasmid.

Then, using genomic DNA of *Synechocystis* sp. strain PCC6803 as a template, and the primer slr0168up/Pcpc560-F and the primer Pcpc560-R described in Table 5, PCR was carried out to amplify a fragment of high expression promoter of cpc560 (Jie Z et al., Scientific Reports, 2014, vol. 4, p. 4500; Pcpc560 fragment; SEQ ID NO: 49).

Further, PCR was carried out by using genomic DNA of *Synechocystis* sp. strain PCC6803 as a template, and the primer Trbc-F described in Table 4 and the primer Km/Trbc-R described in Table 5 to amplify a terminator fragment of a rbc gene (Trbc fragment, SEQ ID NO: 52).

Furthermore, using a cDNA library prepared from *Nannochloropsis oculata* strain NIES-2145 as a template, and the primer Pcpc560/NoKASII(−40)-F described in Table 5 and the primer Trbc/NoKASII-R described in Table 4, PCR was carried out to amplify a NoKASII(−40) gene fragment.

Then, the linearized pUC118-slr0168::Km plasmid, the Pcpc560 fragment, the Trbc fragment, and the NoKASII(−40) gene fragment were mixed, and the resultant mixture was cloned by using the In-Fusion (registered trademark) PCR Cloning system (Clontech) to obtain a pUC118-slr0168::Pcpc560-NoKASII(−40)-Trbc-Km plasmid in which the cpc560 promoter, the NoKASII(−40) gene fragment, the rbc terminator, and the kanamycin resistance gene cassette were inserted in this order into a neutral site slr0168 region derived from *Synechocystis* sp. strain PCC6803.

(3) Construction of Plasmid for Spectinomycin Resistance Gene Expression

Using genomic DNA of the wild-type strain of *Synechocystis* sp. strain PCC6803 as a template, and the primer pUC118/slI0208up-F and the primer Sp/slI0208up-R described in Table 5, PCR was carried out to amplify the upstream fragment of an slI0208 region (slI0208up fragment; SEQ ID NO: 57). Further, using the genomic DNA described above as a template, and the primer Sp/slI0209down-F and the primer pUC118/slI0209down-R described in Table 5, PCR was carried out to amplify the downstream fragment of an sll0209 region (sll0209down fragment; SEQ ID NO: 60).

A pUC118-sll0208/0209::Sp plasmid was obtained by inserting the sll0208up fragment, the sll0209down fragment, and a Sp fragment prepared by a method in a manner similar to that described in Preparation Example 3, into the HincII site of the pUC118 plasmid (manufactured by Takara Bio) by using the In-Fusion (registered trademark) PCR cloning system (Clontech).

(4) Construction of Plasmid for AtFAR Gene Expression

Using the pUC118-sll0208/0209::Sp plasmid as a template and the primer Sp-F described in Table 4 and the primer sll0208up-R described in Table 5, PCR was carried out to linearize the pUC118-sll0208/0209::Sp plasmid.

Then, using genomic DNA of *Synechocystis* sp. strain PCC6803 as a template, and the primer sll0208up/Pcpc560-F and the primer Pcpc560-R described in Table 5, PCR was carried out to amplify the Pcpc560 fragment (SEQ ID NO: 49).

Further, PCR was carried out by using a cDNA library prepared from *Arabidopsis thaliana* as a template, and the primer Pcpc560/AtFAR1-fw described in Table 5 and the primer Trbc/AtFAR1-ry described in Table 4 to amplify an AtFAR1 gene fragment (SEQ ID NO: 4). In a manner similar to that described above, PCR was carried out by using the primer Pcpc560/AtFAR4-fw described in Table 5 and the primer Trbc/AtFAR4-ry described in Table 4 to amplify an AtFAR4 gene fragment (SEQ ID NO: 8).

Then, the linearized pUC118-sll0208/0209::Sp plasmid, the Pcpc560 fragment, a Trbc fragment prepared by a method in a manner similar to that described in Preparation Example 3, and the AtFAR1 gene fragment or the AtFAR4 gene fragment were mixed, and the resultant mixture was cloned by using the In-Fusion (registered trademark) PCR Cloning system (Clontech) to obtain a pUC118-sll0208/0209::Pcpc560-AtFAR1-Trbc-Sp plasmid or a pUC118-sll0208/0209::Pcpc560-AtFAR4-Trbc-Sp plasmid in which the cpc560 promoter, the AtFAR1 gene fragment or the AtFAR4 gene fragment, the rbc terminator, and the spectinomycin resistance gene cassette were inserted in this order into a neutral site slr0168 region derived from *Synechocystis* sp. strain PCC6803.

(5) Introduction of Plasmid for NoKASII Gene Expression and Plasmid for AtFAR Gene Expression into Cyanobacteria Using thus-obtained pUC118-slr0168::Pcpc560-NoKASII(−40)-Trbc-Km plasmid, pUC118-sll0208/0209::Pcpc560-AtFAR1-Trbc-Sp plasmid, and pUC118-sll0208/0209::Pcpc560-AtFAR4-Trbc-Sp plasmid, *Synechocystis* sp. strain PCC6803 was transformed by a spontaneous transformation method, and the resultant material was selected by kanamycin resistance and spectinomycin resistance.

In this way, a Δslr0168::NoKASII(−40)Δsll0208/0209::AtFAR1 strain and a Δslr0168::NoKASII(−40)Δsll0208/0209::AtFAR4 strain were obtained, in which the construct for the NoKASII gene expression was introduced into the slr0168 region and the AtFAR1 gene or the AtFAR4 gene was introduced into the sll0208/0209 region on a genome of *Synechocystis* sp. strain PCC6803.

In addition, in a manner similar to that described above, a Δslr0168::NoKASII(−40) strain into which the construct for NoKASII(−40) gene expression was introduced into the slr0168 region, and a Δsll0208/0209::AtFAR1 strain or a Δsll0208/0209::AtFAR4 strain wherein the AtFAR1 gene or AtFAR4 gene was introduced into the sll0208/0209 region, were obtained respectively.

Test Example 3 Production of Fatty Alcohols

By a method in a manner similar to that described in Test Example 2, lipids were extracted from the transformants prepared in Preparation Example 4. Fatty acid methyl esters and trimethylsilylated fatty alcohols were identified by gas chromatography mass spectrometry analysis. Next, based on a peak area of waveform data obtained by gas chromatography analysis, proportions (%) of amounts of various fatty alcohols in the total amount of fatty alcohols produced by each transformant were calculated.

Figure 2:
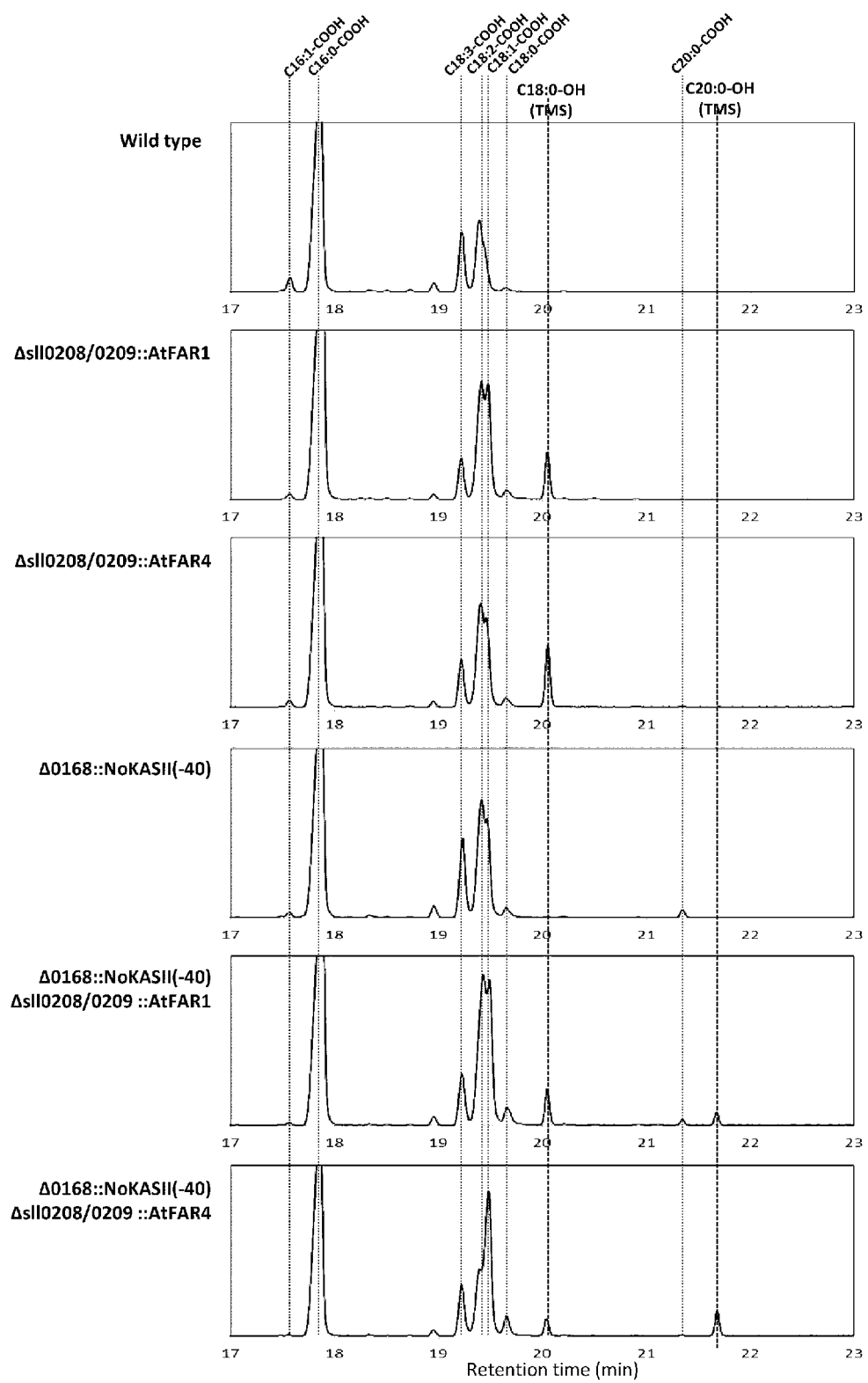
FIG. 2 is a graph showing a result of gas chromatography mass spectrometry analysis of fatty alcohols produced by transformants prepared in Preparation Example 4 in Example.

FIG. 2 shows the results of a chromatograph obtained by gas chromatography mass spectrometry analysis. Further, Table 13 shows the results of calculating the proportion (%) of the amounts of various fatty alcohols in the total amount of fatty alcohols by each transformant.

TABLE 13

|  | % of total fatty alcohol | |
| --- | --- | --- |
|  | C18:0-OH | C20:0-OH |
| wild type | n.d. | n.d. |
| Δsll0208/0209::AtFAR1 | 100.00 | n.d. |
| Δsll0208/0209::AtFAR4 | 100.00 | n.d. |
| Δ0168::NoKASII(−40) | n.d. | n.d. |
| Δ0168::NoKASII(−40)Δsll0208/0209::AtFAR1 | 66.78 | 33.22 |
| Δ0168::NoKASII(−40)Δsll0208/0209::AtFAR4 | 39.64 | 60.36 | n.d.: Not Detected

As shown in FIG. 2 and Table 13, similarly to the *Synechococcus elongatus* sp. strain PCC7942, the ability to produce the long-chain fatty alcohol having 20 carbon atoms was able to be provided also in the *Synechocystis* sp. strain PCC6803 by introducing the NoKASII gene and the AtFAR gene thereinto.

As described above, host microorganisms can be provided with the ability to produce the long-chain fatty alcohols by enhancing the expression of both the KAS gene and the FAR gene described above in cells of the host microorganisms such as *Escherichia coli* and cyanobacteria. The production amount of long-chain fatty alcohols is tend to increase in comparison with the host in which the expression of the genes is not enhanced. Such an effect is not obtained merely by enhancing the expression of the KAS gene and the FAR gene described above independently.

Therefore, a transformant in which the productivity of long-chain fatty alcohols is acquired or a transformant in which the productivity of long-chain fatty alcohols is improved can be prepared by enhancing the expression of both the KAS gene and the FAR gene. Further, the productivity of long-chain fatty alcohols can be improved by culturing the transformant.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2017-021708 filed in Japan on Feb. 8, 2017, which is entirely herein incorporated by reference.

What is claimed is:

1. A method of producing a long-chain fatty alcohol including a fatty alcohol having 20 or more carbon atoms, comprising
culturing a microorganism wherein expression of a gene encoding at least one kind of β-ketoacyl-ACP synthase selected from the group consisting of the following proteins (A) to (F) and expression of a gene encoding at least one kind of fatty acyl-CoA reductase selected from the group consisting of the following proteins (G) to (R) are enhanced;
(A) a protein consisting of the amino acid sequence set forth in SEQ ID NO: 1;
(B) a protein consisting of an amino acid sequence having 60% or more identity with the amino acid sequence of the protein (A), and having β-ketoacyl-ACP synthase II activity;
(C) a protein consisting of the amino acid sequence set forth in SEQ ID NO: 96;
(D) a protein consisting of an amino acid sequence having 60% or more identity with the amino acid sequence of the protein (C), and having β-ketoacyl-ACP synthase II activity;
(E) a protein consisting of the amino acid sequence set forth in SEQ ID NO: 98;
(F) a protein consisting of an amino acid sequence having 60% or more identity with the amino acid sequence of the protein (E), and having β-ketoacyl-ACP synthase II activity;
(G) a protein consisting of the amino acid sequence set forth in SEQ ID NO: 3;
(H) a protein consisting of an amino acid sequence having 80% or more identity with the amino acid sequence of the protein (G), and having fatty acyl-CoA reductase activity;
(I) a protein consisting of the amino acid sequence set forth in SEQ ID NO: 5;
(J) a protein consisting of an amino acid sequence having 80% or more identity with the amino acid sequence of the protein (I), and having fatty acyl-CoA reductase activity;
(K) a protein consisting of the amino acid sequence set forth in SEQ ID NO: 7;
(L) a protein consisting of an amino acid sequence having 80% or more identity with the amino acid sequence of the protein (K), and having fatty acyl-CoA reductase activity;
(M) a protein consisting of the amino acid sequence set forth in SEQ ID NO: 9;
(N) a protein consisting of an amino acid sequence having 80% or more identity with the amino acid sequence of the protein (M), and having fatty acyl-CoA reductase activity;
(O) a protein consisting of the amino acid sequence set forth in SEQ ID NO: 100;
(P) a protein consisting of an amino acid sequence having 80% or more identity with the amino acid sequence of the protein (O), and having fatty acyl-CoA reductase activity;
(Q) a protein consisting of the amino acid sequence set forth in SEQ ID NO: 101; and
(R) a protein consisting of an amino acid sequence having 80% or more identity with the amino acid sequence of the protein (Q), and having fatty acyl-CoA reductase activity.

2. The method of producing a long-chain fatty alcohol according to claim 1, wherein the gene encoding the β-ketoacyl-ACP synthase and the gene encoding the fatty acyl-CoA reductase gene are introduced into the microorganism, to enhance the expression of the gene encoding the β-ketoacyl-ACP synthase and the gene encoding the fatty acyl-CoA reductase gene introduced.

3. The method of producing a long-chain fatty alcohol according to claim 2, comprising the steps of
separating a solution containing fatty alcohols including long-chain fatty alcohols from media,
wherein the long-chain fatty alcohol to be produced includes a fatty alcohol having 20 or more carbon atoms.

4. The method of producing a long-chain fatty alcohol according to claim 1, wherein
the protein (B) is a protein consisting of an amino acid sequence having 90% or more identity with the amino acid sequence of the protein (A), and having β-ketoacyl-ACP synthase II activity;

the protein (D) is a protein consisting of an amino acid sequence having 90% or more identity with the amino acid sequence of the protein (C), and having β-ketoacyl-ACP synthase II activity; and the protein (F) is a protein consisting of an amino acid sequence having 90% or more identity with the amino acid sequence of the protein (E), and having β-ketoacyl-ACP synthase II.

5. The method of producing a long-chain fatty alcohol according to claim 1, wherein the protein (H) is a protein consisting of an amino acid sequence having 90% or more identity with the amino acid sequence of the protein (G), and having fatty acyl-CoA reductase activity;

the protein (J) is a protein consisting of an amino acid sequence having 90% or more identity with the amino acid sequence of the protein (I), and having fatty acyl-CoA reductase activity;

the protein (L) is a protein consisting of an amino acid sequence having 90% or more identity with the amino acid sequence of the protein (K), and having fatty acyl-CoA reductase activity;

the protein (N) is a protein consisting of an amino acid sequence having 90% or more identity with the amino acid sequence of the protein (M), and having fatty acyl-CoA reductase activity;

the protein (P) is a protein consisting of an amino acid sequence having 90% or more identity with the amino acid sequence of the protein (O), and having fatty acyl-CoA reductase activity; and the protein (R) is a protein consisting of an amino acid sequence having 90% or more identity with the amino acid sequence of the protein (Q), and having fatty acyl-CoA reductase activity.

6. The method of producing a long-chain fatty alcohol according to claim 1, wherein the microorganism lacked the ability to produce a long-chain fatty alcohol having 20 or more carbon atoms prior to enhancing expression of the gene encoding the β-ketoacyl-ACP synthase and the gene encoding the fatty acyl-CoA reductase.

7. The method of producing a long-chain fatty alcohol according to claim 1, wherein the microorganism is *Escherichia coli* or cyanobacteria.

8. The method of producing a long-chain fatty alcohol according to claim 7, wherein the cyanobacteria are cyanobacteria of the genus *Synechocystis* or the genus *Synechococcus*.

9. The method of producing a long-chain fatty alcohol according to claim 1, wherein the long-chain fatty alcohol is a long-chain fatty alcohol having 20 to 26 carbon atoms.

10. The method of producing a long-chain fatty alcohol according to claim 1, wherein the amount of the long-chain fatty alcohols having 20 or more carbon atoms in the amount of the total fatty alcohols produced by the microorganism is 1% or more with respect to the weight of the total fatty alcohols.

11. The method of producing a long-chain fatty alcohol according to claim 1, wherein the long-chain fatty alcohol after culturing exists in an extracellular medium.

12. The method of producing a long-chain fatty alcohol according to claim 11, which comprises the step of separating the microorganism from at least a part of the medium containing the fatty alcohols after culturing.

13. A transformant of a microorganism, in which expression of a gene encoding at least one kind of β-ketoacyl-ACP synthase selected from the group consisting of the following proteins (A) to (F) and expression of a gene encoding at least one kind of fatty acyl-CoA reductase selected from the group consisting of the following proteins (G) to (R) are enhanced;

(A) a protein consisting of the amino acid sequence set forth in SEQ ID NO: 1;

(B) a protein consisting of an amino acid sequence having 60% or more identity with the amino acid sequence of the protein (A), and having β-ketoacyl-ACP synthase II activity;

(C) a protein consisting of the amino acid sequence set forth in SEQ ID NO: 96;

(D) a protein consisting of an amino acid sequence having 60% or more identity with the amino acid sequence of the protein (C), and having P-ketoacyl-ACP synthase II activity;

(E) a protein consisting of the amino acid sequence set forth in SEQ ID NO: 98;

(F) a protein consisting of an amino acid sequence having 60% or more identity with the amino acid sequence of the protein (E), and having β-ketoacyl-ACP synthase II activity;

(G) a protein consisting of the amino acid sequence set forth in SEQ ID NO: 3;

(H) a protein consisting of an amino acid sequence having 80% or more identity with the amino acid sequence of the protein (G), and having fatty acyl-CoA reductase activity;

(I) a protein consisting of the amino acid sequence set forth in SEQ ID NO: 5;

(J) a protein consisting of an amino acid sequence having 80% or more identity with the amino acid sequence of the protein (I), and having fatty acyl-CoA reductase activity;

(K) a protein consisting of the amino acid sequence set forth in SEQ ID NO: 7;

(L) a protein consisting of an amino acid sequence having 80% or more identity with the amino acid sequence of the protein (K), and having fatty acyl-CoA reductase activity;

(M) a protein consisting of the amino acid sequence set forth in SEQ ID NO: 9;

(N) a protein consisting of an amino acid sequence having 80% or more identity with the amino acid sequence of the protein (M), and having fatty acyl-CoA reductase activity;

(O) a protein consisting of the amino acid sequence set forth in SEQ ID NO: 100;

(P) a protein consisting of an amino acid sequence having 80% or more identity with the amino acid sequence of the protein (O), and having fatty acyl-CoA reductase activity;

(Q) a protein consisting of the amino acid sequence set forth in SEQ ID NO: 101; and (R) a protein consisting of an amino acid sequence having 80% or more identity with the amino acid sequence of the protein (Q), and having fatty acyl-CoA reductase activity.

14. The transformant according to claim 13, wherein the gene encoding the β-ketoacyl-ACP synthase or a recombinant vector containing the same, and the gene encoding the fatty acyl-CoA reductase or a recombinant vector containing the same are introduced into the microorganism.

15. The transformant according to claim 13, wherein the protein (B) is a protein consisting of an amino acid sequence having 90% or more identity with the amino acid sequence of the protein (A), and having β-ketoacyl-ACP synthase II activity;

the protein (D) is a protein consisting of an amino acid sequence having 90% or more identity with the amino acid sequence of the protein (C), and having β-ketoacyl-ACP synthase II activity; and the protein (F) is a protein consisting of an amino acid sequence having 90% or more identity with the amino acid sequence of the protein (E), and having β-ketoacyl-ACP synthase II.

16. The transformant according to claim 13, wherein the protein (H) is a protein consisting of an amino acid sequence having 90% or more identity with the amino acid sequence of the protein (G), and having fatty acyl-CoA reductase activity;

the protein (J) is a protein consisting of an amino acid sequence having 90% or more identity with the amino acid sequence of the protein (I), and having fatty acyl-CoA reductase activity;

the protein (L) is a protein consisting of an amino acid sequence having 90% or more identity with the amino acid sequence of the protein (K), and having fatty acyl-CoA reductase activity;

the protein (N) is a protein consisting of an amino acid sequence having 90% or more identity with the amino acid sequence of the protein (M), and having fatty acyl-CoA reductase activity;

the protein (P) is a protein consisting of an amino acid sequence having 90% or more identity with the amino acid sequence of the protein (O), and having fatty acyl-CoA reductase activity; and the protein (R) is a protein consisting of an amino acid sequence having 90% or more identity with the amino acid sequence of the protein (Q), and having fatty acyl-CoA reductase activity.

17. The transformant according to claim 13, wherein the microorganism lacked the ability to produce a long-chain fatty alcohol having 20 or more carbon atoms prior to enhancing expression of the gene encoding the β-ketoacyl-ACP synthase and the gene encoding the fatty acyl-CoA reductase.

18. The transformant according to claim 13, wherein the microorganism is *Escherichia coli* or cyanobacteria.

19. The transformant according to claim 18, wherein the cyanobacteria are cyanobacteria of the genus *Synechocystis* or the genus *Synechococcus*.

\* \* \* \* \*